(12) United States Patent
Thapliyal et al.

(10) Patent No.: US 10,052,121 B2
(45) Date of Patent: *Aug. 21, 2018

(54) METHOD FOR ABLATING BODY TISSUE

(71) Applicant: VytronUS, Inc., Sunnyvale, CA (US)

(72) Inventors: Hira V. Thapliyal, Los Altos, CA (US);
David A. Gallup, Alameda, CA (US);
James W. Arenson, Woodside, CA (US)

(73) Assignee: Vytronus, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/654,779

(22) Filed: Jul. 20, 2017

(65) Prior Publication Data
US 2017/0311973 A1 Nov. 2, 2017

Related U.S. Application Data

(63) Continuation of application No. 14/083,242, filed on Nov. 18, 2013, now Pat. No. 9,737,325, which is a
(Continued)

(51) Int. Cl.
*A61B 17/00* (2006.01)
*A61B 17/32* (2006.01)
(Continued)

(52) U.S. Cl.
CPC .. *A61B 17/320068* (2013.01); *A61B 18/1492* (2013.01); *A61N 7/02* (2013.01);
(Continued)

(58) Field of Classification Search
CPC ........ A61B 17/320068; A61B 18/1492; A61B 17/2202; A61B 18/24; A61B 2017/00106;
(Continued)

(56) References Cited

U.S. PATENT DOCUMENTS 4,641,649 A 2/1987 Walinsky et al.
4,757,820 A 7/1988 Itoh
(Continued)

FOREIGN PATENT DOCUMENTS

DE 10037660 A1 2/2002
JP 2002534152 A 10/2002
(Continued)

OTHER PUBLICATIONS

A new treatment for atrial fibrillation? Feb. 2006, Medical Device & Diagnostic Industry, Medical Device Link, http://www.devicelink.com/mddi/archive/06/02/013.html.
(Continued)

*Primary Examiner* — Aaron Roane
(74) *Attorney, Agent, or Firm* — Wilson Sonsini Goodrich & Rosati

(57) ABSTRACT

A cardiac ablation method including the following steps: inserting a treatment catheter into an atrium of a heart, the treatment catheter including an ultrasound emitter; positioning the ultrasound emitter to face heart tissue within the left atrium outside of a pulmonary vein; emitting ultrasound energy from the ultrasound emitter while rotating the ultrasound emitter about a rotation axis; and ablating heart tissue with the ultrasound energy to form a lesion outside of a pulmonary vein.

20 Claims, 36 Drawing Sheets

Related U.S. Application Data continuation of application No. 13/630,652, filed on Sep. 28, 2012, now Pat. No. 8,607,800, which is a continuation of application No. 13/405,712, filed on Feb. 27, 2012, now Pat. No. 8,511,317, which is a continuation of application No. 13/092,747, filed on Apr. 22, 2011, now Pat. No. 8,146,603, which is a continuation of application No. 11/747,862, filed on May 11, 2007, now Pat. No. 7,950,397.

(60) Provisional application No. 60/747,137, filed on May 12, 2006, provisional application No. 60/919,831, filed on Mar. 23, 2007.

(51) Int. Cl.
| | | |
|---|---|---|
| *A61N 7/02* | (2006.01) | |
| *A61B 18/14* | (2006.01) | |
| A61N 7/00 | (2006.01) | |
| A61B 18/00 | (2006.01) | |
| A61B 17/22 | (2006.01) | |
| A61B 18/24 | (2006.01) | |

(52) U.S. Cl.
CPC .......... *A61N 7/022* (2013.01); *A61B 17/2202* (2013.01); *A61B 18/24* (2013.01); *A61B 2017/003* (2013.01); *A61B 2017/00106* (2013.01); *A61B 2017/00243* (2013.01); *A61B 2017/22024* (2013.01); *A61B 2018/00029* (2013.01); *A61N 2007/0078* (2013.01)

(58) Field of Classification Search
CPC .... A61B 2017/00243; A61B 2017/003; A61B 2017/22024; A61B 2018/00029; A61N 7/02; A61N 7/022; A61N 2007/0078
USPC .......................................................... 606/27
See application file for complete search history.

(56) References Cited

U.S. PATENT DOCUMENTS

| | | |
|---|---|---|
| 5,139,496 A | 8/1992 | Hed |
| 5,246,438 A | 9/1993 | Langberg |
| 5,295,484 A | 3/1994 | Marcus et al. |
| 5,314,466 A | 5/1994 | Stern et al. |
| 5,405,346 A | 4/1995 | Grundy et al. |
| 5,421,335 A | 6/1995 | Wild |
| 5,718,241 A | 2/1998 | Ben-Haim et al. |
| 5,735,811 A | 4/1998 | Brisken |
| 6,012,457 A | 1/2000 | Lesh |
| 6,024,740 A | 2/2000 | Lesh et al. |
| 6,052,576 A | 4/2000 | Lambourg |
| 6,064,902 A | 5/2000 | Haissaguerre et al. |
| 6,117,101 A | 9/2000 | Diederich et al. |
| 6,161,543 A | 12/2000 | Cox et al. |
| 6,164,283 A | 12/2000 | Lesh |
| 6,237,605 B1 | 5/2001 | Vaska et al. |
| 6,245,064 B1 | 6/2001 | Lesh et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,599 B1 | 7/2001 | Lesh et al. |
| 6,261,312 B1 | 7/2001 | Dobak, III et al. |
| 6,277,116 B1 | 8/2001 | Utely et al. |
| 6,305,378 B1 | 10/2001 | Lesh |
| 6,311,090 B1 | 10/2001 | Knowlton |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,379,378 B1 | 4/2002 | Werneth et al. |
| 6,383,151 B1 | 5/2002 | Diederich et al. |
| 6,387,089 B1 | 5/2002 | Kreindel et al. |
| 6,416,511 B1 | 7/2002 | Lesh et al. |
| 6,468,296 B1 | 10/2002 | Dobak, III et al. |
| 6,474,340 B1 | 11/2002 | Vaska et al. |
| 6,475,231 B2 | 11/2002 | Dobak et al. |
| 6,478,811 B1 | 11/2002 | Dobak, III et al. |
| 6,478,812 B2 | 11/2002 | Dobak et al. |
| 6,484,727 B1 | 11/2002 | Vaska et al. |
| 6,491,039 B1 | 12/2002 | Dobak, III |
| 6,491,716 B2 | 12/2002 | Dobak et al. |
| 6,500,121 B1 | 12/2002 | Slayton et al. |
| 6,500,174 B1 | 12/2002 | Maguire et al. |
| 6,502,576 B1 | 1/2003 | Lesh |
| 6,514,244 B2 | 2/2003 | Pope et al. |
| 6,514,249 B1 | 2/2003 | Maguire et al. |
| 6,517,536 B2 | 2/2003 | Hooven et al. |
| 6,529,756 B1 | 3/2003 | Phan et al. |
| 6,533,804 B2 | 3/2003 | Dobak et al. |
| 6,540,771 B2 | 4/2003 | Dobak et al. |
| 6,542,781 B1 | 4/2003 | Koblish et al. |
| 6,546,935 B2 | 4/2003 | Hooven |
| 6,547,788 B1 | 4/2003 | Maguire et al. |
| 6,551,349 B2 | 4/2003 | Lasheras et al. |
| 6,576,001 B2 | 6/2003 | Werneth et al. |
| 6,582,455 B1 | 6/2003 | Dobak, III et al. |
| 6,585,752 B2 | 7/2003 | Dobak et al. |
| 6,592,576 B2 | 7/2003 | Andrews et al. |
| 6,595,989 B1 | 7/2003 | Schaer |
| 6,599,288 B2 | 7/2003 | Maguire et al. |
| 6,602,276 B2 | 8/2003 | Dobak, III et al. |
| 6,605,084 B2 | 8/2003 | Acker et al. |
| 6,607,502 B1 | 8/2003 | Maguire et al. |
| 6,607,527 B1 | 8/2003 | Ruiz et al. |
| 6,613,046 B1 | 9/2003 | Jenkins et al. |
| 6,635,054 B2 | 10/2003 | Fjield et al. |
| 6,645,199 B1 | 11/2003 | Jenkins et al. |
| 6,645,202 B1 | 11/2003 | Pless et al. |
| 6,648,908 B2 | 11/2003 | Dobak et al. |
| 6,652,515 B1 | 11/2003 | Maguire et al. |
| 6,652,517 B1 | 11/2003 | Hall et al. |
| 6,666,614 B1 | 12/2003 | Fechter et al. |
| 6,666,858 B2 | 12/2003 | Lafontaine |
| 6,669,655 B1 | 12/2003 | Acker et al. |
| 6,669,687 B1 | 12/2003 | Saadat |
| 6,676,688 B2 | 1/2004 | Dobak et al. |
| 6,676,689 B2 | 1/2004 | Dobak et al. |
| 6,676,690 B2 | 1/2004 | Werneth |
| 6,685,732 B2 | 2/2004 | Kramer |
| 6,689,128 B2 | 2/2004 | Sliwa et al. |
| 6,692,488 B2 | 2/2004 | Dobak et al. |
| 6,695,873 B2 | 2/2004 | Dobak et al. |
| 6,701,931 B2 | 3/2004 | Sliwa et al. |
| 6,702,842 B2 | 3/2004 | Dobak et al. |
| 6,711,444 B2 | 3/2004 | Koblish |
| 6,719,755 B2 | 4/2004 | Sliwa et al. |
| 6,745,080 B2 | 6/2004 | Koblish |
| 6,752,805 B2 | 6/2004 | Maguire et al. |
| 6,758,847 B2 | 7/2004 | Maguire |
| 6,763,722 B2 | 7/2004 | Fjield et al. |
| 6,780,183 B2 | 8/2004 | Jimenez et al. |
| 6,786,218 B2 | 9/2004 | Dobak et al. |
| 6,805,128 B1 | 10/2004 | Pless et al. |
| 6,805,129 B1 | 10/2004 | Pless et al. |
| 6,814,733 B2 | 11/2004 | Schwartz et al. |
| 6,840,936 B2 | 1/2005 | Sliwa et al. |
| 6,858,026 B2 | 2/2005 | Sliwa et al. |
| 6,869,431 B2 | 3/2005 | Maguire et al. |
| 6,872,205 B2 | 3/2005 | Lesh et al. |
| 6,889,694 B2 | 5/2005 | Hooven |
| 6,893,438 B2 | 5/2005 | Hall et al. |
| 6,896,673 B2 | 5/2005 | Hooven |
| 6,899,710 B2 | 5/2005 | Hooven |
| 6,899,711 B2 | 5/2005 | Stewart et al. |
| 6,904,303 B2 | 6/2005 | Phan et al. |
| 6,905,494 B2 | 6/2005 | Yon et al. |
| 6,905,498 B2 | 6/2005 | Hooven |
| 6,905,509 B2 | 6/2005 | Dobak et al. |
| 6,908,464 B2 | 6/2005 | Jenkins et al. |
| 6,920,883 B2 | 7/2005 | Bessette et al. |
| 6,923,806 B2 | 8/2005 | Hooven et al. |
| 6,923,808 B2 | 8/2005 | Taimisto |

(56) References Cited

U.S. PATENT DOCUMENTS

| | | |
|---|---|---|
| 6,929,639 B2 | 8/2005 | Lafontaine |
| 6,932,811 B2 | 8/2005 | Hooven et al. |
| 6,949,095 B2 | 9/2005 | Vaska et al. |
| 6,949,097 B2 | 9/2005 | Stewart et al. |
| 6,953,460 B2 | 10/2005 | Maguire et al. |
| 6,954,977 B2 | 10/2005 | Maguire et al. |
| 6,955,173 B2 | 10/2005 | Lesh |
| 6,964,660 B2 | 11/2005 | Maguire et al. |
| 6,966,908 B2 | 11/2005 | Maguire et al. |
| 6,971,394 B2 | 12/2005 | Sliwa et al. |
| 6,974,454 B2 | 12/2005 | Hooven |
| 6,984,233 B2 | 1/2006 | Hooven |
| 6,997,925 B2 | 2/2006 | Maguire et al. |
| 7,001,378 B2 | 2/2006 | Yon et al. |
| 7,001,415 B2 | 2/2006 | Hooven |
| 7,008,418 B2 | 3/2006 | Hall et al. |
| 7,044,135 B2 | 5/2006 | Lesh |
| 7,063,682 B1 | 6/2006 | Whayne et al. |
| 7,142,905 B2 | 11/2006 | Slayton et al. |
| 7,275,450 B2 | 10/2007 | Hirai et al. |
| 7,285,116 B2 | 10/2007 | Rama et al. |
| 7,306,593 B2 | 12/2007 | Keidar et al. |
| 7,393,325 B2 | 7/2008 | Barthe et al. |
| 7,942,871 B2 | 5/2011 | Thapliyal et al. |
| 7,950,397 B2* | 5/2011 | Thapliyal ........... A61B 18/1492 128/898 |
| 8,146,603 B2* | 4/2012 | Thapliyal ........... A61B 18/1492 128/898 |
| 8,511,317 B2* | 8/2013 | Thapliyal ........... A61B 18/1492 128/898 |
| 8,607,800 B2* | 12/2013 | Thapliyal ........... A61B 18/1492 128/898 |
| 9,737,325 B2* | 8/2017 | Thapliyal ....... A61B 17/320068 |
| 2002/0087151 A1 | 7/2002 | Mody et al. |
| 2003/0050630 A1 | 3/2003 | Mody et al. |
| 2003/0050631 A1 | 3/2003 | Mody et al. |
| 2003/0125726 A1 | 7/2003 | Maguire et al. |
| 2004/0034347 A1 | 2/2004 | Hall et al. |
| 2004/0243124 A1 | 12/2004 | Im et al. |
| 2005/0049582 A1 | 3/2005 | Debenedictis et al. |
| 2005/0165388 A1 | 7/2005 | Bhola |
| 2005/0171530 A1 | 8/2005 | Hooven |
| 2005/0256518 A1 | 11/2005 | Rama et al. |
| 2006/0084966 A1 | 4/2006 | Maguire et al. |
| 2006/0122508 A1 | 6/2006 | Slayton et al. |
| 2007/0027445 A1 | 2/2007 | Gifford et al. |
| 2007/0265609 A1 | 11/2007 | Thapliyal et al. |
| 2007/0265610 A1 | 11/2007 | Thapliyal et al. |
| 2008/0039746 A1 | 2/2008 | Hissong et al. |
| 2008/0077200 A1 | 3/2008 | Bendett et al. |
| 2012/0157984 A1 | 6/2012 | Thapliyal et al. |
| 2013/0096592 A1 | 4/2013 | Thapliyal et al. |
| 2014/0081302 A1 | 3/2014 | Thapliyal et al. |

FOREIGN PATENT DOCUMENTS

| | | |
|---|---|---|
| JP | 2003509087 A | 3/2003 |
| WO | WO-9826724 A1 | 6/1998 |
| WO | WO-9902096 A1 | 1/1999 |
| WO | WO-02085192 A2 | 10/2002 |
| WO | WO-02085192 A3 | 5/2003 |
| WO | WO-2004073505 A2 | 9/2004 |
| WO | WO-2005009265 A1 | 2/2005 |
| WO | WO-2005041753 A2 | 5/2005 |
| WO | WO-2004073505 A3 | 6/2005 |
| WO | WO-2005041753 A3 | 6/2005 |
| WO | WO-2005117734 A2 | 12/2005 |
| WO | WO-2005117734 A3 | 12/2006 |
| WO | WO-2007134258 A2 | 11/2007 |

OTHER PUBLICATIONS

Bushberg, et al.; The essential physics of medical imaging. 2nd Ed.; Lippincott Williams & Wilkins; 2002; 491.
Cox, et al. Current status of the Maze procedure for the treatment of atrial fibrillation. Seminars in Thoracic & Cardiovascular Surgery. 2000; 12:15-19.
Cox, et al. Electrophysiologic basis, surgical development, and clinical results of the maze procedure for atrial flutter and atrial fibrillation. Advances in Cardiac Surgery. 1995; 6:1-67.
Cox, et al. Modification of the maze procedure for atrial flutter and atrial fibrillation. II, Surgical technique of the maze III procedure. Journal of Thoracic & Cardiovascular Surgery. 1995;110:485-95.
Cox, et al. The development of the Maze procedure for the treatment of atrial fibrillation. Seminars in Thoracic & Cardiovascular Surgery. 2000; 12:2-14.
European search report dated Mar. 18, 2011 for EP 07783687.2.
European search report dated Nov. 23, 2012 for EP 12186737.8.
Gentry, et al. Integrated Catheter for 3-D Intracardiac Echocardiography and Ultrasound Ablation. IEEE Transactions on Ultrasonics, Ferroelectrics, and Frequency Control. 2004;51(7):800-808.
Gill. How to perform pulmonary vein isolation. Europace. 2004; 6(2):83-91.
Gillinov, et al. Atrial fibrillation: current surgical options and their assessment. Annals of Thoracic Surgery. 2002;74:2210-7.
Haissaguerre, et al. Spontaneous Initiation of Atrial Fibrillation by Ectopic Beats Originating in the Pulmonary Veins. New England J Med. 1998; 339:659-666.
International search report and written opinion dated Jul. 31, 2008 for PCT/US2007/068818.
Levinson. Endocardial Microwave Ablation: A New Surgical Approach for Atrial Fibrillation. The Heart urgery Forum. 2006.
Maessen, et al. Beating heart surgical treatment of atrial fibrillation with microwave ablation. Ann Thorac Surg. 2002; 74: 1160-8.
Nathan, et al. The junction between the left atrium and the pulmonary veins, an anatomic study of human hearts. Circulation. 1966; 34:412-422.
Office action dated Jan. 29, 2013 for U.S. Appl. No. 13/405,712.
Office action dated Mar. 18, 2013 for U.S. Appl. No. 13/630,652.
Office action dated Mar. 22, 2010 for U.S. Appl. No. 11/747,862.
Office action dated Mar. 23, 2010 for U.S. Appl. No. 11/747,867.
Office action dated May 17, 2012 for U.S. Appl. No. 13/405,712.
Office action dated Jun. 17, 2009 for U.S. Appl. No. 11/747,862.
Office action dated Jun. 18, 2009 for U.S. Appl. No. 11/747,867.
Office action dated Jul. 7, 2011 for U.S. Appl. No. 13/092,747.
Office action dated Jul. 19, 2010 for U.S. Appl. No. 11/747,867.
Office action dated Jul. 20, 2010 for U.S. Appl. No. 11/747,862.
Sueda, et al. Efficacy of a simple left atrial procedure for chronic atrial fibrillation in mitral valve operations. Ann Thorac Surg. 1997; 63:1070-1075.
Sueda, et al. Simple left atrial procedure for chronic atrial fibrillation associated with mitral valve disease. Ann Thorac Surg 1996; 62:1796-1800.
Ter Haar. Acoustic surgery. Physics Today. Dec. 2001; 54(12):29-34.
Notice of Allowance dated Apr. 28, 2017 for U.S. Appl. No. 14/083,242.

* cited by examiner

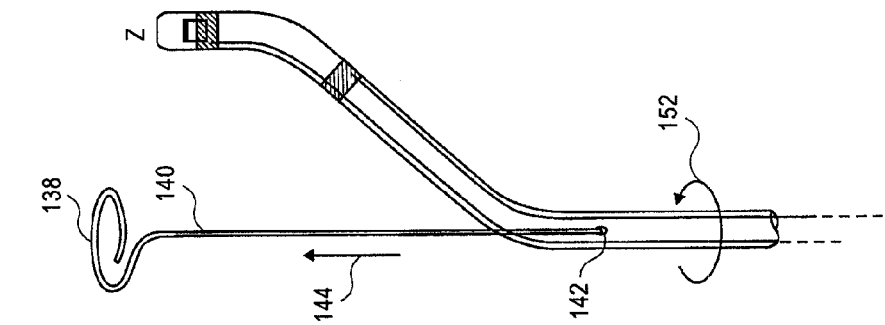
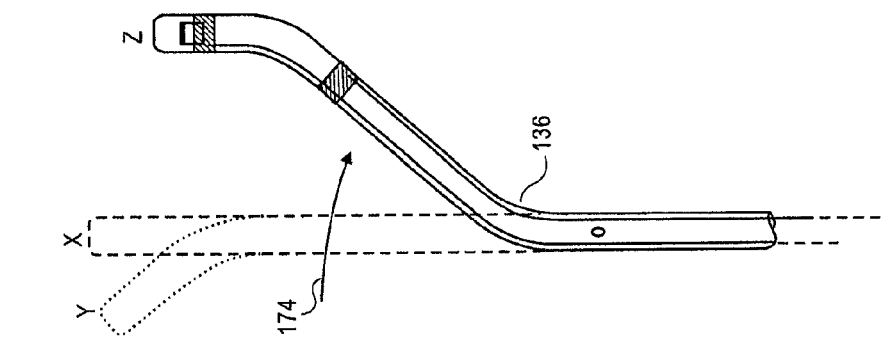
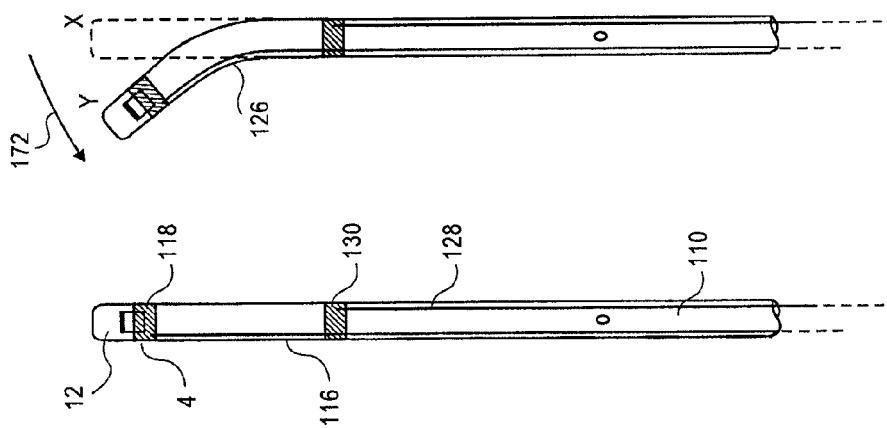
FIG. 3A   FIG. 3B   FIG. 3C   FIG. 3D

METHOD FOR ABLATING BODY TISSUE

CROSS-REFERENCE TO RELATED APPLICATIONS

The present application is a continuation of U.S. patent application Ser. No. 14/083,242, filed Nov. 18, 2013, now U.S. Pat. No. 9,737,325, which is a continuation of U.S. patent application Ser. No. 13/630,652, filed Sep. 28, 2012, now U.S. Pat. No. 8,607,800, which is a continuation of U.S. patent application Ser. No. 13/405,712, filed Feb. 27, 2012, now U.S. Pat. No. 8,511,317, which is a continuation of U.S. patent application Ser. No. 13/092,747 filed on Apr. 22, 2011, now U.S. Pat. No. 8,146,603, which is a continuation of U.S. patent application Ser. No. 11/747,862 filed May 11, 2007, now U.S. Pat. No. 7,950,397, which is a non-provisional of and claims the benefit of U.S. Provisional Application Nos. 60/747,137 filed May 12, 2006, and 60/919,831 filed Mar. 23, 2007, the entire contents of each are incorporated herein by reference.

All publications and patent applications mentioned in this specification are herein incorporated by reference to the same extent as if each individual publication or patent application was specifically and individually indicated to be incorporated by reference.

BACKGROUND OF THE INVENTION

1. Field of the Invention

In this invention we describe a device and a method for creating ablation zones in human tissue. More specifically, this invention pertains to the treatment of atrial fibrillation of the heart by using ultrasound energy.

2. Background

The condition of atrial fibrillation is characterized by the abnormal (usually very rapid) beating of left atrium of the heart which is out of synch with the normal synchronous movement ("normal sinus rhythm") of the heart muscle. In normal sinus rhythm, the electrical impulses originate in the sinoatrial node ("SA node") which resides in the right atrium. The abnormal beating of the atrial heart muscle is known as fibrillation and is caused by electrical impulses originating instead in the pulmonary veins ("PV") [Haissaguerre, M. et al., Spontaneous Initiation of Atrial Fibrillation by Ectopic Beats Originating in the Pulmonary Veins, New England J. Med., Vol. 339:659-666].

There are pharmacological treatments for this condition with varying degree of success. In addition, there are surgical interventions aimed at removing the aberrant electrical pathways from PV to the left atrium ("LA") such as the Cox-Maze III Procedure [J. L. Cox et al., The development of the Maze procedure for the treatment of atrial fibrillation, Seminars in Thoracic & Cardiovascular Surgery, 2000; 12: 2-14; J. L. Cox et al., Electrophysiologic basis, surgical development, and clinical results of the maze procedure for atrial flutter and atrial fibrillation, Advances in Cardiac Surgery, 1995; 6: 1-67; and J. L. Cox et al., Modification of the maze procedure for atrial flutter and atrial fibrillation. II, Surgical technique of the maze III procedure, Journal of Thoracic & Cardiovascular Surgery, 1995; 2110:485-95]. This procedure is shown to be 99% effective [J. L. Cox, N. Ad, T. Palazzo. et al. Current status of the Maze procedure for the treatment of atrial fibrillation, Seminars in Thoracic & Cardiovascular Surgery, 2000; 12: 15-19] but requires special surgical skills and is time consuming.

There has been considerable effort to copy the Cox-Maze procedure for a less invasive percutaneous catheter-based approach. Less invasive treatments have been developed which involve use of some form of energy to ablate (or kill) the tissue surrounding the aberrant focal point where the abnormal signals originate in PV. The most common methodology is the use of radio-frequency ("RF") electrical energy to heat the muscle tissue and thereby ablate it. The aberrant electrical impulses are then prevented from traveling from PV to the atrium (achieving conduction block within the heart tissue) and thus avoiding the fibrillation of the atrial muscle. Other energy sources, such as microwave, laser, and ultrasound have been utilized to achieve the conduction block. In addition, techniques such as cryoablation, administration of ethanol, and the like have also been used.

There has been considerable effort in developing the catheter based systems for the treatment of AF using radiofrequency (RF) energy. One such method is described in U.S. Pat. No. 6,064,902 to Haissaguerre et al. In this approach, a catheter is made of distal and proximal electrodes at the tip. The catheter can be bent in a J shape and positioned inside a pulmonary vein. The tissue of the inner wall of the PV is ablated in an attempt to kill the source of the aberrant heart activity. Other RF based catheters are described in U.S. Pat. No. 6,814,733 to Schwartz et al., U.S. Pat. No. 6,996,908 to Maguire et al., U.S. Pat. No. 6,955,173 to Lesh; and U.S. Pat. No. 6,949,097 to Stewart et al.

A source used in ablation is microwave energy. One such device is described by Dr. Mark Levinson [(Endocardial Microwave Ablation: A New Surgical Approach for Atrial Fibrillation; The Heart Surgery Forum, 2006] and Maessen et al. [Beating heart surgical treatment of atrial fibrillation with microwave ablation. Ann Thorac Surg 74: 1160-8, 2002]. This intraoperative device consists of a probe with a malleable antenna which has the ability to ablate the atrial tissue. Other microwave based catheters are described in U.S. Pat. No. 4,641,649 to Walinsky; U.S. Pat. No. 5,246,438 to Langberg; U.S. Pat. No. 5,405,346 to Grundy, et al.; and U.S. Pat. No. 5,314,466 to Stern, et al.

Another catheter based method utilizes the cryogenic technique where the tissue of the atrium is frozen below a temperature of −60 degrees C. This results in killing of the tissue in the vicinity of the PV thereby eliminating the pathway for the aberrant signals causing the AF [A. M. Gillinov, E. H. Blackstone and P. M. McCarthy, Atrial fibrillation: current surgical options and their assessment, Annals of Thoracic Surgery 2002; 74:2210-7]. Cryo-based techniques have been a part of the partial Maze procedures [Sueda T., Nagata H., Orihashi K., et al., Efficacy of a simple left atrial procedure for chronic atrial fibrillation in mitral valve operations, Ann Thorac Surg 1997; 63:1070-1075; and Sueda T., Nagata H., Shikata H., et al.; Simple left atrial procedure for chronic atrial fibrillation associated with mitral valve disease, Ann Thorac Surg 1996; 62:17964800]. More recently, Dr. Cox and his group [Nathan H., Eliakim M., The junction between the left atrium and the pulmonary veins, An anatomic study of human hearts, Circulation 1966; 34:412-422, and Cox J. L., Schuessler R. B., Boineau J. P., The development of the Maze procedure for the treatment of atrial fibrillation, Semin Thorac Cardiovasc Surg 2000; 12:2-14] have used cryoprobes (cryo-Maze) to duplicate the essentials of the Cox-Maze III procedure. Other cryo-based devices are described in U.S. Pat. Nos. 6,929,639 and 6,666,858 to Lafontaine and U.S. Pat. No. 6,161,543 to Cox et al.

More recent approaches for the AF treatment involve the use of ultrasound energy. The target tissue of the region surrounding the pulmonary vein is heated with ultrasound energy emitted by one or more ultrasound transducers. One such approach is described by Lesh et al. in U.S. Pat. No. 6,502,576. Here the catheter distal tip portion is equipped with a balloon which contains an ultrasound element. The balloon serves as an anchoring means to secure the tip of the catheter in the pulmonary vein. The balloon portion of the catheter is positioned in the selected pulmonary vein and the balloon is inflated with a fluid which is transparent to ultrasound energy. The transducer emits the ultrasound energy which travels to the target tissue in or near the pulmonary vein and ablates it. The intended therapy is to destroy the electrical conduction path around a pulmonary vein and thereby restore the normal sinus rhythm. The therapy involves the creation of a multiplicity of lesions around individual pulmonary veins as required. The inventors describe various configurations for the energy emitter and the anchoring mechanisms.

Yet another catheter device using ultrasound energy is described by Gentry et al. [Integrated Catheter for 3-D Intracardiac Echocardiography and Ultrasound Ablation, IEEE Transactions on Ultrasonics, Ferroelectrics, and Frequency Control, Vol. 51, No. 7, pp 799-807]. Here the catheter tip is made of an array of ultrasound elements in a grid pattern for the purpose of creating a three dimensional image of the target tissue. An ablating ultrasound transducer is provided which is in the shape of a ring which encircles the imaging grid. The ablating transducer emits a ring of ultrasound energy at 10 MHz frequency. In a separate publication [Medical Device Link, Medical Device and Diagnostic Industry, February 2006], in the description of the device, the authors assert that the pulmonary veins can be imaged and "a doctor would be able to electrically isolate the pulmonary veins by putting a linear lesion around them" (emphasis by inventors). It is unclear from this statement whether the ablation ring is placed around one single target vein, or around a plurality of veins. In the described configuration of the catheter tip, it can be easily seen that the described ring ultrasound energy source can only emit the ultrasound beam of a size to ablate only one pulmonary vein at a time.

Other devices based on ultrasound energy to create circumferential lesions are described in U.S. Pat. Nos. 6,997,925; 6,966,908; 6,964,660: 6,954,977; 6,953,460; 6,652,515; 6,547,788; and U.S. Pat. No. 6,514,249 to Maguire et al.; U.S. Pat. Nos. 6,955,173; 6,052,576; 6,305,378; 6,164,283; and U.S. Pat. No. 6,012,457 to Lesh; U.S. Pat. Nos. 6,872,205; 6,416,511; 6,254,599; 6,245,064; and U.S. Pat. No. 6,024,740; to Lesh et al.; U.S. Pat. Nos. 6,383,151; 6,117,101; and WO 99/02096 to Diederich et al.; U.S. Pat. No. 6,635,054 to Fjield et al.; U.S. Pat. No. 6,780,183 to Jimenez et al.; U.S. Pat. No. 6,605,084 to Acker et al.; U.S. Pat. No. 5,295,484 to Marcus et al.; and WO 2005/117734 to Wong et al.

In all above approaches, the inventions involve the ablation of tissue inside a pulmonary vein or at the location of the ostium. The anchoring mechanisms engage the inside lumen of the target pulmonary vein. In all these approaches, the anchor is placed inside one vein, and the ablation is done one vein at a time.

BRIEF SUMMARY OF THE INVENTION

One aspect of the invention provides a cardiac ablation system including an ablation catheter having an anchor adapted to support the ablation catheter within an atrium of a heart and an ultrasound emitter disposed radially outward from a rotation axis and from the anchor, and a control mechanism adapted to rotate the ultrasound emitter about the rotation axis and to provide ablation energy to the ultrasound emitter to ablate heart tissue. Some embodiments also include an ultrasound emitter support extending radially outward from the rotation axis and supporting the ultrasound emitter, which may be a distal portion of the ablation catheter or may be a separate element.

In some embodiments, the emitter is disposed to emit ultrasound energy through a distal end of the support, and in other embodiments the emitter is disposed to emit ultrasound energy radially outward from a side of the support. In some embodiments, the emitter is disposed at an angle greater than zero with respect to the outer surface of the support.

In some embodiments, the emitter includes an ultrasound transducer and an ultrasound reflective surface disposed to reflect ultrasound energy from the transducer. The transducer may be disposed to direct ultrasound energy proximally toward the reflective surface.

In some embodiments, the control mechanism is adapted to bend the emitter support at a desired angle from the rotation axis. This angle may be formed at a first location along the emitter support, with the control mechanism being further adapted to bend the emitter support at a second location along the emitter support.

In some embodiments, the ultrasound emitter support includes or serves as an electrode in electrical communication with the control mechanism and the anchor includes or serves as an electrode in electrical communication with the control mechanism.

The control mechanism may be adapted to move the anchor within a left atrium. The anchor may extend substantially along the rotation axis, with the ablation catheter being adapted to rotate with respect to the anchor. Alternatively, the anchor may extend along an axis other than the rotation axis. In embodiments in which the system further includes a delivery sheath adapted to contain the ablation catheter, either the delivery sheath or the ablation catheter may have a port through which the anchor extends. Some embodiments also include a second anchor supporting the ablation catheter.

In some embodiments, the emitter is distally and proximally translatable with respect to the anchor. In some embodiments, the emitter is supported by a transducer support extending radially outward from the rotation axis and is distally and proximally translatable with respect to the anchor.

The anchor may be adapted to contact a heart tissue surface, such as the interior wall of the atrium or an interior surface of a pulmonary vein. Some embodiments have a delivery sheath surrounding the ablation catheter, and the anchor is expandable to contact a support catheter surrounding the ablation catheter.

In embodiments in which the ultrasound emitter includes an ultrasound transducer, the system may also include a fluid source and a fluid flow path adjacent to the transducer. The system may also have a fluid exit port adjacent to the transducer and extending from the fluid flow path to the exterior of the ablation catheter. In embodiments in which the ultrasound emitter is disposed proximal to a distal end of the ablation catheter, the ablation catheter may also have a fluid chamber in communication with the fluid source, disposed between the ultrasound emitter and the distal end of the catheter, and in fluid communication with the distal end of the catheter. The fluid chamber may have a plurality of fluid exit channels formed in the distal end of the catheter.

Some embodiments also have a distance sensor adapted to sense distance between the ultrasound emitter and a tissue surface. The ultrasound emitter and the distance sensor may both be an ultrasound transducer. Some embodiments may also have an ablation depth sensor. The ultrasound emitter and ablation depth sensor may both be an ultrasound transducer.

Another aspect of the invention provides a cardiac ablation system including an ablation catheter having an ultrasound emitter and an ultrasound emitter support extending radially outward from a rotation axis and supporting the ultrasound emitter, and a control mechanism adapted to rotate the ultrasound emitter about the rotation axis and to provide ablation energy to the ultrasound emitter to ablate heart tissue and adapted to bend the emitter support at a desired angle from rotation axis. In some embodiments, the desired angle is formed at a first location along the emitter support, the control mechanism being further adapted to bend the emitter support at a second location along the emitter support.

In some embodiments, the ultrasound emitter includes an ultrasound transducer, with the system further comprising a fluid source and a fluid flow path adjacent to the transducer. The system may also include a fluid exit port adjacent to the transducer and extending from the fluid flow path to the exterior of the ablation catheter.

Some embodiments also have a distance sensor adapted to sense distance between the ultrasound emitter and a tissue surface. The ultrasound emitter and the distance sensor may both be an ultrasound transducer. Some embodiments may also have an ablation depth sensor. The ultrasound emitter and ablation depth sensor may both be an ultrasound transducer.

Yet another aspect of the invention provides a cardiac ablation method including the following steps: inserting a treatment catheter into an atrium of a heart, the treatment catheter including an ultrasound emitter; positioning the ultrasound emitter to face heart tissue within the left atrium outside of a pulmonary vein: emitting ultrasound energy from the ultrasound emitter while rotating the ultrasound emitter about a rotation axis; and ablating heart tissue with the ultrasound energy to form a lesion outside of a pulmonary vein. In some embodiments, the positioning step includes the step of bending an ultrasound emitter support. In some embodiments, the positioning step includes the step of moving the ultrasound emitter parallel to the rotation axis. In some embodiments, the positioning step includes the step of anchoring the treatment catheter, such as against the heart wall or by placing an anchor against an atrial wall outside of a pulmonary vein or within a pulmonary vein. The anchoring step may also involve placing a plurality of anchors within a plurality of pulmonary veins and/or expanding an anchor within a support catheter.

In some embodiments, the rotating step includes the step of rotating the treatment catheter about the anchor. The rotation may include the step of rotating the ultrasound emitter less than 360° around the rotation axis or rotating the ultrasound emitter at least 360° around the rotation axis.

In some embodiments, the ablating step includes the step of forming a lesion encircling at least two pulmonary vein ostia. The method may also include forming a second lesion around two other pulmonary vein ostia, possibly forming a third lesion extending from the first lesion to the second lesion, and possibly forming a fourth lesion extending from the first, second or third lesion substantially to a mitral valve annulus.

In some embodiments, the emitting step includes the step of transmitting ultrasound energy distally from a distal end of the treatment catheter and/or radially from the treatment catheter. In some embodiments, the emitting step includes the step of transmitting ultrasound energy from an ultrasound transducer (possibly in a proximal direction) and reflecting the ultrasound energy from a reflector. These embodiments may also include the step of rotating the reflector.

Some embodiments include the step of passing fluid through the ablation catheter and through an exit port adjacent the ultrasound emitter. The fluid may pass into a fluid chamber disposed between the ultrasound emitter and the heart tissue.

Some embodiments include the step of sensing distance between the ultrasound emitter and a tissue surface, such as by using the ultrasound emitter to sense distance between the emitter and the tissue surface. The distance sensing step may include the step of sensing distance between the ultrasound emitter and the tissue surface over an intended ablation path prior to the ablating step and may include the step of repositioning the ultrasound emitter as a result of sensed distance determined in the sensing step.

Some embodiments include the step of sensing depth of ablation in the heart tissue, such as by using the ultrasound emitter to sense depth of ablation in the heart tissue. The speed of rotation of the ultrasound emitter and/or the power delivered to the ultrasound emitter may be based on sensed depth of ablation.

Some embodiments include the step of sensing thickness of the heart tissue. The speed of rotation of the ultrasound emitter and/or the power delivered to the ultrasound emitter may be based on sensed tissue thickness. In some embodiments, the ablating step includes the step of forming a substantially elliptical lesion segment in the heart tissue.

Still another aspect of the invention provides a cardiac ablation method including the following steps: inserting a treatment apparatus into an atrium of a heart, the treatment apparatus having an ultrasound emitter and an ultrasound emitter support; positioning the ultrasound emitter to face heart tissue within the left atrium outside of a pulmonary vein; emitting ultrasound energy from the ultrasound emitter while changing a bend angle in the ultrasound emitter support; and ablating heart tissue with the ultrasound energy to form a lesion outside of a pulmonary vein. In some embodiments, the positioning step includes the step of bending an ultrasound emitter support. In some embodiments, the positioning step includes the step of anchoring the treatment catheter.

Some embodiments add the step of rotating the ultrasound emitter about a rotation axis during the emitting step. In some embodiments, the ablating step includes the step of forming a substantially linear lesion and/or a substantially elliptical lesion segment in the heart tissue.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 3A-C show bending of a distal portion of the catheter of FIG. 1.

FIG. 3D shows bending of the distal end of the catheter of FIG. 1 and an anchor mechanism.

DETAILED DESCRIPTION OF THE INVENTION

The invention described herein includes a device and methods for creating ablation zones in tissue. The device of the invention includes an elongated member (e.g., a catheter) and an anchor mechanism. The elongate member includes a distal tip assembly for directing energy to a tissue. Uses of the invention include but are not limited to providing a conduction block for treatment of atrial fibrillation in a subject, for example, in a patient.

Figure 1:
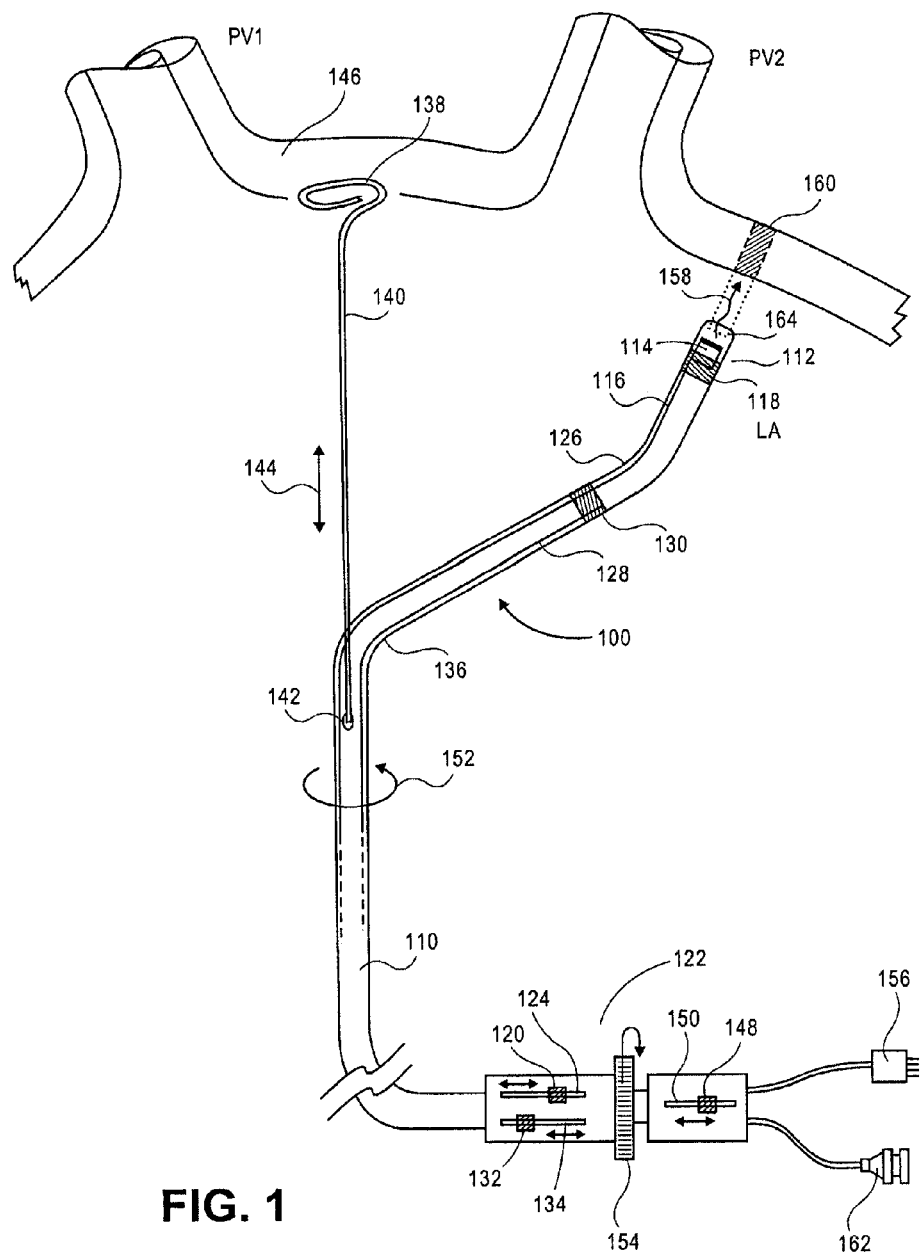
FIG. 1 shows the device including a catheter in one embodiment of the invention.

One aspect of a first embodiment of the invention is shown in FIG. 1. As shown, the device 100 includes an elongate member that can be a catheter 110. In other implementations, the elongate member is a cannula, tube or other elongate structure having one or more lumens. The catheter 110 can be made of a flexible multi-lumen tube. As shown, the catheter 110 can include a distal tip assembly 112 positioned at a distal portion of the catheter 110. The tip assembly 112 can house an energy delivery structure, for example, an ultrasound transducer subassembly 114 (described in more detail in reference to FIG. 4).

Although the ablation device described herein includes a distal tip assembly having an ultrasound transducer as a source of ablation energy, it is envisioned than any of a number of energy sources can be used with various implementations of the invention. Suitable sources of ablation energy include but are not limited to, radio frequency (RF) energy, microwaves, photonic energy, and thermal energy. It is envisioned that ablation could alternatively be achieved using cooled fluids (e.g., cryogenic fluid). Additionally, although use of a single ultrasound transducer is described herein as an exemplary energy delivery structure, it is envisioned that a plurality of energy delivery structures, including the alternative energy delivery structures described herein, can be included in the distal portion of the elongate member. In one implementation the elongate member is a catheter wherein the distal portion of the catheter includes multiple energy delivery structures, for example, multiple ultrasound transducers. Such a catheter distal portion can be deployable as a loop or other shape or arrangement to provide positioning of one or more of the energy delivery structures for a desired energy delivery.

The elongate member of the device can include a bending mechanism for bending a distal portion of the elongate member (e.g., a catheter) at various locations (an example of such bending is shown in FIGS. 3A-D). The bending mechanism can include but is not limited to lengths of wires, ribbons, cables, lines, fibers, filament or any other tensional member. In one implementation the bending mechanism includes one or more pull wires, for example, a distal pull wire and a proximal pull wire. A variety of attachment elements for connecting the bending mechanism and the elongate member are envisioned. As shown in FIG. 1, in one implementation where the elongate member is a catheter 110, the distal pull wire 116 and the transducer subassembly 114 are secured to the tip assembly 112 by means of a distal adhesive band 118. Other means of attaching the distal pull wire 116 to a portion of the tip assembly 112 include but are not limited to attachment using: adhesive, welding, pins and/or screws or the likes. Pull wire 116 can be contained in a lumen (not shown) of the catheter 110 and can terminate at a slider 120 in a proximal housing 122. The proximal housing 122 can include various actuating mechanisms to effect various features of the catheter, as described below. In one implementation, the slider 120 can move in a slot 124 which pulls or pushes the wire 116. Since the distal end of the wire 116 is secured to the tip 112, the result is that the catheter tip 112 can be bent and unbent as desired at a distal bend location 126 by moving the slider 120. Distal bend location 126 can be positioned on the distal tip assembly 112 as needed to achieve the desired bending of the catheter 110.

A second analogous bending mechanism can be provided in the catheter which is more proximally positioned with respect to the distal tip assembly. As shown in FIG. 1, a proximal pull wire 128 can reside in a lumen (not shown) of the catheter 110 and the wire 128 distal end can be secured in the catheter 110 by a proximal adhesive band 130. This proximal pull wire 128 can terminate in a second slider 132 at the proximal housing 122. The slider 132 can move in a second slot 134 which allows the distal tip assembly 112 to be bent at a proximal bend location 136.

The elongate member can further include an anchor mechanism by which the distal portion of the elongate member can be held in a relatively predictable position relative to a tissue, for example, inside a chamber such as the left atrium of the heart. As shown in FIG. 1, in one implementation an anchor mechanism 140 includes a pre-shaped wire loop 138. In a specific implementation, the wire loop 138 is made of a shapeable wire, for example, made from a shape-memory material such as Nitinol (nickel-titanium alloy). Alternatively, the anchor mechanism can include a loop made from any of a number of materials such as metal, plastic and/or fiber or combinations thereof. Although a loop is described, it is envisioned that any of a number of shapes, curved and/or angular, two-dimensional and/or three-dimensional can provide the anchoring required. The anchor 140 can reside in a lumen (not shown) of the catheter 110, and can exit from the catheter 110 through a notch 142 near the distal end of the catheter 110 (see FIG. 1). The proximal end of the anchor mechanism 140 can terminate in a third slider 148 at the proximal housing 122. The third slider 148 can move in a third slot 150 at the proximal housing 122, thereby producing a corresponding anchor mechanism movement 144 of the anchor mechanism 140.

In one implementation, when the slider 148 is in a proximal position, the wire loop 138 can be maintained in a substantially linear shape inside the lumen of the catheter 110 (not shown). In use, as third slider 148 is advanced distally in the slot 150, a distal tip of the wire loop 138 exits the notch 142 (not shown). As the slider 148 is further advanced, the wire loop 138 can take on the shape of a pre-formed loop as it is unrestricted by the confines of a lumen (see FIG. 3D). As shown in FIG. 1, the wire loop 138 of the anchor 140 can be advanced further until it makes a firm contact with the tissue such as the ceiling wall 146 of the left atrium of the heart. One function of the wire loop 138 is to provide a firm contact and/or stabilization between the anchor mechanism 140 and the tissue, and thereby between a region of the catheter 110 and the tissue (see FIG. 1). An additional function of the anchor mechanism is to provide an axis around which all or a portion of the catheter shaft can be rotated. Such rotation of the catheter is illustrated in FIG. 1, as arrow 152. As shown in FIG. 1, in one implementation a rotation mechanism 154, for example, a wheel, is provided at the proximal housing 122 by which all or a portion of the catheter 110 shaft can be rotated around the axis defined by the anchor mechanism 140. As can be easily envisioned, through rotational movement about such an axis, the most distal portion of the tip assembly 112 can be swept in a desired path in relation to target tissue. In one implementation, the path of the tip assembly 212 can be a substantially circular path 262 inside a tissue chamber such as the left atrium of the heart (see FIG. 11).

A transducer subassembly can be secured in the distal tip assembly of the catheter. As shown in FIG. 1, in one implementation a transducer subassembly 114 is secured by the distal adhesive band 118. The transducer subassembly is described in more detail herein for various embodiments of the invention. In one implementation, the transducer subassembly 114 includes a temperature measuring device such as a thermistor or a thermocouple (not shown). The transducer can be energized by the wires which, along with the temperature sensor wires, can be contained in a lumen of the catheter (not shown). As shown in FIG. 1, such wires can terminate in a connector, for example, a transducer connector 156 at the proximal housing 122. The connector 156 can be attached to and detached from a power generator and/or controller (not shown). It is envisioned that such a power generator and/or controller can energize the transducer, display temperature readings and perform any of a number of functions relating to such transducers as well understood in the art. For example, monitoring A-mode signal and the like (e.g., B-mode). In use, as the transducer is energized, it can emit an ultrasound beam 158 towards the tissue 146. As the energy is transferred from the ultrasound beam into the tissue, the targeted tissue portion can be heated sufficiently to achieve ablation. Thus, as shown in FIG. 1, an ablation zone 160 can be created in the tissue.

During the energizing of the transducer, the transducer may become heated. It is envisioned that the transducer can be maintained within a safe operating temperature range by cooling the transducer. In one implementation cooling of the transducer can be accomplished by contacting the transducer subassembly with a fluid, for example, saline. In some implementations the transducer can be cooled using a fluid having a lower temperature relative to the temperature of the transducer. In one implementation a fluid for cooling the transducer is flushed past the transducer subassembly from a lumen in the catheter (see e.g., FIG. 2). Accordingly, as shown in FIG. 1, the proximal end of a lumen of the catheter 110 can be connected to a fluid port 162, for example, a luer fitting, in the proximal housing 122. As further shown in FIG. 1, in one implementation fluid used for cooling the transducer can exit the catheter tip 112 through a one or more apertures 164. The apertures can be a grating, screen, holes, weeping structure or any of a number of suitable apertures. In one implementation apertures 164 are drip holes.

Figure 2:
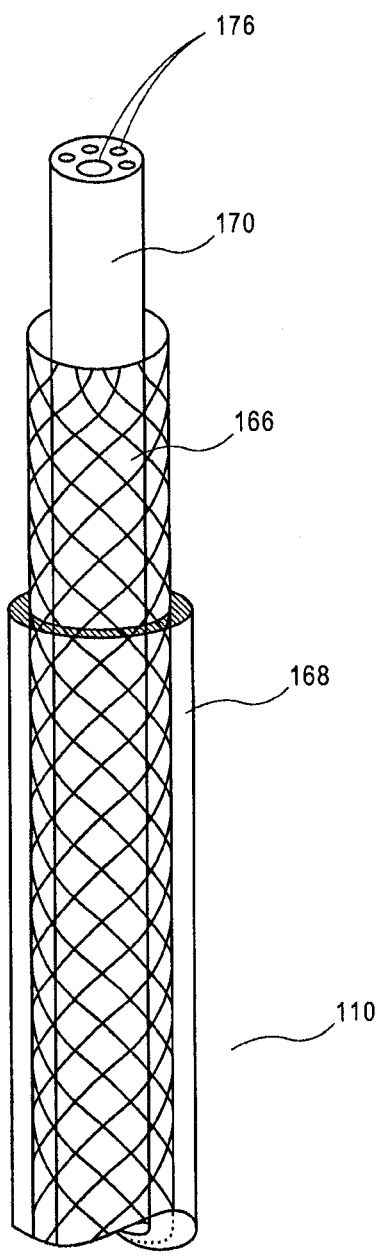
FIG. 2 shows the construction of the shaft of the catheter in one embodiment of the invention.

Referring to FIG. 2, in one implementation where the elongate member of the device is a catheter, the shaft of the catheter 110 includes a multilumen tubing 170 having one or more lumens 176, which is encased in a braid 166 of suitable metallic or non-metallic filaments and is encased in a smooth jacket 168 made of conventional biocompatible material. Lumens 176 can accommodate any of a number of features of the invention including but not limited to, pull wires, fluids, gases, and electrical connections.

In FIGS. 3A-C, an exemplary series of drawings illustrate bending of the catheter distal portion in more detail. In the implementation shown, the distal pull wire 116 is secured at a distal portion of the tip assembly 112 by means of the distal adhesive band 118. In use, as the distal pull wire 116 is pulled by moving the first slider 120 (see FIG. 1), the catheter distal portion is bent at location 126 in the direction 172, thereby moving from position X to position Y, as shown in FIG. 313. Next, the proximal pull wire 128, which is secured in the catheter lumen at a position by proximal adhesive band 130, is pulled by moving the second slider 132 (see FIG. 1). This results in the catheter 110 distal portion bending at location 136 and moving in the direction 174 to position Z, away from the longitudinal axis of the catheter, as shown FIG. 3C.

It is envisioned that the pull wire attachment points, and correspondingly the bend locations in the device can be configured, in any of a number of ways, not limited to the examples described herein. For example, it is envisioned that a single pull wire or other bend inducing mechanism can be used. Alternatively, the use of three or more such mechanism is envisioned. With respect to attachment points for bend inducing mechanism, it is envisioned that any location along the distal tip assembly as well as the catheter distal portion are suitable optional attachment points. With respect to the number and location of bend locations in the device, it is envisioned that a spectrum of suitable bend locations can be provided. For example, while one and two bends are illustrated herein, it is envisioned that three or more bends can be used to achieve a desired catheter configuration and/or application of energy using the device.

The anchor mechanism 140 of the device can be deployed in a separate or simultaneous step from bending the device, as shown in FIG. 3D. The anchor mechanism 140, which can be configured to reside in a lumen (not shown) of the catheter 110, is advanced out of the catheter 110 and through the anchor notch 142 by moving the third slider 148 (see FIG. 1). In the implementation shown in FIG. 3D, as the anchor mechanism 140 exits the notch 142 a distal portion of the mechanism 140 takes on the pre-formed shape of a loop 138. This loop 138 is advanced further in axial direction 144 until it firmly engages tissue, for example in the inside wall of a tissue chamber such as the left atrium of the heart. The anchor mechanism provides a rotational axis for the distal tip assembly. The transducer subassembly 114 can be intentionally displaced away from this axis so that when the catheter shaft is rotated (see arrow 152) around the axis provided by the anchor mechanism 140, the transducer can traverse a substantially circular loop inside the tissue chamber. The result of this motion is to create a substantially circular ablation zone inside the tissue chamber (described in more detail in FIG. 11). It is envisioned that an arc-shaped or other curved ablation zone could alternatively be created with the device.

Figure 4:
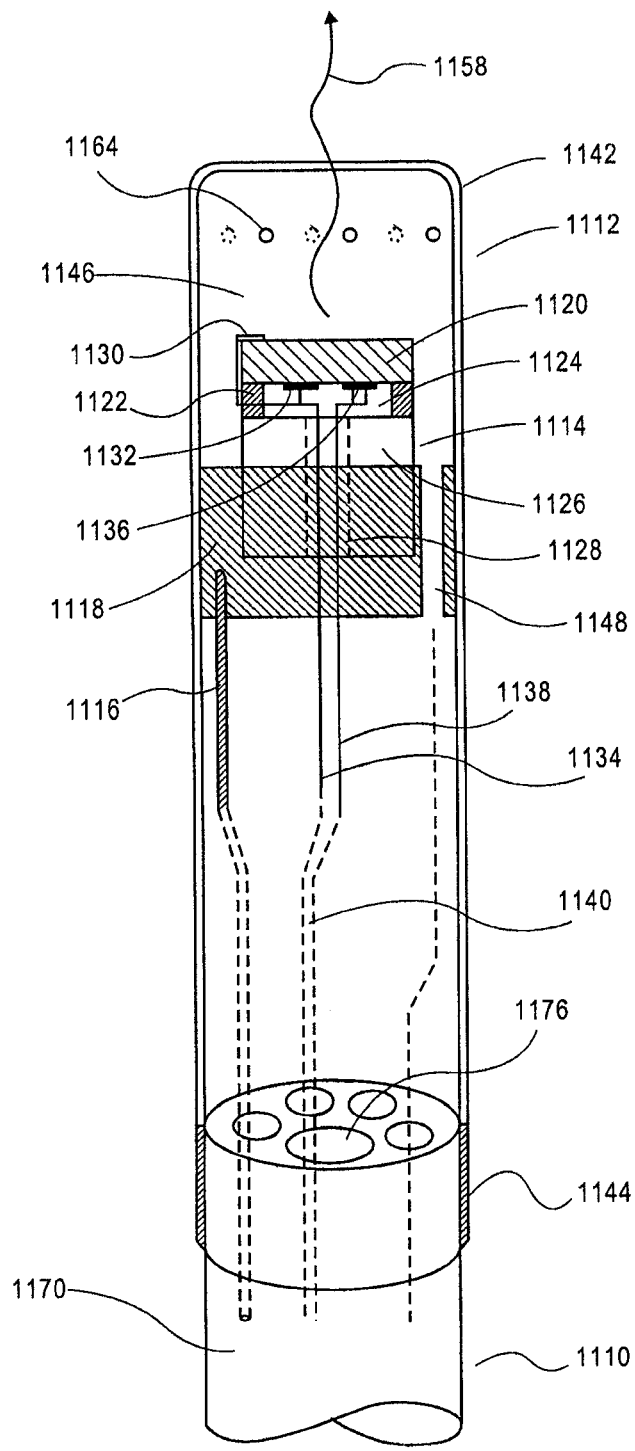
FIG. 4 shows the distal tip assembly of the catheter of FIG. 1.

The design of the distal tip subassembly can include a variety of configurations providing alternative means of delivering energy to tissue. A first embodiment of the distal tip subassembly 1112 is shown in FIG. 4. As illustrated, the tip assembly 1112 can include a closed end tube casing 1142 which is transparent to ultrasound waves. It can further contain a transducer subassembly 1114 including an ultrasound transducer 1120. The transducer 1120 can be made of a piezo-electric material such as PZT (lead zirconate titanate) or PVDF (polyvinylidine difluoride) and the like. The transducer 1120 can be configured as a disc and the faces of the disc can be coated with a thin layer of a metal such as gold. In one implementation the disc is a circular flat disc. Other suitable transducer coating metals include but are not limited to stainless steel, nickel-cadmium, silver or a metal alloy. As shown in FIG. 4, in one implementation the transducer 1120 can be connected to electrical attachments 1130 and 1132 at two opposite faces. These connections can be made of insulated wires 1134 which can be, for example, a twisted pair or a coaxial cable so as to minimize electromagnetic interference. When a voltage is applied across the transducer, ultrasonic sound beam 1158 is emitted. The frequency of the ultrasound beam is in the range of about 1 to 50 megaHertz.

As shown in FIG. 4, a temperature sensor 1136 can be coupled with the transducer 1120, for example, attached to the back face of the transducer 1120. The temperature sensor can be comprised of a thermocouple or a thermistor or any other suitable means. As shown in FIG. 4, the sensor 1136 can include wires 1138 which carry the temperature information to the catheter proximal end. The wires 1134 and 1138 together can form a wire bundle 1140 extending to the catheter proximal end.

As further shown in FIG. 4, the transducer 1120 can be attached to a backing 1126 by means of an adhesive ring 1122 or other attachment, which creates a void or pocket 1124 between the transducer 1120 and the backing 1126. The pocket 1124 can include a material which efficiently reflects sound waves generated by the transducer 1120. The material of the pocket 1124 can be air or any other suitable material such as metal or plastic which reflects the sound waves. Advantageously, the sound waves thus can be directed to exit from the front face of the transducer, resulting in a minimum amount of sound energy lost out through the transducer back face into the backing. The backing can be made of a thermally conductive material such as metal or plastic for aiding in the dissipation of heat which is created when the transducer is energized.

As illustrated in FIG. 4, the wire bundle 1140 can be fed through a passageway or hole 1128 in the backing 1126 and can be housed in a lumen of the catheter 1110. The wire bundle can terminate in the connector 156 at the proximal housing 122 (see FIG. 1). As shown in FIG. 4, the proximal end of the backing 1126 can be secured to the casing 1142 by means of the distal adhesive band 1118. This creates a void or chamber 1146 between the distal end of the casing 1142 and the distal adhesive band 1118. The chamber 1146 is configured to be filled with a thermally conductive fluid such as saline so that the transducer 1120 can be cooled while energized. The distal adhesive band 1118 can include a passageway 1148 which is used in connecting the chamber 1146 to a fluid carrying lumen. The passageway 1148 can be in fluid communication with the fluid port 162 at the proximal housing 122 through one of the lumens (not shown) of the catheter 1110 (see FIGS. 1 and 4). As shown in FIG. 4, the chamber 1146 can include one or more apertures 1164, for example, drip holes distributed circumferentially at the chamber 1146 distal portion. In use, prior to insertion of the device into the body, the chamber can be filled with a fluid such as saline. This can be accomplished using a suitable fluid supply device such as a syringe connected to the fluid port (not shown). The fluid from the syringe can flow through the passageway of the distal adhesive band, into the chamber while expelling the air out from the chamber through the apertures. During the use of the device in the body, a constant drip of saline can be maintained, if necessary, to cool the transducer.

Still referring to FIG. 4, a distal pull wire 1116 can be secured to the distal tip subassembly 1112 by the distal adhesive band 1118. The distal pull wire 1116 can reside in one of the lumens 1176 of the catheter 1110 and can be connected to the slider 120 in the proximal housing 122 (see FIG. 1 and FIG. 4). As described above in reference to FIG. 3A, the distal pull wire 1116 can be utilized in bending the distal portion of the catheter 1110. As shown in FIG. 4, the distal tip subassembly 1112 can be securely attached to the catheter tubing 1170 of the catheter 1110 by the proximal adhesive band 1144. As further shown in FIG. 4, lumens 1176 of the catheter tubing 1170 can be utilized for passage of various elements of the tip subassembly 1112 and any of their related features, in addition to instruments, gases, fluids, or other substances.

Figure 5:
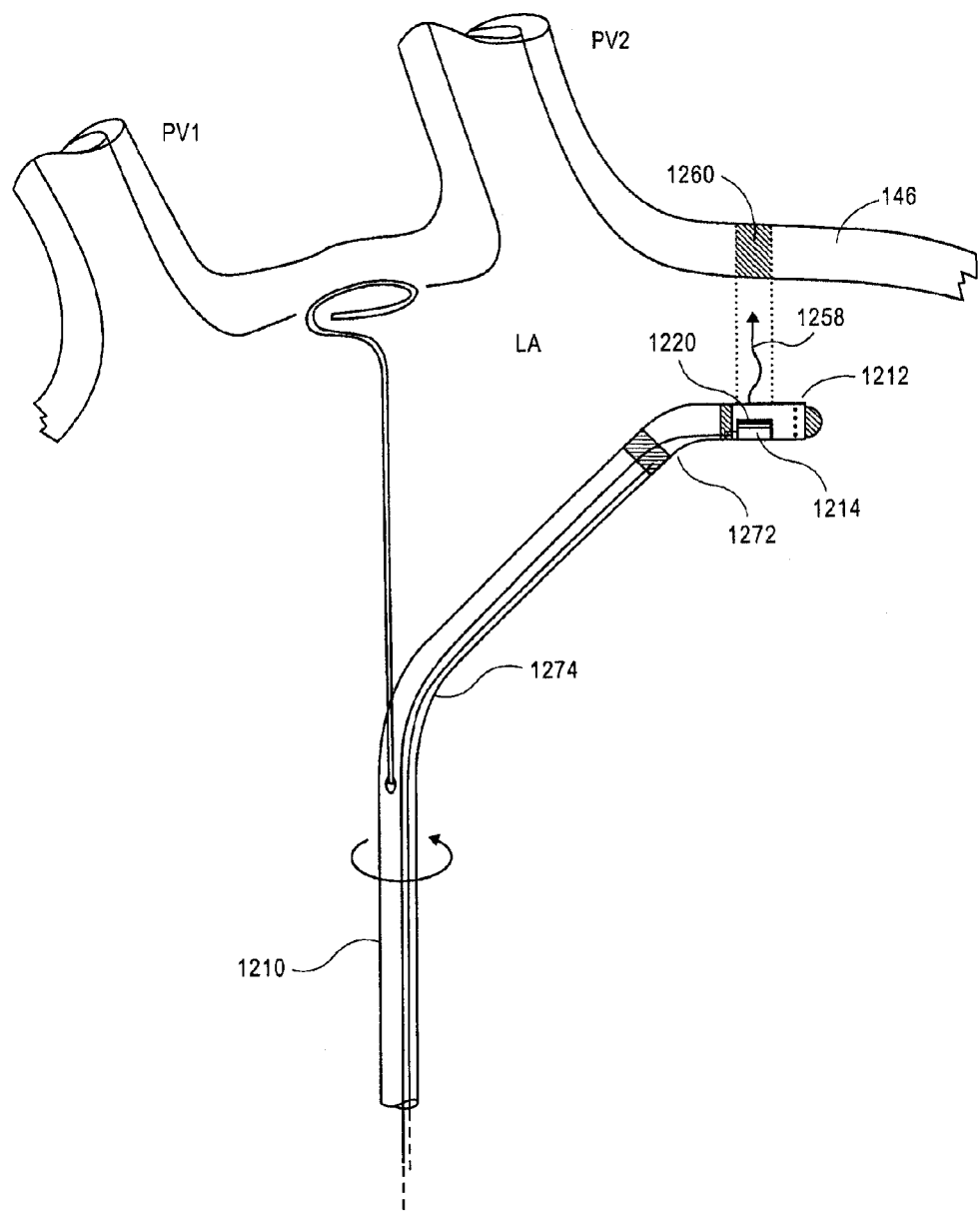
FIG. 5 is a view of the device in a second embodiment.

A second embodiment of the invention including an alternative distal tip assembly arrangement is shown in FIG. 5. Here the transducer subassembly 1214 is mounted in the distal tip assembly 1212 such that the ultrasound transducer 1220 face is substantially parallel to the longitudinal axis of the catheter 1210 (that is to say the longitudinal axis of the catheter 1210 before bending the distal tip assembly 1212 or catheter 1210). In this configuration, the sound beam 1258 exits from a lateral surface of the tip assembly 1212. The construction of the catheter in this configuration can be essentially same as that described herein for the first embodiment (see FIGS. 1-4).

Figure 6:
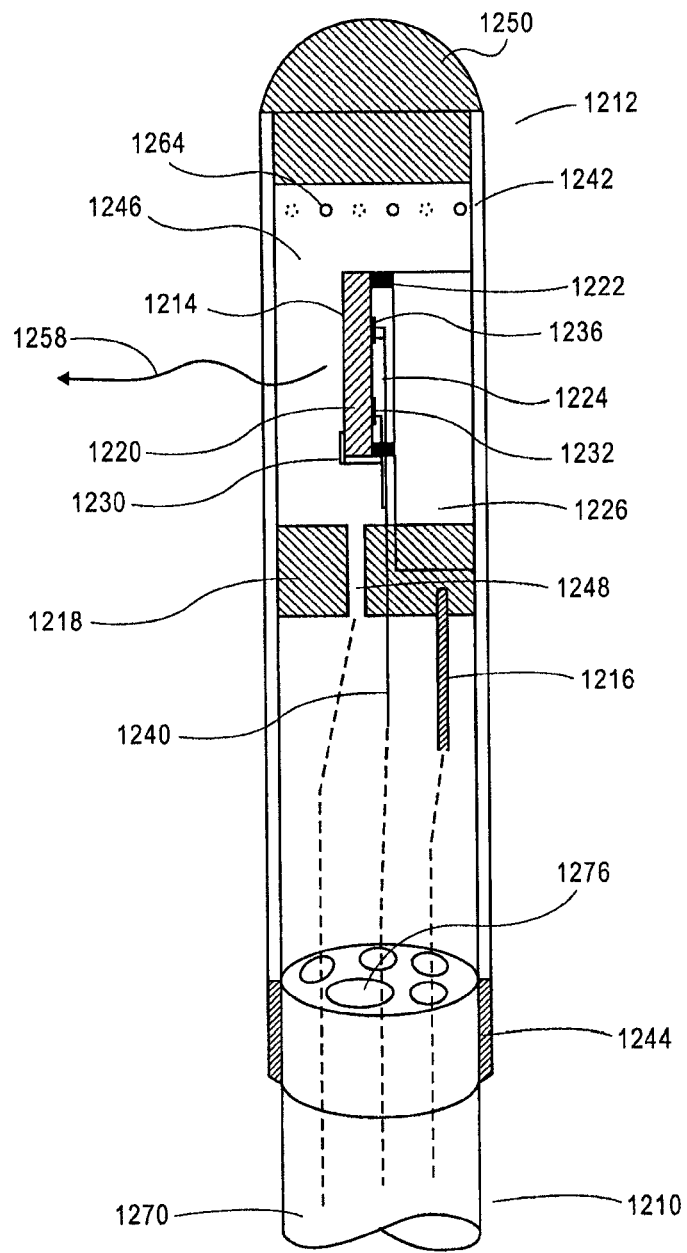
FIG. 6 shows the distal tip assembly of the catheter of FIG. 5.

As shown in FIG. 5, the distal tip assembly 1212 and catheter 1210 bend points, distal bend location 1272 and proximal bend location 1274 respectively, can be arranged and configured such that the ultrasound beam 1258 is presented to the tissue 146 in a substantially right angle from the catheter 1210 longitudinal axis. In this manner an ablation zone 1260 is produced laterally through the tip assembly 1212. FIG. 6 shows details of the distal tip assembly 1212 for this embodiment. As illustrated, the tip assembly 1212 can be assembled in a tube 1242 which is substantially transparent to the ultrasound waves 1258. The transducer subassembly 1214 can include a transducer 1220 which has electrical connections 1230 and 1232 on opposite flat faces. As discussed herein, the transducer 1220 can include a temperature sensor 1236 on, for example, a back side which has wire connections. The transducer wires and the temperature sensor wires together form a bundle 1240 which resides in a lumen 1276 of the catheter tubing 1270.

Still referring to FIG. 6, the distal end of the tube housing 1242 can be sealed. As shown in FIG. 6, in one implementation the distal end is sealed with a thermally conductive adhesive 1250. The back side of the transducer subassembly 1214 can be secured to an adhesive ring 1222 that is connected to a backing 1226. Thus, a void or pocket 1224 is created between the transducer 1220 and the backing 1226. As shown in FIG. 6, the backing 1226 can be secured to the inner wall of the tube 1242, for example, by the distal adhesive band 1218. There can be a passageway 1248 in the adhesive band 1218 to allow the flow of a fluid such as saline to be introduced into the chamber 1246. The passageway 1248 can be in fluid communication with the fluid port 162 at the proximal housing 122 of the catheter 1210 (see FIGS. 1 and 6). As discussed herein the chamber 1246 can include a number of apertures 1264, for example, drip holes distributed circumferentially at the chamber 1246 distal end. As further described herein, prior to insertion of the device into the body, the chamber 1246 can be filled with a fluid such as saline. In addition, during the use of the device in the body, a constant drip of saline can be maintained, as required to cool the transducer 1220.

Again referring to FIG. 6, a distal pull wire 1216 can be secured to the distal tip subassembly 1212 by the distal adhesive band 1218. The distal pull wire 1216 can reside in one of the lumens 1276 of the catheter 1210 and can be connected to the slider 120 in the proximal housing 122 (see FIG. 1 and FIG. 6). As described above in reference to FIG. 3A, the distal pull wire 1216 can be utilized in bending the distal portion of the catheter 1210. As shown in FIG. 6, the distal tip subassembly 1212 can be securely attached to the catheter tubing 1270 of the catheter 1210 by the proximal adhesive band 1244. As further shown in FIG. 6, lumens 1276 of the catheter tubing 1270 can be utilized for passage of various elements of the tip subassembly 1212 and any of their related features, in addition to instruments, gases, fluids, or other substances.

Figure 7:
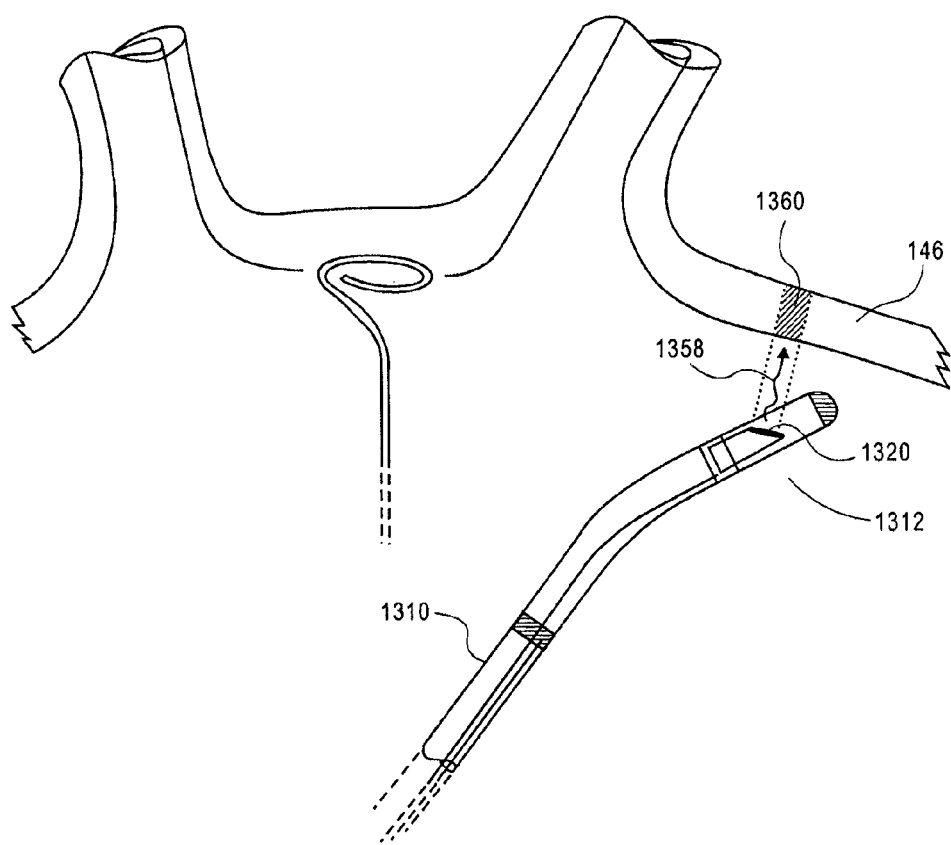
FIG. 7 is a view of the device in a third embodiment.
Figure 8:
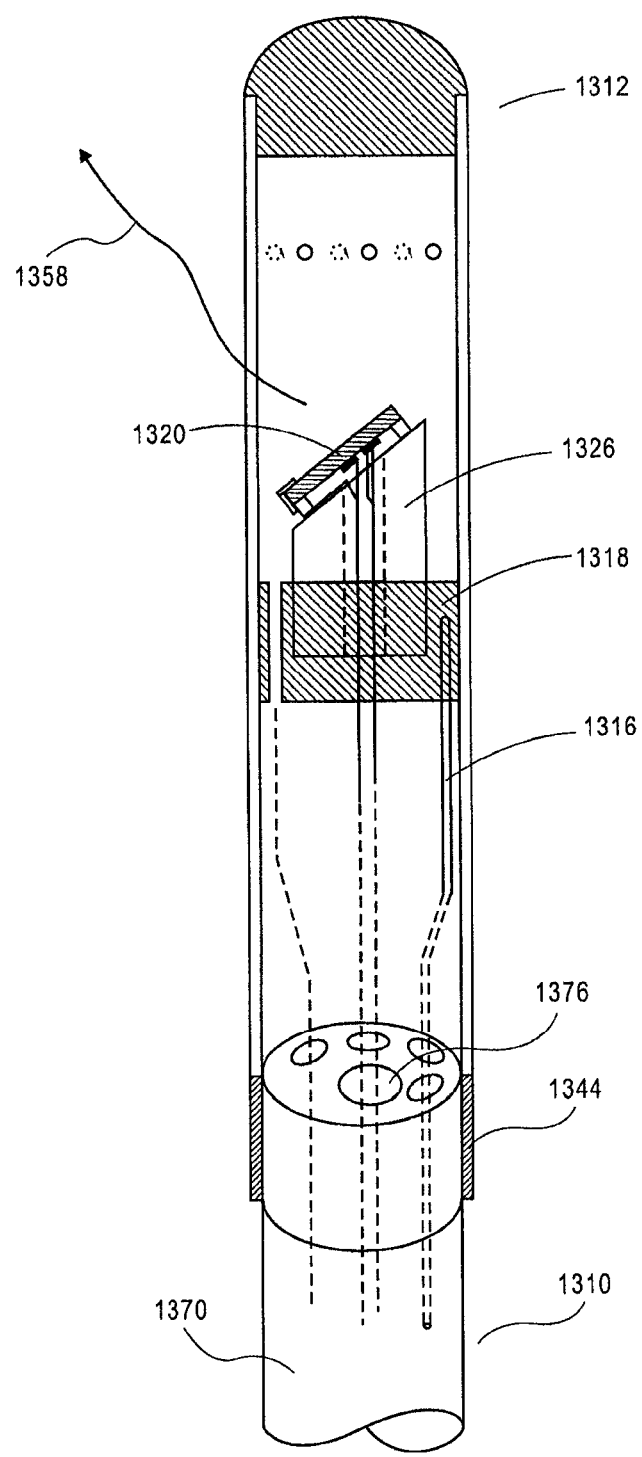
FIG. 8 shows the distal tip assembly of the catheter of FIG. 7.

A third embodiment of the invention including an alternative distal tip assembly arrangement is shown in FIG. 7. Various details, features and uses of this embodiment include those as described herein regarding other embodiments. In this embodiment an alternative transducer subassembly is provided as shown in detail in FIG. 8. As shown in FIG. 8, the ultrasound transducer 1320 can be mounted on an angled backing 1326. The angle of the backing can range between substantially 0-90°. In one implementation the angle is substantially 10-80°. In another implementation the angle is substantially 30-60°. In another implementation the angle is substantially 40-50°. In a further embodiment the angle is substantially 45°. The transducer can include a shape. In one implementation the transducer is in the shape of an elliptical disc. In another implementation the transducer has a rectangular shape. As shown in FIGS. 7 and 8, in one implementation the transducer 1320 can emit energy in the form of an ultrasound beam 1358 at an angle to the longitudinal axis of the catheter 1310. As shown in FIG. 7, the ultrasound beam 1358 can be directed to the tissue 146 by appropriately bending the distal tip assembly 1312 using, for example, pull wires as described herein. The ultrasound energy beam 1358 can create an ablation zone 1360 in the tissue 146. Cooling of the transducer in this implementation can be achieved as described herein.

As shown in FIG. 8 the angled backing 1326 can be secured in the distal tip assembly 1312 by the distal adhesive band 1318. It is envisioned that other means of securing the backing to the distal tip assembly can include but are not limited to attachment using: adhesive, welding, pins and/or screws or the likes. Still referring to FIG. 8, a distal pull wire 1316 can be secured to the distal tip subassembly 1312 by the distal adhesive band 1318. The distal pull wire 1316 can reside in one of the lumens 1376 of the catheter 1310 and can be connected to the slider 120 in the proximal housing 122 (see FIG. 1 and FIG. 8). As described above in reference to FIG. 3A, the distal pull wire 1316 can be utilized in bending the distal portion of the catheter 1310. As shown in FIG. 8, the distal tip subassembly 1312 can be securely attached to the catheter tubing 1370 of the catheter 1310 by the proximal adhesive band 1344. As further shown in FIG. 8, lumens 1376 of the catheter tubing 1370 can be utilized for passage of various elements of the tip subassembly 1312 and any of their related features, in addition to instruments, gases, fluids, or other substances.

Figure 9:
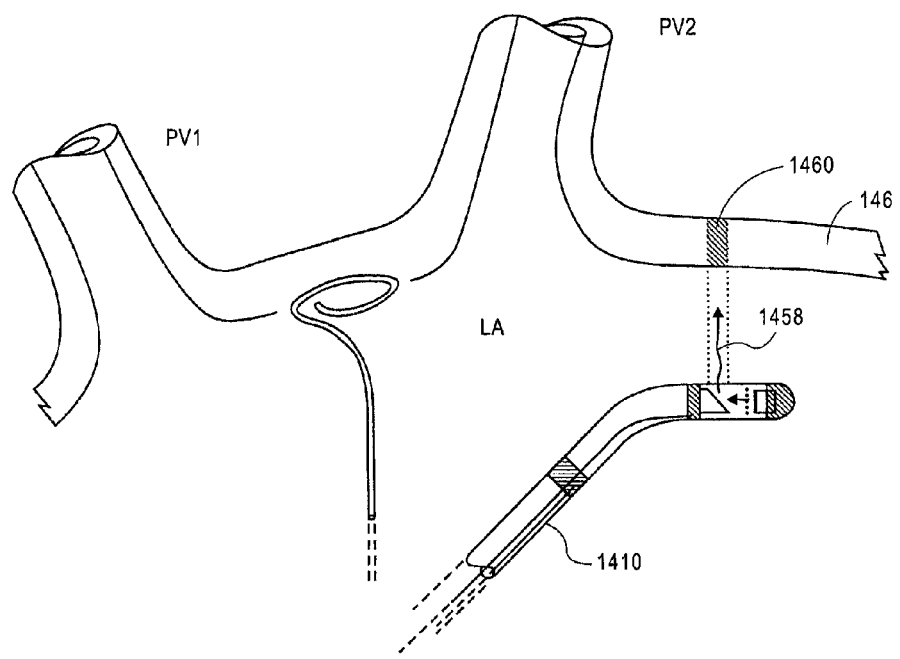
FIG. 9 is a view of the device in a fourth embodiment.
Figure 10:
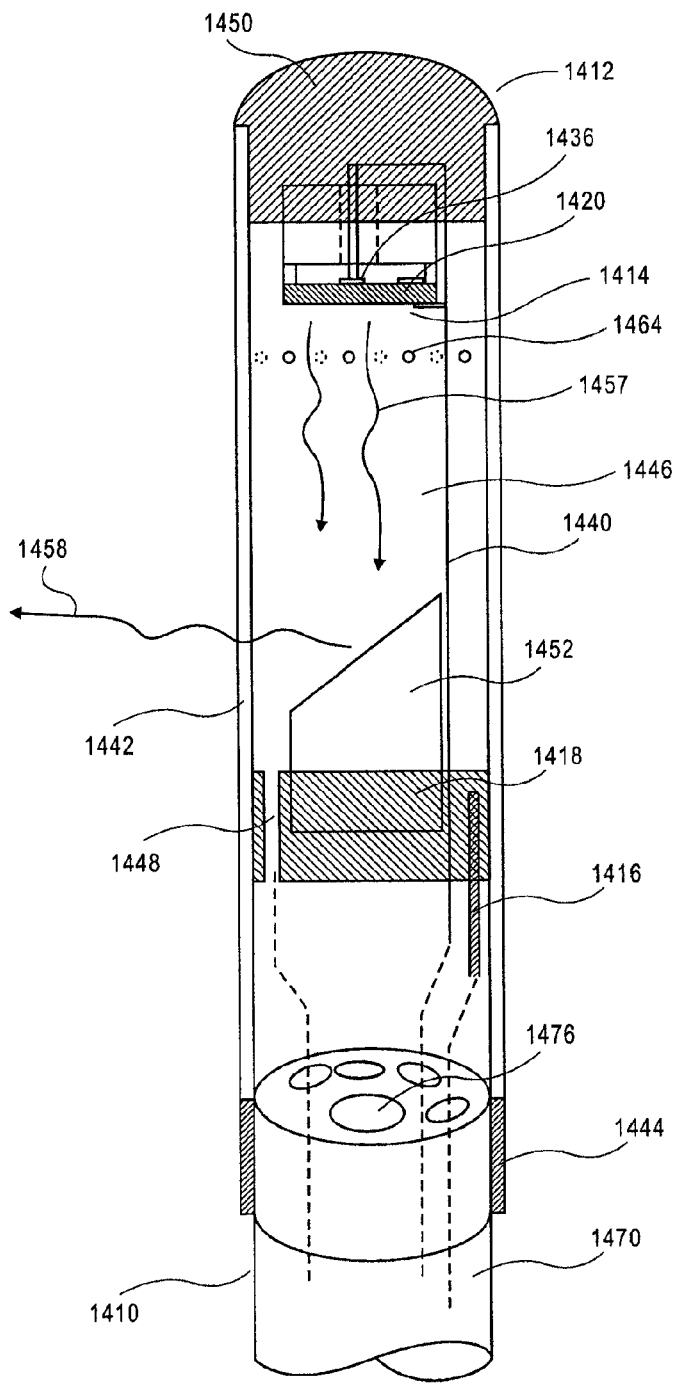
FIG. 10 shows the distal tip assembly of the catheter of FIG. 9.

A fourth embodiment of the invention including an alternative distal tip assembly arrangement is shown in FIG. 9, and the details of the tip assembly are shown in FIG. 10. Various details, features and uses of this embodiment include those as described herein regarding other embodiments. In this embodiment an alternative transducer subassembly is provided as shown in detail FIG. 10. As shown in FIG. 10, in this implementation, the ultrasound transducer 1420 is mounted at a distal portion of the distal tip assembly 1412. Further, the transducer 1420 is directed substantially toward the proximal direction. As illustrated, in this orientation the transducer 1420 can emit an ultrasound wave 1457 substantially parallel to the longitudinal axis of the distal tip assembly 1412.

As shown in FIG. 10, proximal to the transducer 1420 an angled reflector device can be mounted. For example, the reflector device can be a cylindrical reflector 1452 with having a face cut at an angle to the distal tip assembly 1412 longitudinal axis. The reflector 1452 can be arranged to reflect the ultrasound energy wave 1457 produced by the transducer 1420 as an outgoing ultrasound wave 1458 which exits the tubing 1442 and travels to the intended ablation site 1460 in the tissue 146. It is envisioned that the reflector can alternatively include a non-planar face, for example, a curved, convex or concave surface. The angle of the reflector can range between substantially 0-90°. In one implementation the angle is substantially 10-80°. In another implementation the angle is substantially 30-60°. In another implementation the angle is substantially 40-50°. In a further embodiment the angle is substantially 45°.

The reflector 1452 can be secured to the tubing 1442 by means of the distal adhesive band 1418 which can also secure the distal pull wire 1416. The adhesive band 1418 can include a passageway 1448 for the flow of a cooling fluid as describe herein. The transducer subassembly 1414 can be secured at the distal portion of the tip assembly 1412 by means of thermally conductive adhesive 1450 which, together with the adhesive band 1418 forms a chamber 1446. The chamber 1446 can include one or more apertures 1464. As shown in FIG. 10, in one implementation the apertures 1464 are drip holes distributed circumferentially about the distal portion of the distal tip assembly 1412.

In use, a cooling fluid can be flowed from the passageway 1448 in the distal adhesive band, past the reflector 1452 and exit by way of the apertures 1464. This fluid flow can serve to cool the transducer 1420 and keep it within nominal operating temperatures. It is envisioned that cooling of the transducer can be controlled to provide nominal transducer operation. As shown in FIG. 10, the transducer 1420 can include a temperature sensor 1436, for example, attached to the back side of the transducer. The temperature sensor 1436 can include associated lead wires, which along with the wires for the transducer can form a bundle 1440 which is subsequently contained in a lumen 1476 of the catheter tube 1470. Similarly, the fluid passageway 1448 can be in fluid communication with a lumen 1476 of the catheter tubing 1470. As further shown in FIG. 10, the distal pull wire 1416 can also be contained in a lumen 1476 of the catheter tubing 1470. As shown in FIG. 10, in one implementation tubing 1442 is bonded to the catheter tubing 1470 by means of proximal adhesive band 1444.

Still referring to FIG. 10, a distal pull wire 1416 can be secured to the distal tip subassembly 1412 by the distal adhesive band 1418. The distal pull wire 1416 can reside in one of the lumens 1476 of the catheter 1410 and can be connected to the slider 120 in the proximal housing 122 (see FIG. 1 and FIG. 10). As described above in reference to FIG. 3A, the distal pull wire 1416 can be utilized in bending the distal portion of the catheter 1410. As shown in FIG. 10, the distal tip subassembly 1412 can be securely attached to the catheter tubing 1470 of the catheter 1410 by the proximal adhesive band 1444. As further shown in FIG. 10, lumens 1476 of the catheter tubing 1470 can be utilized for passage of various elements of the tip subassembly 1412 and any of their related features, in addition to instruments, gases, fluids, or other substances.

Figure 14:
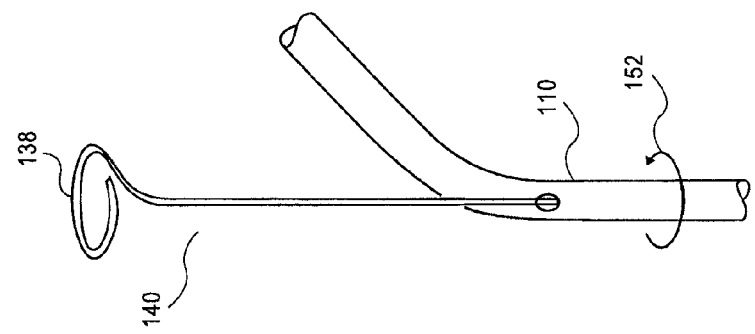

The anchoring mechanism of the device can be configured in any of a number ways in addition to the mechanism as illustrated, for example in FIGS. 3 and 14 wherein a wire loop is included. One function of the anchor mechanism is to provide a firm axis of rotation to the catheter as it is rotated so that the ultrasound beam can be directed to provide a partial or complete zone of ablation. Another function of the anchor mechanism in some implementations is to provide stabilization of the catheter when manipulating the catheter distal portion. As shown in FIG. 14 the anchor mechanism 140 can include a wire loop 138 that can be firmly pressed against the ceiling wall of a heart chamber.

Figure 15:
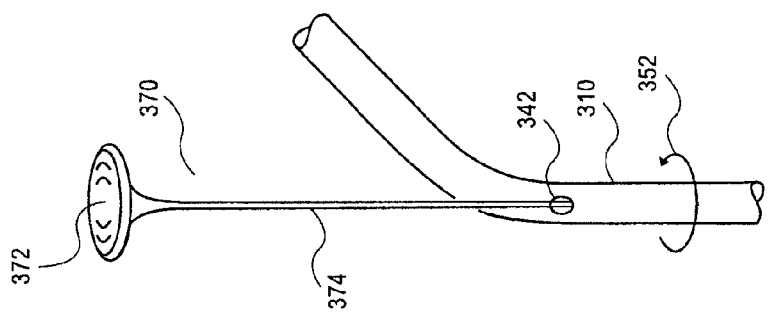

As shown in FIG. 15, in another implementation anchor mechanism 370 including an expandable member, for example, an inflatable balloon is provided. The anchoring member can be in the shape of a disc 372 that is inflatable, for example, an inflatable balloon. The shaft of the anchor mechanism 370 in this case can be made of a suitable tubing 374 for inflating and deflating the disc 372. The disc can be constructed such that when in a deflated profile, the disc can move through an assigned lumen in the catheter (not shown). In use, the device is placed in a heart chamber as described herein. The implementation of the anchor member 374 illustrated in FIG. 15 can be advanced beyond the notch 342, and after deployment the disc 372 can be inflated. The inflated disc can be firmly pressed against the ceiling wall of the heart chamber (not shown). The shaft 374 of the anchor mechanism 370 in this implementation provides an axis of catheter rotation 352 around which the distal tip assembly can be rotated to sweep the ultrasound energy beam to create a zone of ablation. Anchor mechanism 370 shown in FIG. 15 can be withdrawn into the catheter by deflating the disc and pulling the anchor mechanism 370 proximally into the lumen through the notch 342, for example, by actuating a slider mechanism provided at the proximal housing of the catheter.

Although the disc 372 of this anchor mechanism 370 implementation is described as a balloon (see FIG. 15), it is envisioned that any type of expandable member could be used. Suitable expandable members can include but are not limited to a cage, stent, or other self-expanding device that can be deployed and collapsed as required. Such structures are well known in the art.

Figure 16:
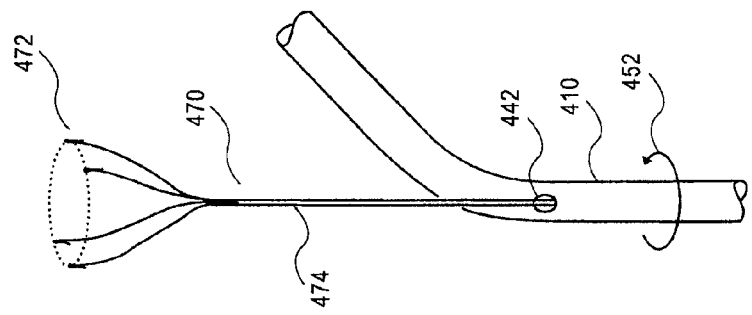
FIGS. 14 to 17 show various mechanisms for the anchoring a portion of the catheter.

Another implementation of an anchor mechanism is illustrated in FIG. 16. In this implementation, the distal portion of the anchor mechanism 470 includes one or more barb members 472 or similar tissue engaging hooks. As the anchor mechanism 470 is deployed by advancing the mechanism 470 distally beyond the catheter notch 442, the barb members 472 deploy to an open configuration. Upon further advancement of the anchor mechanism, the barb members can engage firmly in the tissue, for example the ceiling wall of the heart chamber (not shown). Again, as shown in FIG. 16, the shaft 474 of the anchor mechanism 470 provides an axis of rotation 452 for the catheter 410 when the catheter 410 is used for creating a zone of ablation. The barb members 472 can collapse as the anchor mechanism 470 is withdrawn into a lumen of the catheter by way of the notch 442, for example, by actuating a slider mechanism at the proximal housing of the catheter.

Figure 17:
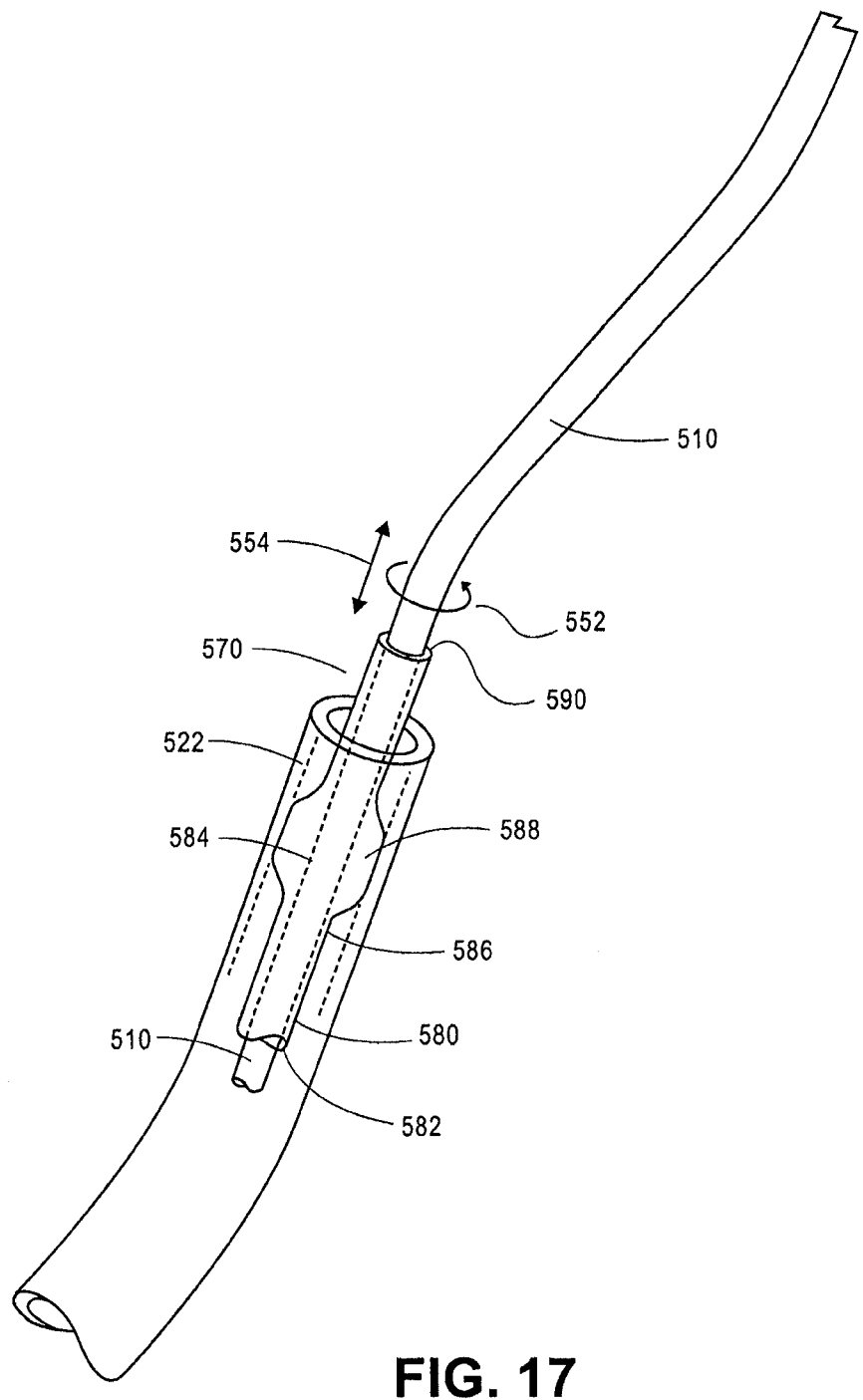

In general, in another aspect, an ablation device including a catheter having a distal tip assembly as described herein, but without a need for physical anchoring to the ceiling wall of the heart chamber is provided. As shown in FIG. 17, in one implementation, the anchor mechanism 570 of the ablation device includes a double wall tubing 580 having an annulus 582 between an inner wall 584 and an outer wall 586. Anchor mechanism 570 is an elongate structure spanning from a distal portion of the ablation catheter (see FIG. 17) to substantially the proximal portion of the device (not shown). The distal portion of the anchor mechanism 570 includes an expandable member, for example, an inflatable balloon 588 (see FIG. 17) which can communicate with a connector, for example, a luer fitting at the proximal end of the anchor mechanism 570 (not shown). Although a balloon is described as an exemplary expandable member, it is envisioned that other expandable members including but not limited to a cage or stent can be used. The inner lumen 590 of the anchor mechanism 570 provides a passageway for the ablation catheter 510 such that the catheter is free to move axially 554 and radially 552 within. As shown in FIG. 17, during use, the anchor mechanism 570 can be positioned inside the guide catheter 522 and advanced distally until a distal portion of the anchor mechanism 570 extends beyond the guide catheter 522 while the balloon 588 remains inside the guide catheter 522 substantially proximal to the guide catheter 522 end. In another implementation at least a part of the expandable member of the anchor mechanism remains inside the guide catheter, while another part of the expandable member extends distally beyond the guide catheter end (not shown). In yet another implementation the distal portion of the anchor mechanism remains substantially proximal to the distal end of the guide catheter (not shown).

To effect anchoring, the balloon can be inflated with a suitable fluid (e.g., saline or $CO_2$) sufficiently such that a distal portion of the anchor mechanism is held firmly in the guide catheter. The ablation catheter 510 can then be advanced distally (see arrow 554 in FIG. 17) through the inner lumen 590 of the anchor 570. As shown in FIG. 17, when the balloon 588 is inflated, the distal portion of the catheter 510 exiting from the anchor mechanism 570 is free to rotate in a manner 552 about a longitudinal axis, yet is held firmly in the guide catheter 522. As required, the catheter distal portion can be shaped by bending as described herein to a desired position (e.g., see FIGS. 3A-C). When anchored at the end of the guide catheter, the distal portion of the ablation catheter can be caused to follow a fixed rotational path without being susceptible to wavering or wandering as the catheter is rotated or otherwise guided in the heart chamber to create a zone of ablation.

The creation of a zone of ablation is facilitated by moving the distal portion of the catheter sufficiently away from the longitudinal axis of the catheter followed by rotation around an axis of rotation provided by an anchor mechanism. The location and orientation of the distal tip assembly, and the resulting direction of the ultrasound energy beam, is determined by the bending of the catheter distal portion at one, two or more locations along the catheter. In one implementation an ultrasound beam is presented to the tissue at a substantially orthogonal angle to achieve efficient ablation of the tissue. The direction of the sound beam can be adjusted by manipulating the bending of the catheter distal portion. This can be achieved by presenting the beam to the tissue in a duty cycle manner where the beam is energized for a pre-determined period followed by a quiet period. During this quiet period, a portion of the sound beam is reflected by the tissue, and the intensity of the reflection is measured by the same transducer being used in a receive mode. An operator or a control system can manipulate the angle of the ultrasound energy beam to maximize the intensity of the reflected sound beam. This ensures that the beam is substantially orthogonal to the tissue. As the beam is swept along the tissue, the distal tip assembly angle can be continuously manipulated such that the beam is presented to the tissue in a substantially orthogonal manner at all times. This can be achieved by a microprocessor controlled system (not shown) which utilizes the information provided by the reflected signal and then manipulates the tip bending through the pull wires connected to appropriate stepping motors. The motor mechanism can be contained in a separate module connected to the generator by means of an electrical cable (not shown). The proximal housing of the ablation catheter can be arranged to engage with the motor module making appropriate connections between the slider mechanisms and the corresponding motors (not shown). The resulting zone of ablation would then achieve maximum ablation, and the irregular anatomy, if any, of the heart chamber would be effectively addressed.

It is envisioned that a zone of ablation produced using the device described herein can be lesion in tissue having a shape including but not limited to a ring, elliptical, linear, and curvilinear as created by a combination of bending and/or rotating motions of the device.

Figure 11:
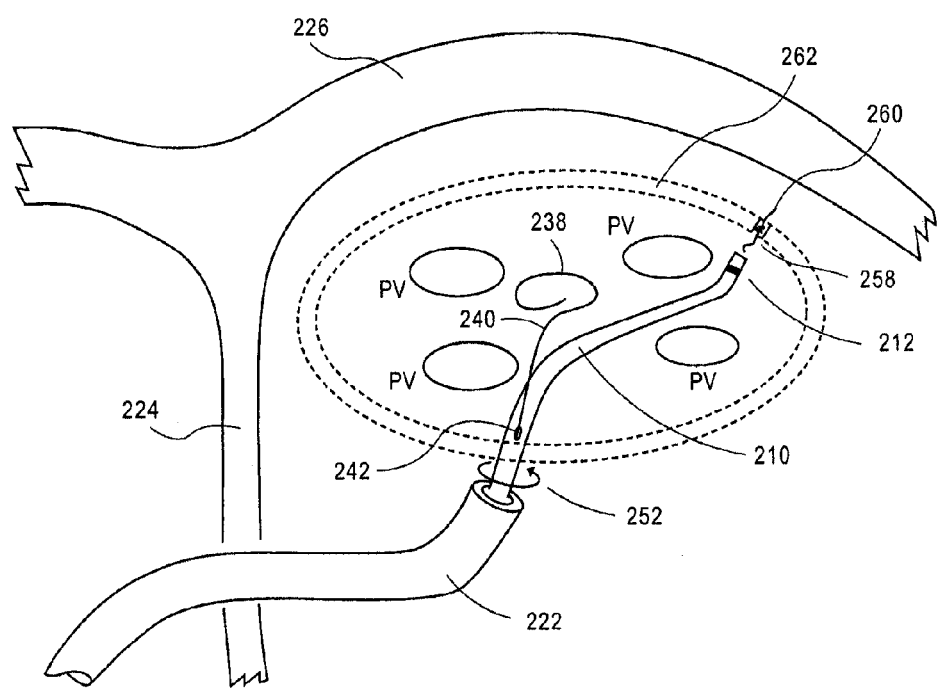
FIG. 11 shows an ablation zone encircling four pulmonary veins and the device in one embodiment of the invention.

In general, in another aspect, methods of using the embodiments described herein, for example, in treating atrial fibrillation, are provided. By way of example, a use of the device of the first embodiment is illustrated in FIG. 11. One method of using the device can include the following steps:

1. A guide catheter sheath 222 is positioned across the atrial septum 224 of a heart in a conventional way. One such technique is described by Gill (J. S. Gill, How to perform pulmonary vein isolation. Europace 2004 6(2):83-91). The opening of the guide catheter 222 is directed towards the ceiling 226 of the heart chamber.

2. Ablation catheter 210 is advanced through the guide catheter 222 and beyond the guide catheter 222 open end towards the tissue area in the middle of the pulmonary veins (PV) such that the distal tip assembly 212 points generally towards a part of the tissue surrounded by the PV.

3. Anchor mechanism 240 is deployed from within the catheter 210 and wire loop 238 is securely positioned against the tissue of the ceiling 226 of the heart chamber thereby providing an axis of rotation for the catheter 210.

4. Tip assembly 212 of the catheter 210 is moved away from the wire loop 238 by using the bending mechanism described herein and as shown FIGS. 3A-C. In general, the distal pull wire 116 is pulled by moving the first slider 120 (see FIG. 1), the catheter distal portion is bent at location 126 in the direction 172, thereby moving from position X to position Y, as shown in FIG. 3B. Next, the proximal pull wire 128, which is secured in the catheter lumen at a position by proximal adhesive band 130, is pulled by moving the second slider 132 (see FIG. 1). This results in the catheter 110 distal portion bending at location 136 and moving in the direction 174 to position Z, away from the longitudinal axis of the catheter, as shown FIG. 3C. In this way a portion or all of the tip assembly 212 can be positioned outside an area circumscribing the PV. More specifically, it is envisioned that the tip assembly 212 can be positioned suitably, in terms of distance and incident angle (e.g., orthogonal), to ablate tissue outside of an area defined by the PV.

5. The tip assembly 212 is oriented towards the tissue 226, and the device is energized by a generator (not shown) to provide a beam 258 of emitted ultrasound energy which impinges on the tissue 226. This energy beam 258 creates an ablation zone 260 in the tissue 226.

6. The treatment of the tissue is continued until a complete ablation of transmural thickness is achieved.

7. Catheter 210 is progressively rotated in a manner 252 about an axis as indicated in FIG. 11, such that the tip assembly 212 and the sound beam 258 traverses in a substantially circular path in the heart chamber (indicated as dashed lines 262 in FIG. 11). The treatment of tissue along a tissue path is continued until a complete ablation of transmural thickness is achieved along the entire path to create a partial or a complete zone of ablation 262 around all the targeted pulmonary veins, thereby achieving a conduction block.

8. The anchor mechanism 240 is retracted into a lumen through the notch 242 by actuating the appropriate slider mechanism at the proximal housing (not shown).

9. Distal tip assembly 212 is returned to a relaxed position by releasing the pull tension on the respective pull wires (not shown) thereby readying the catheter 210 for retraction into the guide catheter 222.

10. The ablation catheter 212 and the guide catheter 222 are removed from the body.

Figure 12:
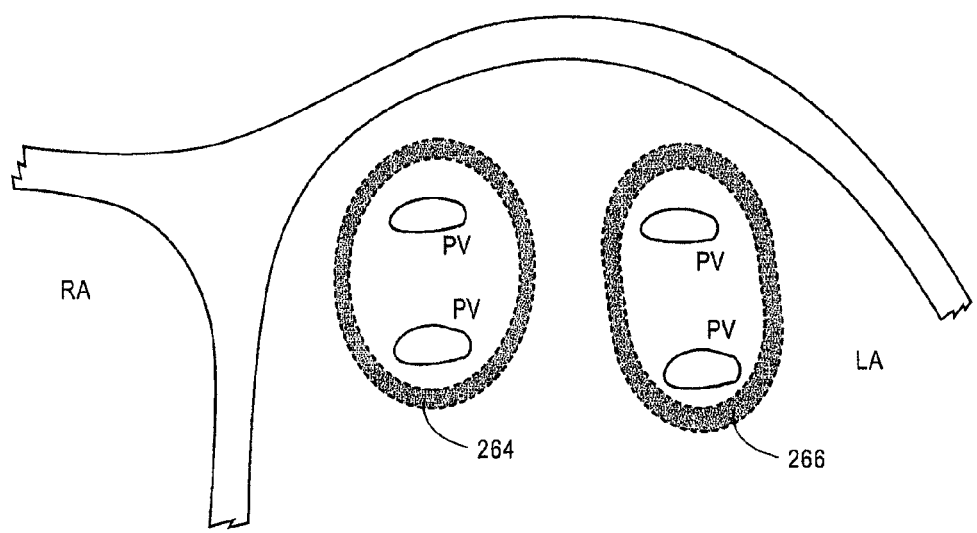
FIG. 12 shows two ablation zones each around two pulmonary veins.
Figure 13:
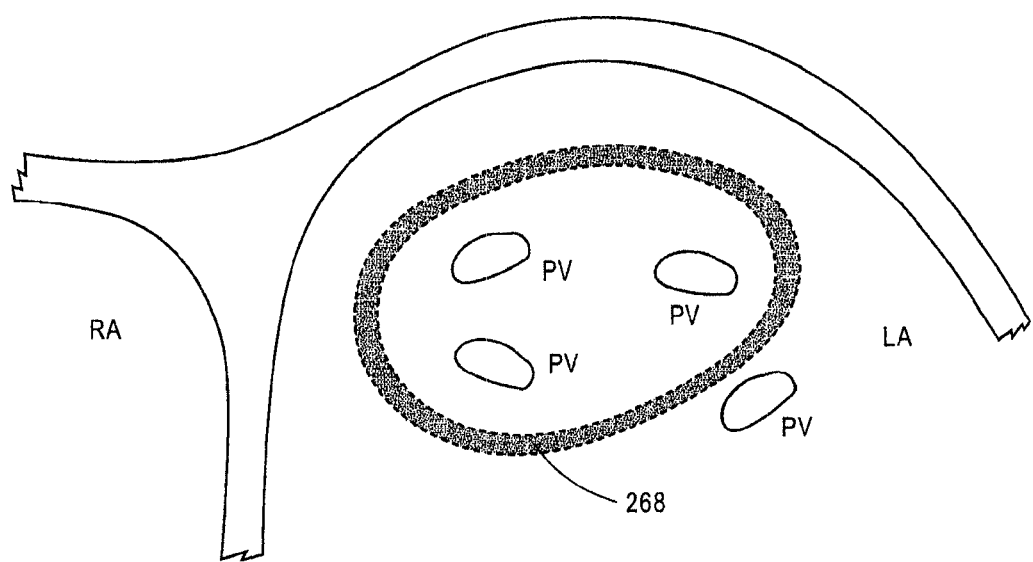
FIG. 13 shows an ablation zone around three pulmonary veins.

The method outlined above provides for a zone of ablation, having a shape as described herein, around four pulmonary veins. However, as shown in FIG. 12, in another method of using the device a conduction block can be achieved by providing two zones of ablation, for example, ablation rings 264 and 266, each around two PV. Alternatively, an ablation ring 268 can be placed around three PV as shown in FIG. 13. It is envisioned that any combination of ablation zones including but not limited to rings could be placed around one, two, three, or four pulmonary veins to achieve a complete conduction block.

In another implementation a method of using the device described herein can include the following steps:

1. A guide catheter sheath 222 is positioned across the atrial septum 224 of a heart in a conventional way. The opening of the guide catheter 222 is directed towards the ceiling 226 of the heart chamber.

2. Ablation catheter 210 is advanced through the guide catheter 222 and beyond the guide catheter 222 open end towards the tissue area in the middle of the pulmonary veins (PV) such that the distal tip assembly 212 points generally towards a part of the tissue surrounded by the PV.

3. Tip assembly 212 of the catheter 210 is moved away from the wire loop 238 by using the bending mechanism described herein and as shown FIGS. 3A-C. In general, the distal pull wire 116 is pulled by moving the first slider 120 (see FIG. 1), the catheter distal portion is bent at location 126 in the direction 172, thereby moving from position X to position Y, as shown in FIG. 3B. Next, the proximal pull wire 128, which is secured in the catheter lumen at a position by proximal adhesive band 130, is pulled by moving the second slider 132 (see FIG. 1). This results in the catheter 110 distal portion bending at location 136 and moving in the direction 174 to position Z, away from the longitudinal axis of the catheter, as shown FIG. 3C. In this way a portion or all of the tip assembly 212 can be positioned outside an area circumscribing the PV. More specifically, it is envisioned that the tip assembly 212 can be positioned suitably, in terms of distance and incident angle (e.g., orthogonal), to ablate tissue outside of an area defined by the PV.

4. Anchor mechanism 240 is deployed from within the catheter 210 and wire loop 238 is securely positioned against the tissue of the ceiling 226 of the heart chamber thereby providing an axis of rotation for the catheter 210.

5. The device is energized by a generator (not shown) to provide a beam 258 of emitted ultrasound energy which impinges on the tissue 226. This energy beam 258 creates an ablation zone 260 in the tissue 226.

6. The treatment of tissue is continued until a complete ablation of transmural thickness is achieved.

7. Catheter 210 is progressively rotated in a manner 252 about an axis as indicated in FIG. 11, such that the tip assembly 212 and the sound beam 258 traverses in a substantially circular path in the heart chamber (indicated as dashed lines 262 in FIG. 11). The treatment of tissue along a tissue path is continued until a partial or a complete zone of ablation of transmural thickness is achieved along the entire path to create complete ablation, for example, shaped as a ring 262 around all the targeted pulmonary veins, thereby achieving a conduction block.

8. The anchor mechanism 240 is retracted into a lumen through the notch 242 by actuating the appropriate slider mechanism at the proximal housing (not shown).

9. Distal tip assembly 212 is returned to a relaxed position by releasing the pull tension on the respective pull wires (not shown) thereby readying the catheter 210 for retraction into the guide catheter 222.

10. The ablation catheter 212 and the guide catheter 222 are removed from the body.

In a further implementation, wherein the anchor mechanism of the device is the mechanism as shown in FIG. 17 and as described herein, a method of using the device can include the following steps:

1. Referring to generally to FIG. 11 (disregarding the anchor mechanism 240 depicted therein), a guide catheter sheath 222 is positioned across the atrial septum 224 of a heart in a conventional way. The opening of the guide catheter 222 is directed towards the ceiling 226 of the heart chamber.

2. Referring now to FIG. 17, anchor mechanism 570 is advanced through the guide catheter 522 and beyond the guide catheter 522 open end towards the tissue area in the middle of the pulmonary veins (PV) (not shown) such that the anchor mechanism 522 points generally towards a part of the tissue surrounded by the PV.

3. Referring still to FIG. 17, the balloon 588 of the anchor mechanism 570 is inflated with a fluid such that a distal portion of the anchor mechanism 570 is held firmly in the guide catheter 522.

4. The ablation catheter 510 is advanced through the inner lumen 590 of the anchor mechanism 570 and into the heart chamber.

5. Referring generally again to FIG. 11 (disregarding the anchor mechanism 240 depicted therein), the tip assembly 212 of the catheter 210 is bent into a shape using the bending mechanism described herein and as shown FIGS. 3A-C. Thus, a portion or all of the tip assembly 212 is positioned outside of an area circumscribing the PV.

6. The device is energized by a generator (not shown) to provide a beam 258 of emitted ultrasound energy which impinges on the tissue 226. This energy beam 258 creates an ablation zone 260 in the tissue 226.

7. The treatment of the tissue is continued until a complete ablation of transmural thickness is achieved.

8. Referring again to FIG. 17, catheter 510 is progressively rotated about an axis in a manner 552 such that the tip assembly and the sound beam traverses in a substantially circular path in the heart chamber (indicated as dashed lines 262 in FIG. 11). The treatment of tissue along a tissue path is continued until a partial or a complete ablation of transmural thickness is achieved along the entire path. Thus, a complete ablation ring 262 is made around all the targeted pulmonary veins, thereby achieving a conduction block.

9. The catheter 512 is returned to a relaxed position by releasing the pull tension on the respective pull wires (not shown) and the catheter 510 is retracted through the anchor mechanism.

10. The balloon 588 of the anchor mechanism 570 is deflated and the anchor mechanism 570 is retracted through the guide catheter 522 and the guide catheter 522 is removed from the body.

In another implementation, the methods described herein can be used to treat the left atrial appendage of the heart. In this case, the method can include use of the ablation device as described herein to produce a conduction block circumscribing the atrial appendage. It is envisioned that the atrial appendage can be treated alone or in conjunction with treatment of the PV using the ablation device of the invention.

Figure 18:
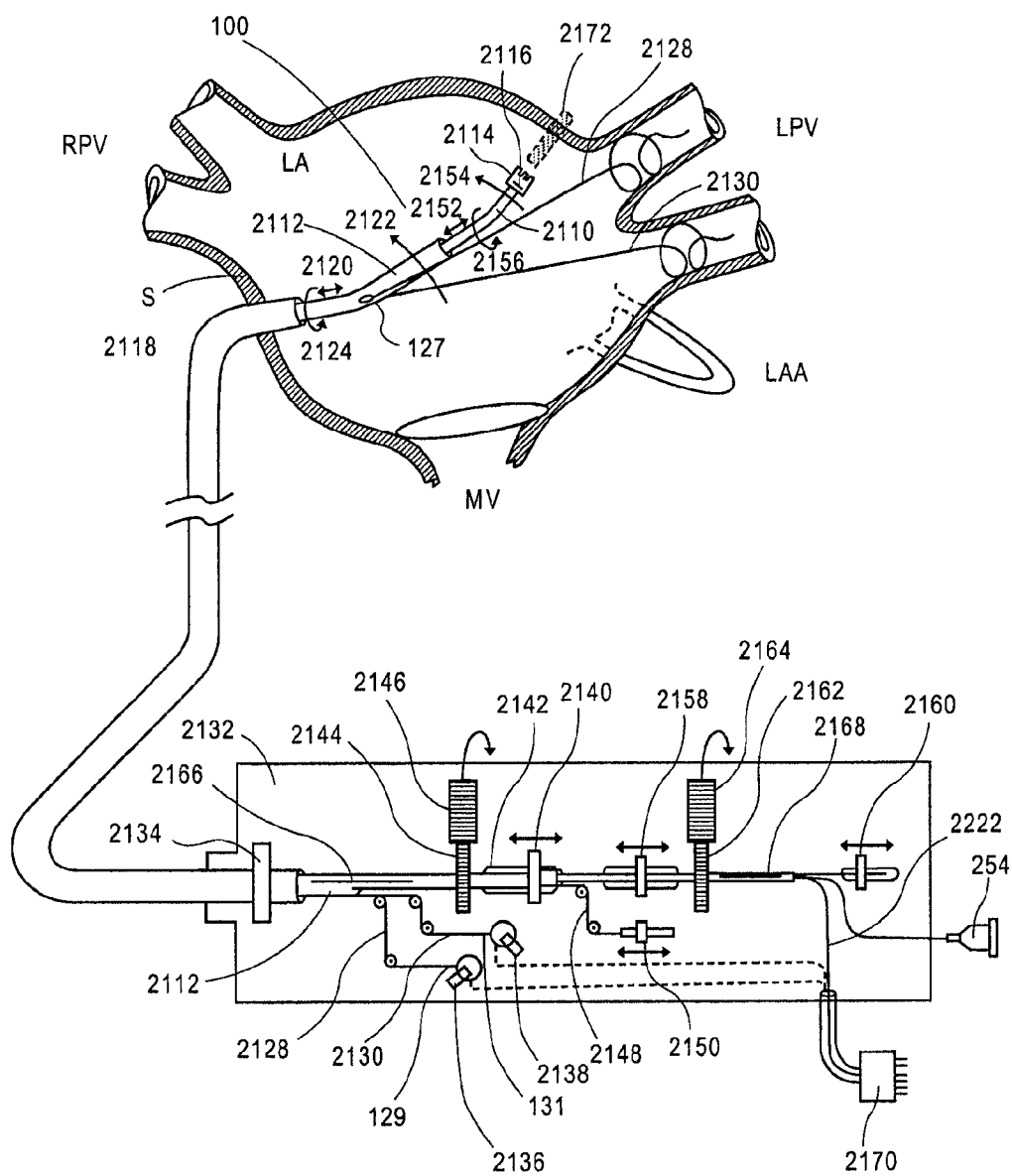
FIG. 18 shows yet another embodiment of the invention as positioned in the left atrium of the heart.

Referring to the embodiment of FIG. 18, the system consists of a catheter set 100, two positioning wires 2128 and 2130, and a guide sheath 2118. The catheter set 100 is composed of two catheters, a therapy catheter 2110 which is slideably contained in an outer catheter 2112. Catheter 2110 consists of a housing 2114 which contains the ultrasound transducer 2116. A more detailed description of the housing 2114 is presented later in this specification. Catheter 2110 is contained in the outer catheter 2112. The catheter 2112 is further contained in the transseptal guiding tube 2118. Catheter 2112 has three independent movements available. First, the catheter 2112 can move axially in the guide tube 2118 as depicted by 2120. The distal tip of the catheter 2112 is equipped to be bent in a manner 2122. Finally, the catheter 2112 can be rotated in the guide sheath 2118 in a manner 2124. Catheter 2112 contains a lumen 2126 which houses the locating wire springs 2128 and 2130. Wires 2128 and 2130 are independently movable in the lumen 2126 of catheter 2112.

The elements of the catheter systems are positioned in the left atrium (LA) of the heart. The wires 2128 and 2130 are positioned in the left pulmonary veins (LPV). The therapy catheter 2110, outer catheter 2112, and the distal portion of the guide sheath 2118 are positioned in the chamber of the left atrium. Other structures of the heart shown in FIG. 18 are the mitral valve opening (MV), left atrial appendage (LAA), and right pulmonary veins (RPV).

At the proximal end, the various catheter elements are connected to a variety of controls in a connector console 2132. After placement in the septum of the heart, the guide sheath 2118 is locked in position by means of the lever 2134. The locating wires 2128 and 2130 have markers 129 and 131 respectively at their proximal ends. The locating wires 2128 and 2130 are designed to be guided by hand by the surgeon, and after the intended positioning, are locked in by means of the lever mechanisms 2136 and 2138 at the position of the markers 129 and 131. The linear movement 2120 of the outer catheter 2112 is achieved by moving the slider 2140 which moves linearly in slot 2142. Once the desired position of the catheter 2112 is achieved, the slider 2140 can be locked in position. The rotational movement 2124 of the outer catheter 2112 is achieved by the gear mechanism 2144 and 2146. Gear 2144 is attached to the proximal end of the outer catheter 2112. Gear 2144 is driven by the pinion 2146 which is attached to a motor (not shown). The bending mechanism 2122 of the distal tip of the catheter 2112 is achieved by means of the pull wire 2148 which terminates in a slider mechanism 2150 which is lockable once the desired position of the bending of the catheter 2112 is achieved. All the motions described here can be achieved by hand or by using appropriate motors, linkages, and actuators in the console 2132.

Similar to the outer catheter 2112, the catheter 2110 also is provided with three independent movements. First, the catheter 2110 can be moved axially in the catheter 2112 as shown by movement 2152. This movement 2152 is controlled at the proximal end by means of the slider 2158 which is lockable once the desired position of the therapy catheter 2110 is achieved in the outer catheter 2112. Second, the distal portion of the catheter 2110 can be bent in the manner 2124 by means of a pull wire (not shown) connected to the slider mechanism 2160 at the proximal end console 2132. Again, the slider 2160 is lockable in position once the desired position of the bend of the tip of the catheter 2110 is achieved. Finally, the catheter 2110 can be rotated in the outer catheter 2112 in a manner shown as 2156. This motion is effected by the gear mechanism 2162 and 2164 in the console 2132. Gear 2162 is attached to the proximal end of the catheter 2110, and it is driven by the pinion 2164 which is connected to a motor (not shown). The catheters 2110 and 2112 contain the corresponding orientation marks 2166 and 2168 provided on the shafts thereof. The console also consists of a connector 2170 which electrically connects to a power generator and controller (not shown). The connector 2170 also provides electrical connections to the positioning wires 2128 and 2130 by means of being connected to the locking levers 2136 and 2138 in the console 2132. As described later, the connector 2170 provides electrical connections to the ultrasound transducer 2116, a temperature sensor at the housing 2114, and the positioning wires 2128 and 2130.

Figure 36:
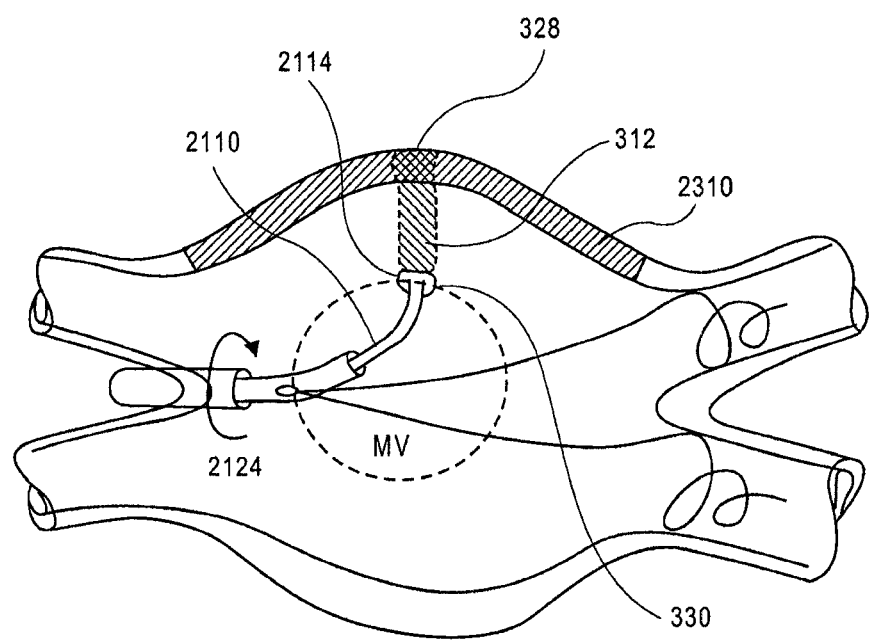
FIG. 36 shows a vertical line of ablation ending at the mitral valve annulus.

FIG. 36 shows the positions of the catheter elements in the left atrium. The locating wires 2128 and 2130 are positioned in the two pulmonary veins (LPV1 and LPV2). As shown in the figure, the housing 2114 at the tip of the catheter 2110 points towards the wall tissue 2174 of the atrium. As described in detail later, the ultrasound element 2116 in the housing 2114 emits an ultrasound beam to establish an ablation window 2172. Now, as the outer catheter 2112 is rotated inside the guide sheath 2118 in the manner 2124 and around the locating wires 2128 and 2130, the ultrasound beam 2172 sweeps a generally circular path 2176 creating a section of a conical shell. The purpose of the two positioning wires 2128 and 2130 is to assure that the rotation of the housing 2114 will occur in a path outside the pulmonary vein LPV1 and LPV2. The objective of the invention is to find at least one such curve where the sweep path 2176 of the ultrasound beam 2172 intersects with the atrial wall tissue 2172 in a contiguous locus.

Figure 20:
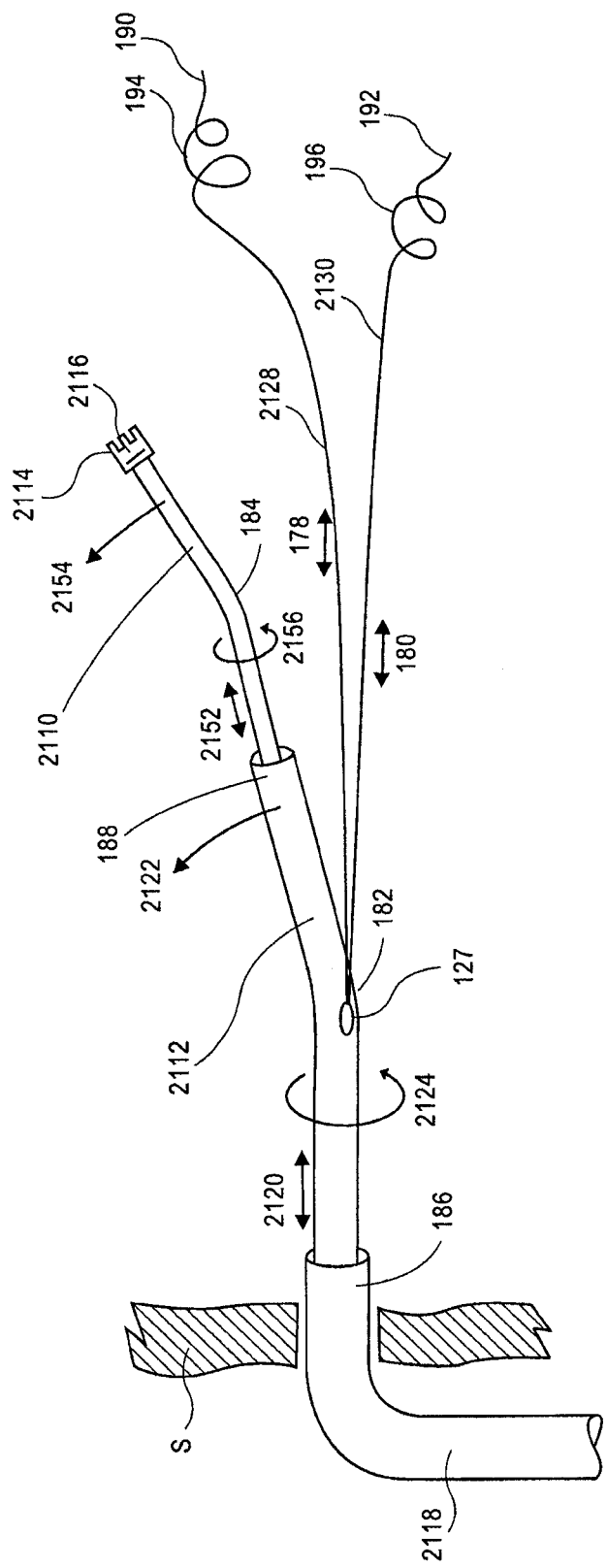
FIG. 20 shows the distal end of the device of FIG. 18 beyond the guiding sheath.
Figure 23:
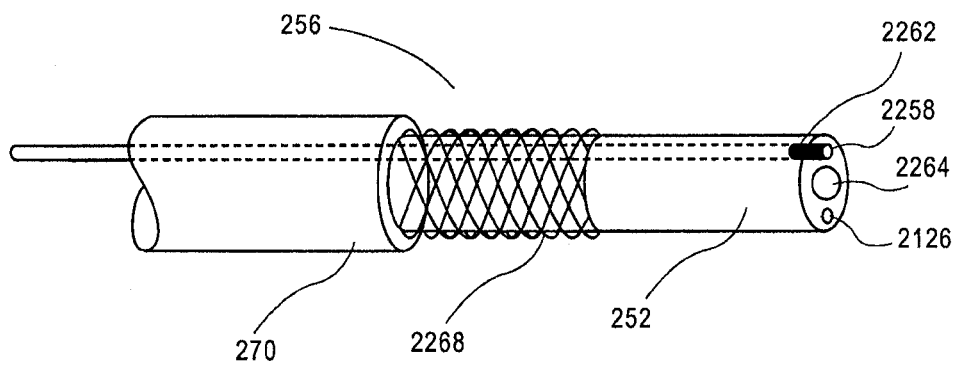
FIG. 23 shows a view of the construction of the outer catheter.

FIG. 20 shows the catheter apparatus. The therapy catheter 2110 and the outer catheter 2112 form a conjoined set 100 which can be freely moved axially in the guide sheath 2118. The very tip section 186 of the sheath 2118 has a snug fit over the outer catheter 2112 so as to provide a firm grip on the catheter 2112 while it is performing its rotation 2124. Catheter 2112 can also be moved axially inside the guide sheath 2118 in a manner 2120. In addition, the tip of the catheter 2112 can be bent about a pivot point 182 in a manner 2122. Catheter 2112 has a separate lumen 2126 which houses the locating wires 2128 and 2130. These wires exit at the notch 127 and can be advanced or retracted in a manner 178 and 180. The wires 2128 and 2130 are constructed from a material such as nitinol so as to take the shape of conical springs 194 and 196 respectively when in free space. The ends of the positioning wires can also be shaped in a suitable configuration other than the conical shapes described herein. The tips 190 and 192 of the wires 2128 and 2130 are made of a soft spring coil so as not to cause any injury to the tissue of the heart where the tips might be in contact and move against. The wires 2128 and 2130 can be advanced in the atrial chamber with the intention of being positioned in the two pulmonary veins. The wires 2128 and 2130, when residing completely inside the lumen 2126 of the catheter 2112, are held in a generally straight shape conforming to confines of the lumen 2126 (ref. FIG. 23). As they are advanced outwards, and as they exit the notch 127, they take on the predetermined shape of conical springs 194 and 196. The rotation 2124 of the catheter 2112 is essentially around the wires 2128 and 2130 with lumen 2126 serving as the axis of said rotation.

As described earlier, the therapy catheter 2110 similarly has three degrees of motion. It can move axially in the outer catheter 2112 in a manner 2152. Catheter 2110 can be bent in a manner 2154 around a pivot point 184. Finally, the catheter 2110 can be rotated in the manner 2156. The tip end 188 of the outer catheter 2112 has a snug fit over the catheter 2110 to provide a firm support during the rotation 2156 of the catheter 2110. Otherwise, the catheter 2110 is freely movable inside the outer catheter 2112 in a manner 2152.

Figure 21A:
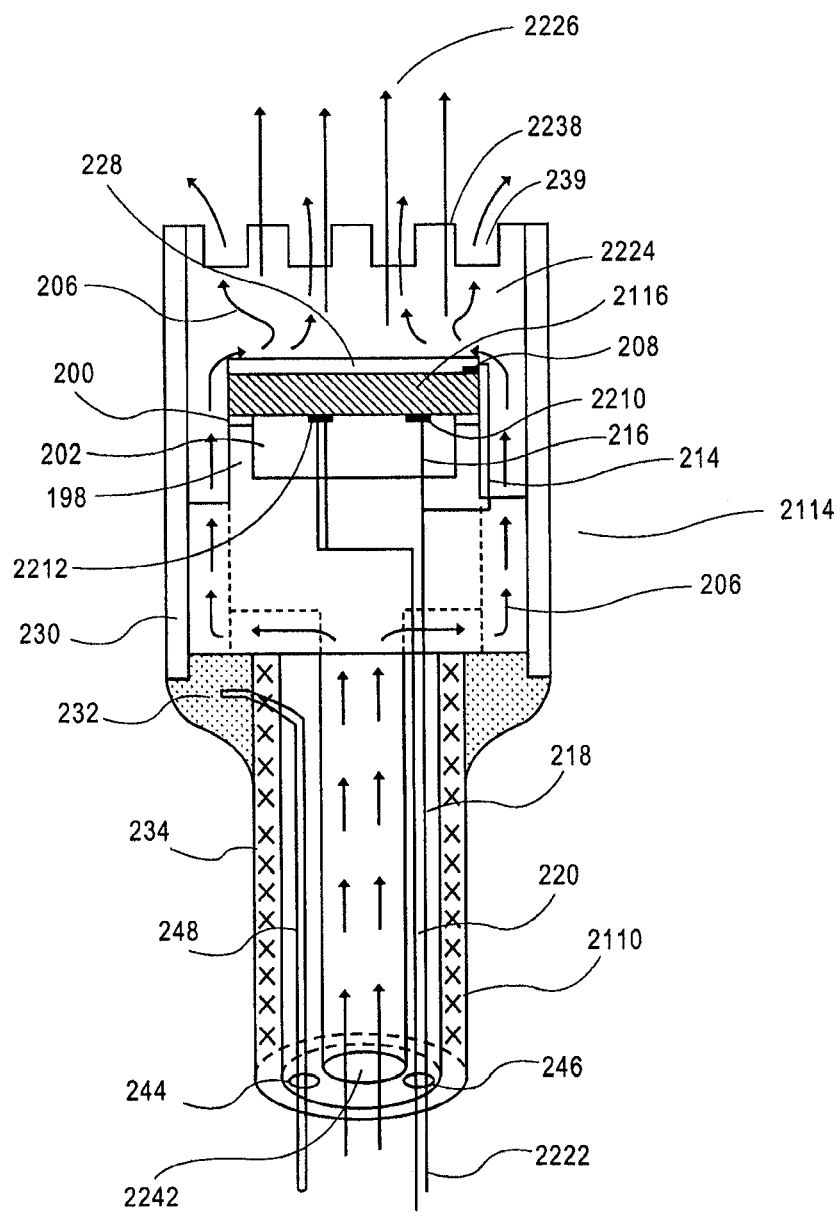
FIG. 21A shows the details of the transducer housing at the distal tip of the catheter.
Figure 21B:
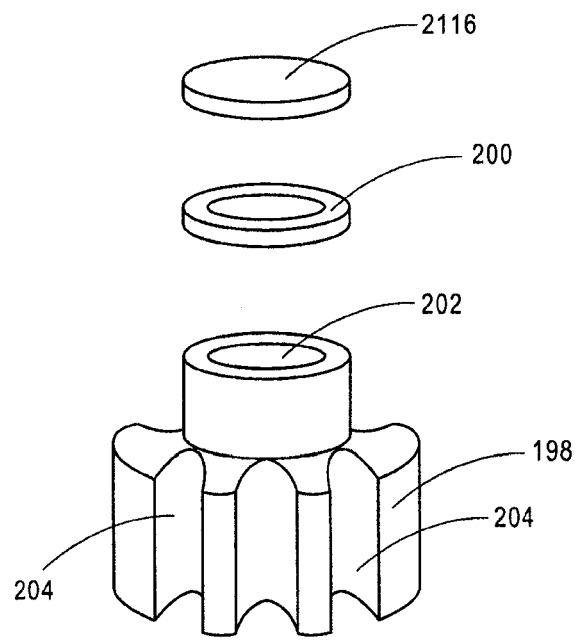
FIG. 21B shows the transducer mounting header with fluid flow channels.

The tip of the catheter 2110 has a housing 2114 which contains an ultrasound transducer 2116. FIG. 21A shows the details of the housing 2114. The transducer 2116, which is of a generally circular shaped disc fabricated from a suitable piezoelectric material, is bonded to the end of a cylindrical backing 198 by means of an adhesive ring 200. The attachment of the transducer 2116 to the backing 198 is such that there is an air pocket 202 between the back surface of the transducer 2116 and the backing 198. This air pocket 202 is useful in the sense that when the transducer 2116 is energized by the application of electrical energy, the emitted ultrasound beam is reflected by the air pocket 202 and directed outwards from the transducer 2116. The air pocket 202 can be replaced by any other suitable material such that a substantial portion of the ultrasound beam is directed outwards from the transducer 2116. Backing 198 can be made of a metal or a plastic, as shown in more detail in FIG. 21B, such that it provides a heat sink for the transducer 2116. The cylindrical backing 198 has a series of grooves 204 disposed longitudinally along the outside cylindrical wall. The purpose of the grooved backing is to provide for the flow of a cooling fluid 2224 substantially along the outer surface of backing 198 and past the face of the transducer 2116. The resulting fluid flow lines are depicted as 206 in FIG. 21A. In an actual clinical situation, saline or any other physiologically compatible fluid can be used as the cooling fluid 2224 at any safe temperature preferably below the body temperature of 37° Celsius.

The transducer 2116 has an electrical contact 208 on the front surface of the transducer using a suitably insulated wire 214. The electrical contact 208 can be made by standard bonding techniques such as soldering or wire bonding. The contact 208 is preferably placed closer to the edge of the transducer 2116 so as not to disturb the ultrasound beam 2226 emitted by the transducer 2116 upon being electrically energized. The front face of the transducer 2116 is covered with another material known as the matching layer 228. The purpose of the matching layer 228 is to increase the efficiency of coupling of the ultrasound wave 2226 into the surrounding fluid 2224. Generally, as the ultrasound energy moves from the transducer 2116 into the fluid 2224, the acoustic impedances are different in the two media, resulting in a reflection of some of the ultrasound energy back into the transducer 2116. A matching layer 228 provides a path of intermediate impedance so that the sound reflection is minimized, and the output sound from the transducer 2116 into the fluid 2224 is maximized The thickness of the matching layer 228 is maintained at one quarter of the wavelength of the sound wave in the matching layer material. There are a number of material candidates, generally from a family of plastics, which can serve as the matching layer. One such material is parylene which can be easily placed on the transducer face by a vapor deposition technique. In addition one can deposit a multitude of matching layers, generally two or three, on the face of the transducer to achieve maximum energy transmission from the transducer 2116 into the fluid 2224. Conversely, same reflection principle is used on the backside of the transducer 2116. Here the air pocket 202 is provided. Ultrasound energy sees a large impedance mismatch, so a majority of energy is reflected back into the transducer 2116 and emitted from its front face. Thus by using a combination of the air pocket 202 on the back and matching layer(s) 228 on the front, the efficiency of the transducer 2116 is greatly enhanced. Alternatively, the air pocket 202 could be replaced with a backing block material that minimizes reflections from the behind the transducer 2116. While this backing block can reduce the amount of energy transmitted from the front of transducer 2116, it removes reverberations and other artifacts when transducer 2116 is operating as an ultrasound receiver. The backing block material is designed to maximize the efficiency of transducer 2116 while providing adequate suppression of imaging artifacts.

The back side of the transducer 2116 also has an electrical connection 2210 to a suitably insulated wire 216. Again, the bonding can be done in any of the conventional manner such as a solder joint or wire bonding. Wires 214 and 216 together form a pair 218 which can be a twisted pair or miniature coaxial cable. On the backside of the transducer 2116, there is temperature sensor 2212. Its purpose is to monitor the temperature of the transducer 2116 during its use. The sensor can be a thermocouple or a thermistor of appropriate size so as to cover a small portion of the transducer surface. Two wires 220 provide the electrical connection to the temperature sensor 2212. The wire pairs 218 and 220 form a bundle 2222. The flow of the cooling fluid is achieved through a lumen 2242 which is terminated in a fluid port 254 at the proximal end (ref. FIG. 18).

The transducer-backing subassembly is encased in a tubular jacket 230. The material of the jacket can be metal or plastic. The tubular jacket protrudes distally beyond the transducer 2116 to form a fluid chamber or pocket 236. This pocket 236 provides for a column of fluid 2224 which is in a physical and thermal contact with the transducer 2116. This invention provides for the fluid column 2224 for two distinct objectives. First, the column 2224 provides for the thermal cooling of the ultrasound transducer 2116. This column 2224 is at a lower temperature than the transducer face and therefore aids in cooling the transducer 2116. The temperature of the fluid 2224 can be easily controlled by providing the cooling fluid at a suitable temperature. The temperature of the transducer is constantly monitored by the temperature sensor 2212 disposed on the back of the transducer 2116. Secondly, the fluid column provides for a separation medium between the ultrasound transducer 2116 and the blood surrounding the housing 2114 during the use of the device in a clinical setting.

Figure 21C:
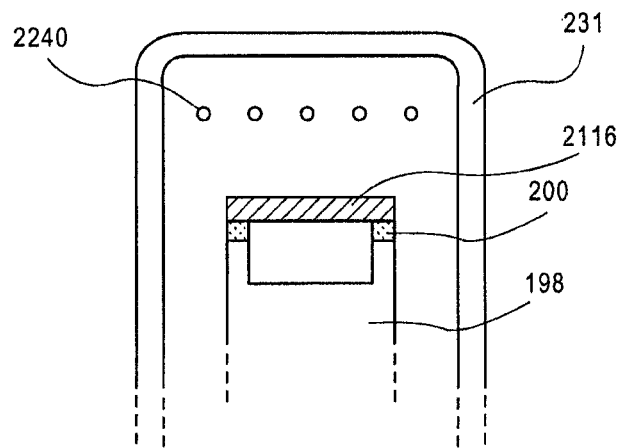
FIG. 21C shows an alternative design for the fluid pocket containment component.

Still referring to FIG. 21A, the tubular jacket 230 is shown at its distal end in a "castle head" configuration with slots 239. The purpose of the slots 239 is to provide for exit ports for the flowing fluid 2224. The slots 239 are desirable for the situation when the front tip of the catheter is in contact with the tissue or other structures during the use of the device, to maintain the important flow of the cooling fluid. The fluid flow lines 206 flow along the grooves 204, bathe the transducer 2116, form the fluid column 236 and exit through the slots 239 at the castle head 2238. The maintenance of the fluid flow through the tubular jacket 230 can be achieved in a number of different ways. One additional such way is shown in FIG. 21C where the tubular jacket 230 consists of an enclosed chamber with small holes 2240 on the cylindrical surface closer to the distal end. These holes 2240 provide for the exit path for the flowing fluid.

It is important to maintain the transducer functioning at a lower temperature so as to operate at a safe temperature for the patient, and to preserve consistent performance of the piezoelectric material, which can be damaged by exposure to excessive heat.

Another important function of the housing design of this invention is to provide a barrier between the face of the transducer 2116 and the blood residing in the atrium of the heart. If the fluid flow is not incorporated, and the transducer face is directly in contact with blood, the blood will coagulate on the surface of the transducer 2116. The coagulation will be further aggravated if the transducer gets hotter during its operation. The coagulated blood will provide a barrier to transmission of the ultrasound energy in an unpredictable way depending on the coverage of the transducer face by the coagulated blood. Additionally, there is serious risk of forming a blood clot at the interface of the transducer 2116 and the surrounding blood. The incidence of any blood clot is undesirable in any situation in the heart chamber. The flow of the cooling fluid, as described in this invention, keeps the blood from getting in contact with the transducer face, thus avoiding the formation of blood clots. We have determined that a flow rate of approximately 1 ml per minute is sufficient to maintain the fluid column 236 and keep the separation between the blood and the face of the transducer.

FIG. 21A shows the mounting of the transducer 2116 at an angle of 90 degrees to the axis of the catheter housing 2114. However, the transducer 2116 can also be mounted at any other angle. The exit path of the beam will be at 90 degrees to the face of the transducer. The remaining details of the catheter and the presentation of the ultrasound beam to the tissue will vary accordingly in order to achieve the intended effect of tissue ablation.

The transducer disc 2116, as shown in FIG. 21A, has a flat front surface. This front surface of the transducer can be either concave or convex to achieve an effect of a lens.

The tubular jacket 230 of the above description is attached to a catheter tubing 234 by means of adhesive 232. A pull wire 248 also is secured in the adhesive 232. The pull wire 248 is contained in a lumen 244. This pull wire 248 is utilized in bending the tip of the catheter 2110 in a manner 2154 (ref. FIG. 18). Another lumen 2242 provides the path for the fluid flow. The wire bundle 2222 is contained in a yet separate lumen 246 in the catheter tube 234.

Figure 22:
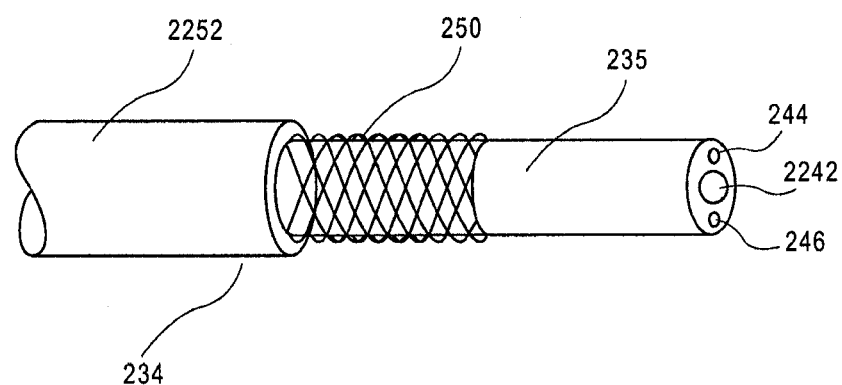
FIG. 22 is a view of the construction of the therapy catheter.

Referring to FIG. 22 showing the cut-away section, the catheter tubing 234 constitutes of a multilumen inner tubing 235 covered with a braid 250 and a jacket 2252. The multilumen tubing 235 has three lumens. The lumen 2242 is terminated in a fluid port 254 (ref. FIG. 18) at the proximal end of the catheter 2110. This allows the cooling fluid to be passed through the length the catheter and exit at the 'castle head' 2238 of housing 2114. The lumen 246 contains the wire bundle 2222, and the lumen 244 contains the pull wire 248. The tubing 2240 is encased in a braid 250 in a conventional way. The material of the braid can be round or flat metal wires, plastic filaments, or Kevlar. It is understood that the braid can be replaced with a spring like wrapping or a wrapping of foil. Finally, the braid 250 is covered in a smooth jacket 2252. The material of the jacket is generally plastic, and can be placed using conventional extrusion techniques. The braid 250 and the jacket 2252 together provide the tortional control of the catheter tubing 234. The tortional control is required to achieve the rotation 2156 (ref. FIG. 18) of the therapy catheter 2110.

Next, the construction of the outer catheter 2112 is shown in a cut-away section in FIG. 23. The catheter tubing 256 consists of a multilumen tubing 257 which is encased in a braid 2268 and a jacket 270. The multilumen tubing 256 has three lumens, one lumen 2258 contains a pull wire 2260 which is terminated at the tip in an adhesive band 2262. This pull wire is utilized in bending the outer catheter tubing in the manner 2122 (ref. FIG. 18). Another lumen 2126 is provided for the positioning wires 2128 and 2130. The multilumen tubing 256 is encased in a braid 2268 in a conventional way. The material of the braid can be round or flat metal wires, plastic filaments, or Kevlar. It is understood that the braid can be replaced with a spring like wrapping or a wrapping of foil. Finally, the braid 2268 is covered in a smooth jacket 270. The material of the jacket is generally plastic, and can be placed using conventional extrusion techniques. The braid 2268 and the jacket 270 together provide the tortional control of the outer catheter tubing 2112. The tortional control is required to achieve the rotation 2124 (ref. FIG. 18) of the outer catheter 2112.

When energized with an electrical pulse or pulse train, the transducer emits a sound wave with properties determined by the characteristics of the transducer 2116, the matching layer 228, the backing 202, the electrical pulse, and the tissue in front of the transducer. These elements determine the frequency, bandwidth and amplitude of the sound wave propagated into the tissue. Typically, the frequencies of the emitted sound are in the low megahertz range. For the intended use in this invention, for tissue imaging and ablation near the transducer, the useful frequencies range from 5 to 25 megahertz.

Figure 24:
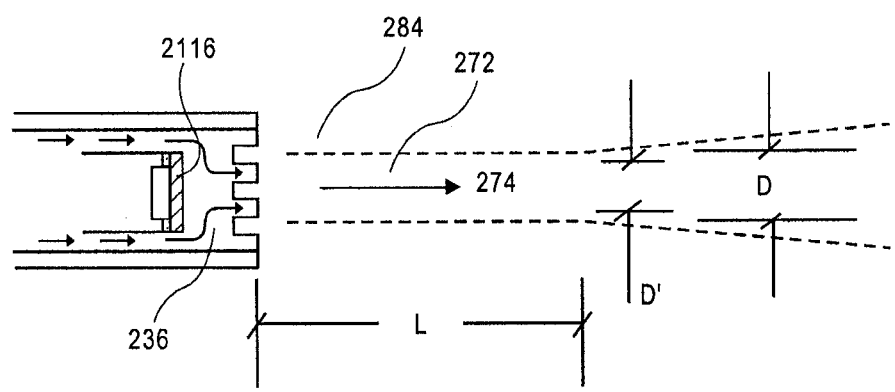
FIG. 24 is a view of the characteristics of the ultrasound beam as it exits from the transducer.

During one of the actual uses of the device of this invention, it will be placed in the atrium of the heart. Referring to FIG. 24, the transducer 2116 is maintained separated from the surrounding blood 284 by a fluid column 236. When the transducer 2116 is energized with an appropriate electrical pulse, it emits a beam 272 of ultrasound energy. A typical beam pattern is shown for the ultrasound wave as it is emitted by the transducer 2116. This beam pattern illustrates the outline of the ultrasound beam by mapping where the sound pressure falls by 6 dB relative to the midline of the beam. The sound beam 272 travels in the direction 274 away from the transducer 2116 in a generally collimated manner up to a distance of L and then diverges thereafter. The diameter at the origin of the ultrasound beam 272 corresponds to the diameter D of the transducer disc 2116. If the device relies on the natural focusing of a flat disc transducer, the ultrasound beam 272 converges slightly up to a depth of L, beyond which the beam diverges. The minimum beamwidth D' occurs at the distance L. It is well known that the distance L is determined by the diameter of the transducer disc D and the operating frequency. These relationships are well summarized by Bushberg et al [The Essential Physics of Medical Imaging, 2nd edition. Bushberg, Seibert, Leidholdt and Boone, Lippincott Williams & Wilkins, 2002; p. 491]. In this invention, a relatively large L is desired, since it establishes the size of the ablation window 2172. A variety of disc diameters and operating frequencies can be used. In general, D is selected as large as possible for a given device diameter, so that L is maximized A higher operating frequency will also increase the distance L. However since ultrasound is attenuated in tissue as a function of increasing frequency, the required depth of the lesions determines the useable maximum frequency. Given the constraints of device size and ultrasound attenuation, this invention uses, for example, an operating frequency of 12 MHz and a disc diameter of 2.5 mm, resulting in a depth L of 12 mm and a minimum beamwidth D' of 1.6 nun.

The natural focusing of a flat disc transducer provides adequate beam forming for typical uses of this invention. Adding an acoustic lens in front of transducer 2116 provides additional flexibility in adjusting the beam pattern. For example, an acoustic lens could create a beam that is more uniformly collimated, such that the minimum beamwidth D' approaches the diameter of the disc D. This will provide a more uniform energy density in the ablation window 2172, and therefore more uniform lesions as the tissue depth varies within the window. A lens could also be used to move the position of the minimum beamwidth D', for those applications that may need either shallower or deeper lesion. This lens could be fabricated from plastic or other material with the appropriate acoustic properties, and bonded to the face of transducer 2166. Alternatively, the circular piezoelectric disc could be fabricated with a front face that is curved instead of flat. A slight concave shape, for example, would move the focal point (i.e. smallest D') in towards the transducer, while a slight convex shape would move the focus outwards.

Figure 25:
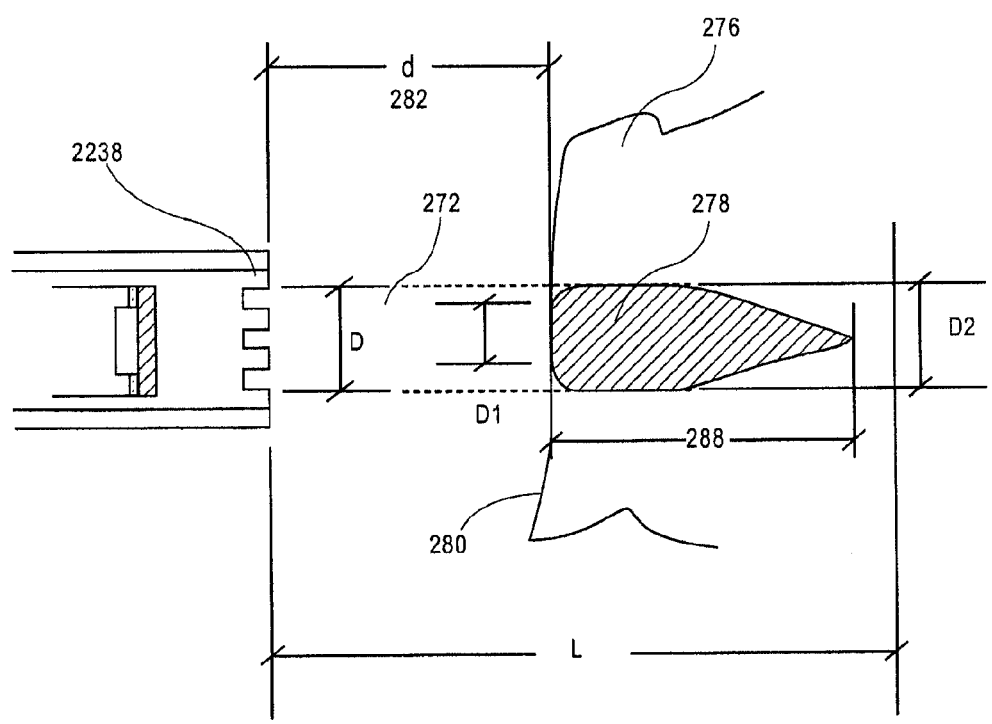
FIG. 25 shows formation of the shape of an ablation lesion.

The interaction of the ultrasound beam with the tissue is shown in FIG. 25. The tissue 276 is presented to the ultrasound beam 272 within the collimated length L. The front surface 280 of the tissue 276 is at a distanced (282) away from the face of the castle head 2238. As the ultrasound beam 272 travels through the tissue 276, its energy is absorbed by the tissue 276 and converted to thermal energy. This thermal energy heats the tissue to temperatures higher than the surrounding tissue. The result is a heated zone 278 which has a typical shape of an elongated tear drop. The diameter D1 of the zone 278 is smaller than the beam diameter D at the tissue surface 280. This is due to the thermal cooling provided by the surrounding fluid (cooling fluid 286 or blood 284) which is flowing past the tissue surface 280. As the ultrasound beam travels deeper into the tissue, the thermal cooling is provided by the surrounding tissue, which is not as efficient as that on the surface. The result is that the ablation zone 278 has a larger diameter D2 than D1 as determined by the heat transfer characteristics of the surrounding tissue as well as the continued input of the ultrasound energy from the beam 272. During this ultrasound-tissue interaction, the ultrasound energy is being absorbed by the tissue, and less of it is available to travel further into the tissue. Thus a correspondingly smaller diameter heated zone is developed in the tissue, and the overall result is the formation of the heated ablation zone 278 which is in the shape of an elongated tear duct limited to a depth 288 into the tissue.

The interaction of ultrasound energy with the live tissue is well studied and understood. One such description is presented in the article by Gail ter Haar "Acoustic Surgery, Physics Today, December 2001". In the zone 278 where the tissue is heated, the tissue cells are rendered dead due to heat. The temperatures of the tissue typically are above 55° Celsius in the heated zone 278 and the tissue is said to be ablated. Hence, the zone 278 can be depicted as the ablation zone.

Referring to FIG. 25, it is important to present the tissue 276 to the ultrasound beam 272 such that the tissue is within the collimated length L to achieve effective ablation. As the beam 272 is presented to the tissue for an extended period of time, the ablation zone 278 extends into the tissue, but not indefinitely. There is a natural limit of the depth of the ablation zone 278 as determined by the factors such as the attenuation of the ultrasound energy, heat transfer provided by the healthy surrounding tissue, and the divergence of the beam beyond the collimated length L. This effect is beneficial in the sense that there is a natural safety limit to the penetration of the ultrasound energy such that the ablation zone 278 stops growing as a steady state is reached between the input of ultrasound energy and its conversion in to thermal energy which is dissipated by the surrounding tissue.

Figure 26A:
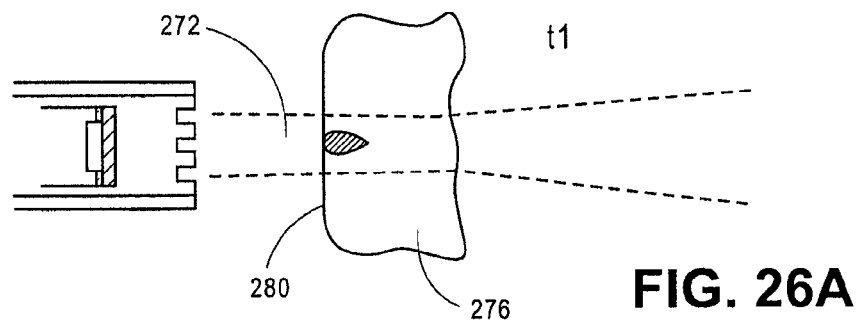
FIGS. 26 A-D show the development of the ablation lesion as function of time.
Figure 26B:
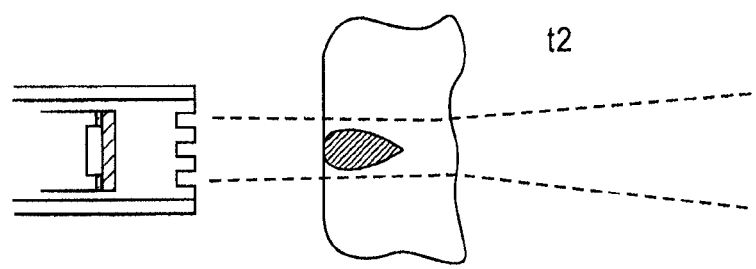
Figure 26C:
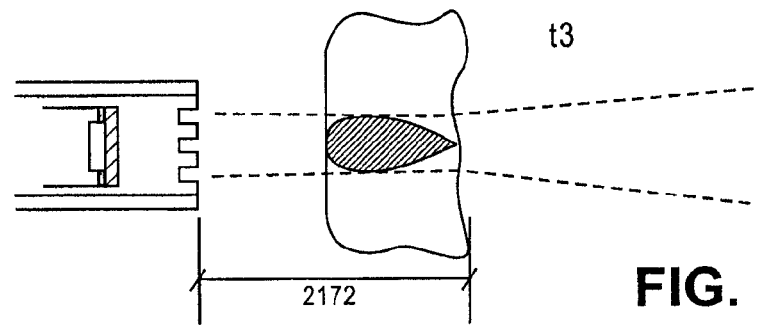
Figure 26D:
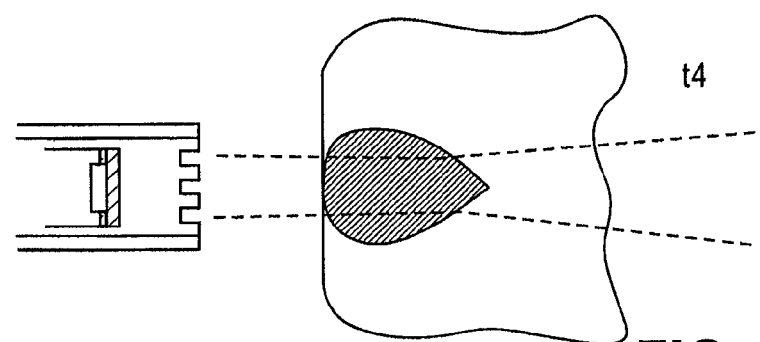
Figure 27A:
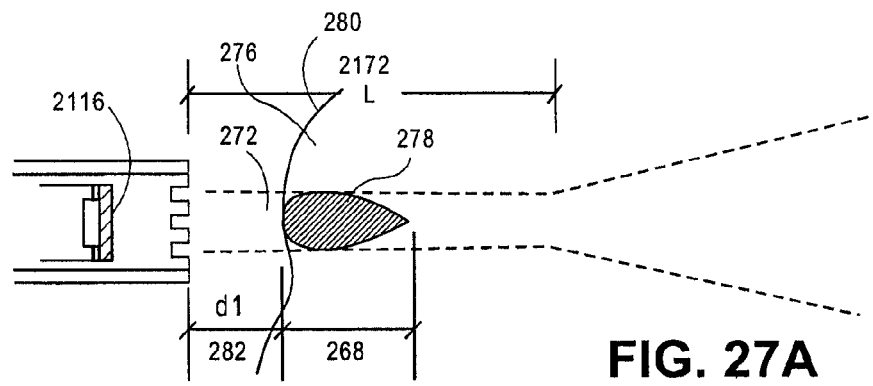
FIGS. 27 A-D show the interaction of the ultrasound beam with the tissue at various distances from the ultrasound transducer.
Figure 27B:
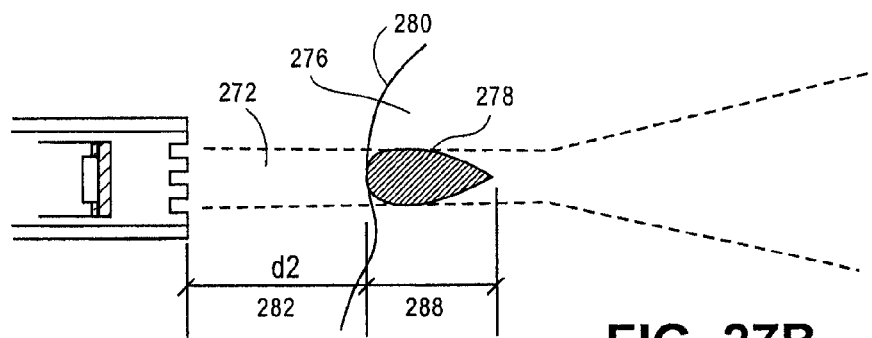
Figure 27C:
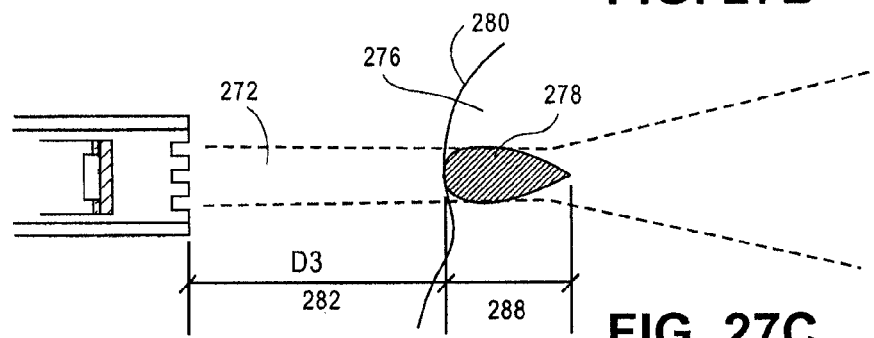
Figure 27D:
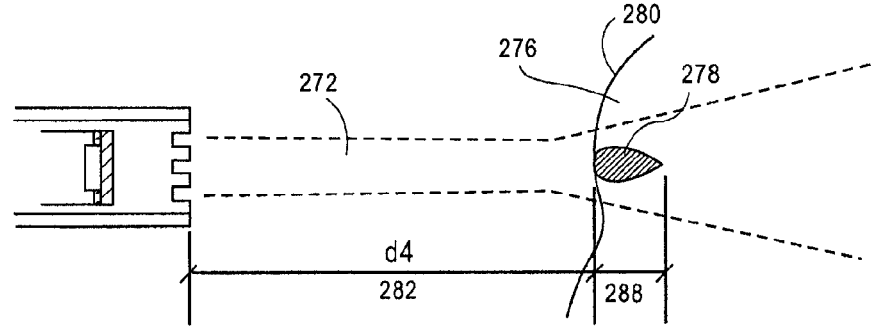

The ablation zone in the tissue is formed by the conversion of the ultrasound energy to thermal energy in the tissue. The formation of the ablation zone is dependent on time as shown in FIGS. 26 A-D, which show the formation of the lesion at times t1, t2, t3 and t4, respectively. As the sound beam 272 initially impinges on the front surface 280 of the tissue 276 at time t1, heat is created which begins to form the lesion 278 (FIG. 26A). As time passes on to t2, and t3 (FIGS. 26B and 26C, the ablation zone 278 continues to grow in diameter and depth. This time sequence from t1 to t3 takes as little as 3 to 5 seconds, depending on the ultrasound energy density. As the incidence of the ultrasound beam is continued beyond time t3, the ablation lesion 278 grows slightly in diameter and length, and then stops growing due to the steady state achieved in the energy transfer from its ultrasound form to the thermal form. The example shown in of FIG. 26D shows the lesion after an exposure t4 of approximately 30 seconds to the ultrasound beam 272. Thus the lesion reaches a natural limit in size and does not grow indefinitely.

The ultrasound energy density determines the speed at which the ablation occurs. The acoustic power delivered by the transducer divided by the cross sectional area of the beamwidth determines the energy density per unit time. In this invention, effective acoustic power ranges from 0.3 watt to >10 watts, and the corresponding energy densities range from 3 watts/cm.sup.2 to >100 watts/cm.sup.2. These energy densities are developed in the ablation zone. As the beam diverges beyond the ablation zone, the energy density falls such that ablation will not occur, regardless of the time exposure.

One aspect of this invention is to provide a device which will produce an ablation zone across the entire thickness of the wall of the atrial tissue in order to completely block the conduction of abnormal electrical impulses. This is termed as a transmural lesion. The transmural lesion 279, as shown in FIG. 26C, is formed when the entire thickness of the tissue 276 is in the ablation window 2172, and sufficient time is allowed for the lesion to develop.

The dependence of the formation of the ablation zone 278 on the gap distance 282 between the catheter tip and the tissue surface is shown in FIGS. 27A-D. For a uniformly collimated beam, as the gap distance 282 increases, the depth 288 of the ablation zone 278 remains constant. Even for cases where the beam is not uniformly collimated, as in the case of this invention where the beam convergences slightly over distance L, the depth 288 of the ablation zone 278 varies little as long as the tissue resides in an approximately collimated zone L. This distance L where the ultrasound beam 272 is approximately collimated, and where an ablation zone is effectively created, is termed as the ablation window 2172. Thereafter the depth 288 decreases dramatically mainly due to the divergence of the ultrasound beam 272.

In practice, the amount of beam convergence can be varied to partially compensate for tissue attenuation, thereby creating more uniform energy densities within the ablation window. This compensation helps reduce the variations in depth 288 of the ablation zone 278 for tissues falling in the ablation window 2172.

There is another important factor contributing to uniform ablation depths 288 within the ablation window 2172 independent of the gap distance 282. The sound beam travels through the cooling fluid and blood in the gap 282 with very little attenuation. Therefore almost the entire acoustic energy is available and presented to the tissue 276 beginning at the front surface of the tissue 280.

Figure 28A:
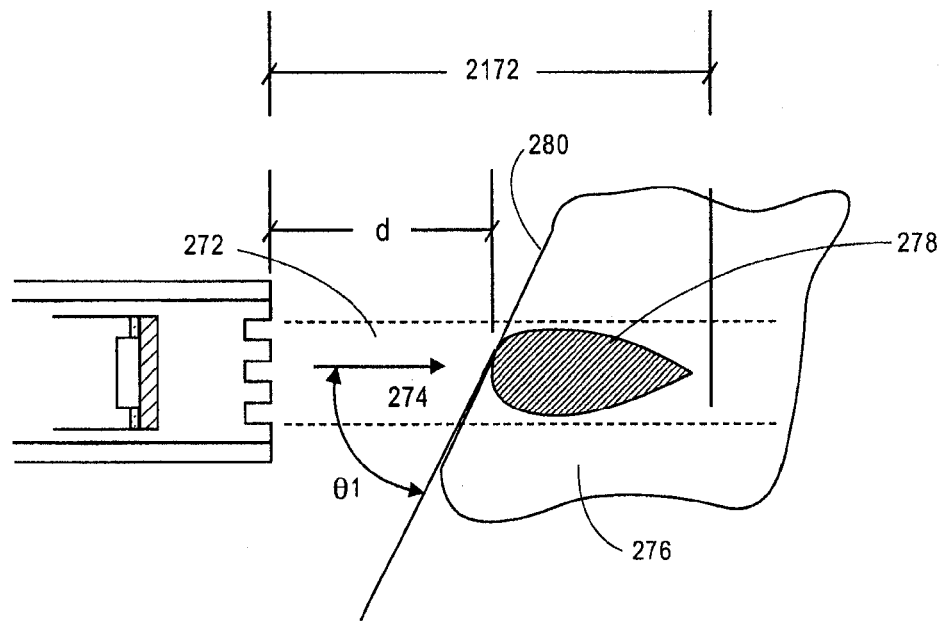
FIGS. 28 A-B are views of the interaction of the ultrasound beam with the tissue when the tissue is presented to the beam at an angle.
Figure 28B:
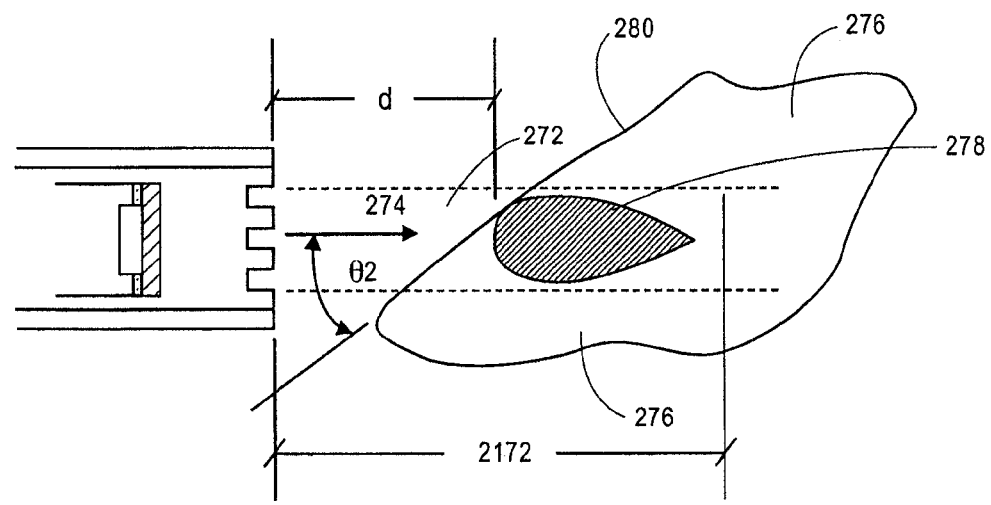

For the practical use of the device of this invention, the discussion of some of the important parameters is presented. Above, we discussed the gap distance 282. The gap distance 282 is the distance between the distal end of the castle head 2238 and the front surface 280 of the tissue 276. Now we discuss the angle of incidence as shown in FIGS. 28A and 28B. The tissue 276 is presented to the ultrasound beam 272 such that its front face 280 is at an angles θ1 and θ2 to the beam 272 at a gap distance 282. The resulting ablation 278 is formed in the tissue in the line of the direction 274 of the beam travel. The formation of the zone 278 is somewhat independent of the angle of incidence θ. Again, as long as the tissue 278 is presented to the ultrasound beam 272 within the ablation window 2172, the resulting ablation zone 278 profiles will be generally similar in shape, size, and depth and somewhat independent of the incidence angle θ.

Figure 29:
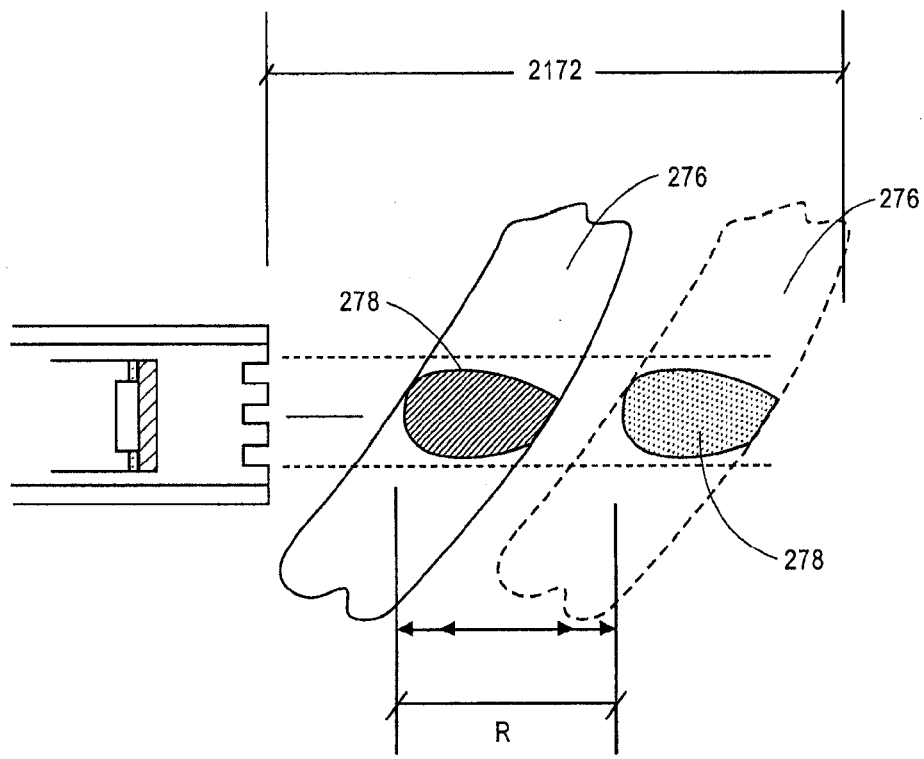
FIG. 29 shows the effect of the movement of heart muscle during ablation.

In the actual clinical setting, the wall of the atrial tissue is moving within some physical distances. In order to achieve a contiguous transmural lesion in the moving wall of the atrium, the entire movement must be within the ablation window 2172. As shown in FIG. 29, the atrial wall tissue 276 is moving over a distance of R within the ablation window 2172. So long as the movement R is within the ablation window 2172, an effective transmural lesion 278 will be created. Therefore it is important to position the castle head 2238 close enough to the endocardial surface of the atrial wall to ensure a transmural lesion in a moving wall.

Figure 19:
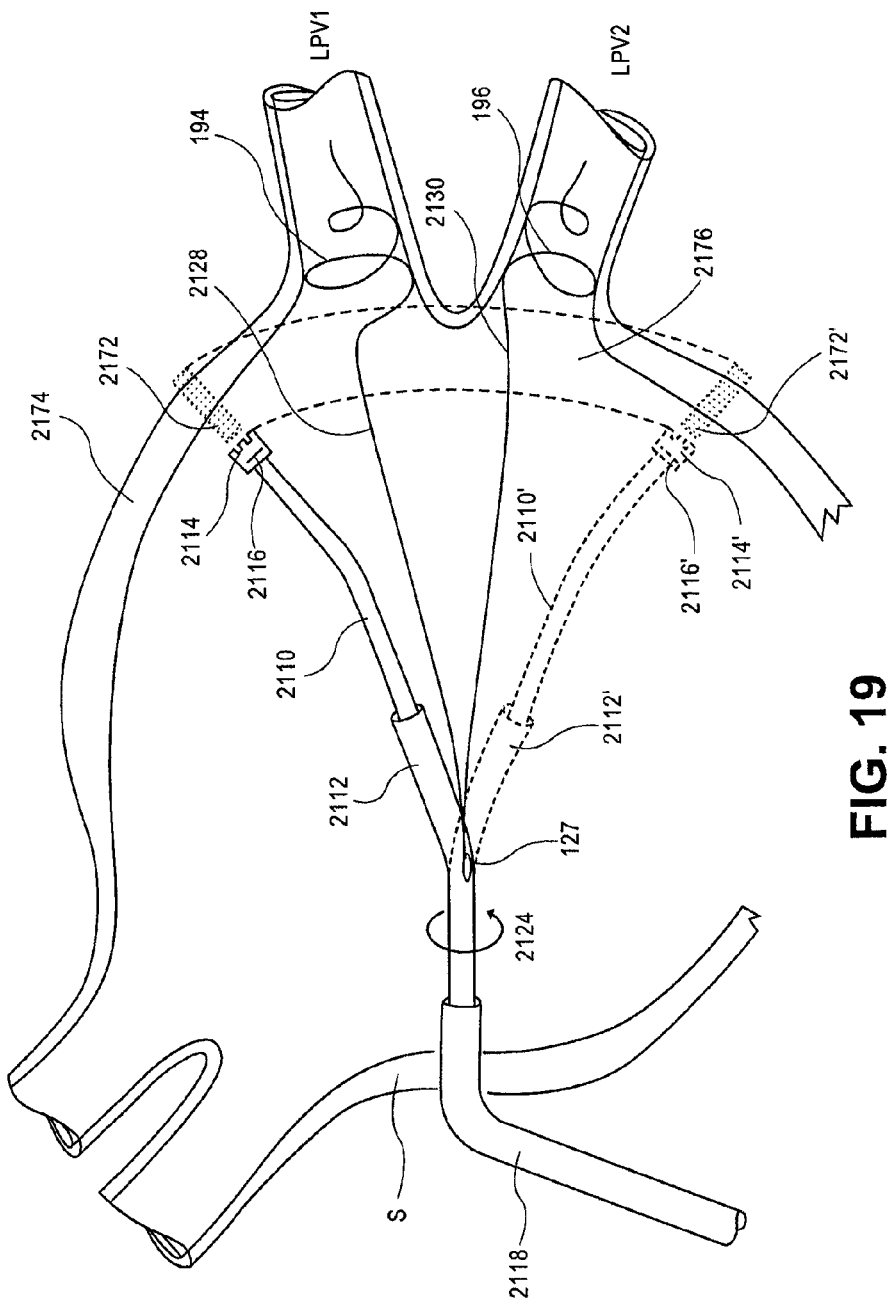
FIG. 19 shows the use of the device of FIG. 18 in the atrium of the heart.

One aspect of this invention is to present the ultra-sound beam to the atrial tissue and move it across the tissue such that a contiguous ablation zone (lesion) is created in the tissue wall. Referring to FIG. 19, the zone 2172 depicts the cylindrical region in front of the transducer 2116 where the atrial wall tissue 2174 is effectively ablated. As the catheter 2112 is rotated in the manner 2124, the zone 2172 sweeps in a circle creating a section 2176 of a cone. The catheter housing 2114 can also be moved inside the atrium in geometry other than a circle by utilizing the various other movements available for the catheters 2110 and 2112. Thus the sweeping ultrasound beam will form a complex pattern 2176 inside the atrium. The atrial wall tissue 2174 intersects this pattern 2176 forming a somewhat complex shaped lesion of ablated tissue. The important requirement for effective therapy is to create a contiguous transmural lesion which will serve as a conduction block in stopping the aberrant electrical pathways in the atrium which cause the fibrillation of atrial tissue.

Referring to FIG. 18, the ultrasound transducer 2116 is connected to an electrical generator (not shown) by means of the connector 2170 which contains the wires 214 and 216 connected to the two faces of the transducer 2116. When energized by the generator (not shown), the transducer 2116 emits ultrasound energy at a frequency in the range of 1 to 20 megaHertz (MHz). A practical range of frequency is 5 to 15 MHz. It is well understood in physics of ultrasound, as the frequency increases, the depth of penetration of ultrasound energy in to the tissue is reduced resulting in an ablation zone 276 (ref. FIG. 25) of shallower depth 288. The energy of the ultrasound beam 272 is determined by the excitation voltage applied to the transducer. The generator provides the appropriate frequency and voltage to the transducer to create the desired sound beam 272. For the purpose of the description of this invention, we are using a frequency in the range of 5 to 15 MHz, and a voltage in the range of 10 to 100 volts peak-to-peak. In addition, a variable duty cycle can be used to control the average power delivered to the transducer. The duty cycle ranges from 0% to 100%, with a repetition frequency of approximately 40 kHz, faster than the time constant of thermal conduction in the tissue. This results in an ablation zone 278 which is created within 2 to 5 seconds, and is of depth 288 of approximately 5 millimeters (mm), and of a maximum diameter of approximately 2.5 mm in correspondence to the diameter of the transducer 2116. It is understood that the ultrasound transducer of different diameters and frequencies can be used and different voltages and duty cycles can be applied to get various outputs of ultrasound power resulting in different sized ablation zones 278.

A contiguous transmural lesion is intended as the ultrasound beam 272 is swept across the atrial wall. Therefore, it would be desirable to know if a contiguous transmural lesion is indeed being created as the ultrasound beam is moved across the moving atrial wall. This is achieved by using the same ultrasound transducer 2116 in a diagnostic mode as described below.

The effectiveness of the creation of a transmural lesion 279 is in knowing and ensuring that the atrial wall tissue 2174 is being presented to the ultrasound beam with the pattern 2176 for effective ablation (ref. FIG. 19). This is achieved by using the same ultrasound transducer 2116 for the purpose of tissue detection. On the one hand, in order to achieve ablation (i.e. killing of the live tissue cells), the ultrasound beam of sufficient energy is delivered to the tissue in a substantially continuous manner such that the energy input exceeds the thermal relaxation provided by the cooling due to the surrounding tissue. This mode of energizing the ultrasound transducer 2116 is termed as the ablation mode. On the other hand, the tissue detection is done by utilizing a pulse of ultrasound of short duration which is generally not sufficient for heating of the tissue. Ultrasound has been traditionally used for diagnostic purposes for a number of years. Typical uses are fetal ultrasound imaging, intravascular ultrasound imaging, and the like. For the purpose of this invention, we use the ultrasound to detect the gap (namely, the distance of the tissue surface from the castle head), the thickness of the tissue targeted for ablation, and the characteristics of the ablated tissue. This mode of energizing the transducer 2116 is termed as the diagnostic mode. One objective of this invention is to utilize the diagnostic mode in guiding the therapy provided by the ablation of the tissue.

This invention uses a simple ultrasound imaging technique, referred to in the art as A Mode, or Amplitude Mode imaging. A short electrical pulse or train of pulses excites the ultrasound transducer creating a short duration ultrasound pulse wave that propagates into the blood and tissue. As the ultrasound pulse travels through the tissue, some of the acoustic energy is backscattered to the transducer, which converts the returning acoustic signal into an electrical voltage. The amplitude of the voltage is sensed in a receiver (not shown), as a function of the time elapsed from the initial transmitted pulse. Since ultrasound travels through blood and soft tissue at a known and approximately constant speed, the receiver can determine the distance from which the returning signals originate. The amplitude of the returning signals depends on the acoustic properties of the tissue. Homogeneous tissue backscatters the sound as the pulse wave propagates through it. Different tissues create differing amounts of backscatter, so the returning ultrasound signal has different amplitudes depending on the type of tissue. As the pulse travels passes from one tissue to another, a reflection occurs, the amplitude of which is determined by the acoustic impedance difference of the two tissues.

Figure 30:
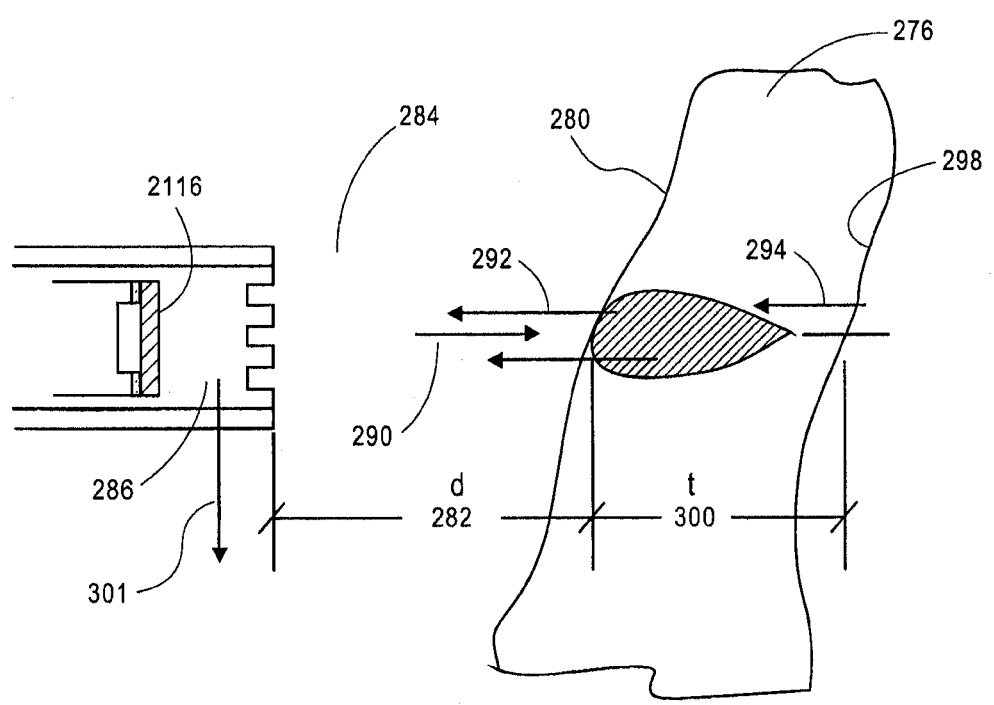
FIG. 30 shows the transmission and reflections of ultrasound beam from the target tissue.

Referring to FIG. 30, the transducer 2116 sends a pulse 290 of ultrasound towards the tissue 276. A portion of the beam is reflected and backscattered as 292 from the front surface 280 of the tissue 276. This reflected beam 292 is detected by the transducer 2116 a short time later and converted to an electrical signal which is sent to the electrical receiver (not shown). The reflected beam 292 is delayed by the amount of time it takes for the sound to travel from the transducer 2116 to the front boundary 280 of the tissue 276 and back to the transducer 2116 now serving as an ultrasound detector. This travel time represents a delay in receiving the electrical signal from the transducer 2116. Based on the speed of sound in the intervening media (saline fluid 286 and blood 284), the gap distance d (282) can be determined. As the sound beam travels further into the tissue 276, a portion 294 of it is reflected from the back surface and travels towards the transducer. Again, the transducer converts this sound energy into electrical signals and the generator converts this information into the thickness t (300) of the tissue 276 at the point of the incidence of the ultrasound pulse 290. As the catheter housing 2114 is traversed in a manner 301 across the tissue 276, the ultrasound transducer continuously detects the gap distance d (282) and the tissue thickness t (300). This information is used in delivering continuous ablation of the tissue 276 during therapy as discussed below.

The returning echo from tissue boundaries has the same time duration as the transmitted pulse. The returning backscattered signal from the bulk of the tissue has a time duration equal to the path length of the pulse through the tissue. The returning signal from tissue 276 then is a composite of two short relatively high amplitude pulses returning from the front wall 280 and back wall 298, along with the backscatter from within the tissue. The amplitude of the back-scatter from the tissue will change as the pulse traverses the ablated tissue and the normal tissue. Therefore, by measuring the relative amplitudes of the returning signal, the receiver can determine the depth of the front wall, the depth of the lesion, residual tissue depth that is not yet ablated, and the depth of the back wall.

The receiver compares the time delay of the first echo from the face of tissue 280 to a time threshold corresponding to the ablation window length 2172. If the time delay is less than the threshold, this indicates that the front face of the tissue 280 lies within the window length 2172. The receiver can indicate this by a display means, for example lighting a 'green' display. If the receiver detects the echo arriving later than the time threshold, then a 'red' display can be lit indicating that the gap 282 is too large, and a lesion may not be created in the tissue.

Figure 31:
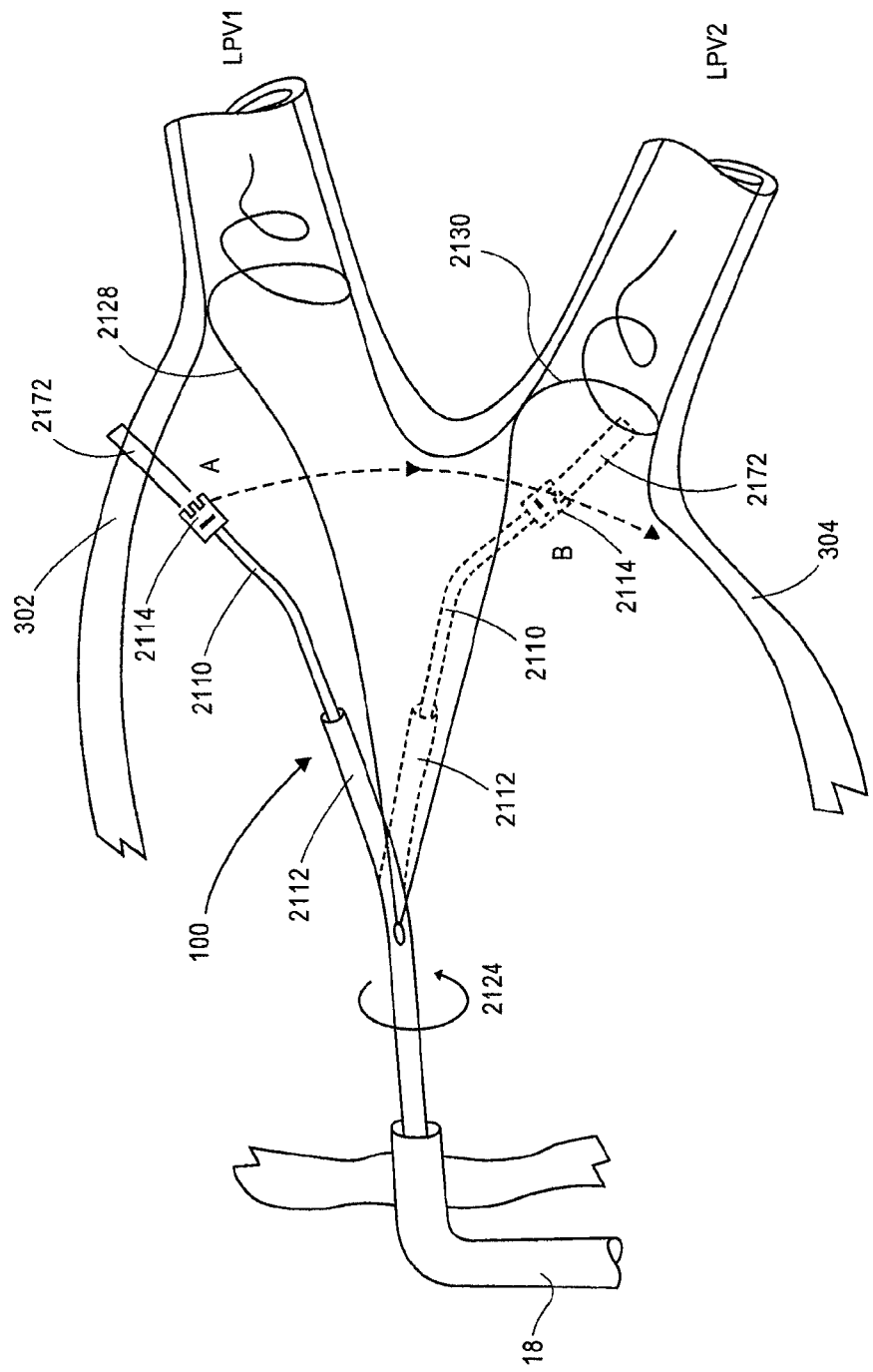
FIG. 31 shows position of the catheter set in the left atrium in a condition when it may not be desirable to create an ablation zone.

The use of the above information in an actual clinical setting is depicted in FIG. 31. The catheter 100 of catheters 2110 and 2112 is introduced into the atrial chamber through the guide sheath 2118. The positioning wires 2128 and 2130 are advanced in to the two left pulmonary veins LPV1 and LPV2. In the diagnostic mode, the outer catheter 2112 is rotated in a manner 2124, the housing 2114 at the tip of the therapy catheter 2110 rotates in the atrial chamber. When the catheter is in position A near the LPV1, the ablation window 2172 intersects with the tissue wall 302. This indicates a condition that the ablation of the tissue in its entire thickness can be achieved and is indicated by a 'green' light. As the housing 2114 continues to sweep the atrial chamber, it reaches position B near the LPV2. Here the ablation window 2172 does not intersect the tissue wall 304. This indicates a condition that the tissue is either too far, or the ultrasound beam is pointed towards a structure such as a PV, or the atrial appendage, or the mitral valve opening. In this case, transmural ablation will not be achieved and a 'red' light will be indicated.

It is the objective of the user physician to establish a contiguous beam path 2176 (ref. FIG. 19) indicated by the 'green' light continuously lit during the movement along the entire intended lesion path. A check for this continuous green light, before energizing the ultrasound transducer, will insure that the proposed path will result in a contiguous ablation zone in the atrial wall. The situation shown in FIG. 31 does not yield a contiguous beam path, therefore the physician would move the catheters 2110 and/or 2112 and sweep another circle of the housing 2114 in diagnostic mode to arrive at a situation such as that shown in FIG. 19. Once such contiguous path 2176 is established in the diagnostic mode, the physician can proceed with the ablation of the said path using the ablation mode.

As an added safety feature, the system can regularly, on a time-shared basis, convert from ablation mode briefly to diagnostic mode. In this way, the correct gap can be checked even during the ablation. If the red light goes on, the system will automatically exit the ablation mode, until a correct gap (i.e. green light) is again detected. Then the ablation mode will be automatically resumed. This diagnostic sampling can occur at a relatively fast sampling frequency. In the current invention, it occurs at about 40 kHz, corresponding to the duty cycle repetition rate for the diagnostic power generator. Conversely, if the 'green' light remains lit throughout the movement along entire ablation path, then a contiguous lesion has been created. This measure off goodness can result in an additional display (flashing 'green' light, for example) to inform the physician that he has created a complete contiguous lesion.

Furthermore, since the wall thickness and the lesion depth can also be checked in the diagnostic mode on a timeshared basis during the ablation, the system can dynamically control the lesion depth by varying the sweep rate along the intended ablation path, and/or changing the power provided from the generator. In this way the lesion is even more likely to be transmural contiguously all along the lesion path. In addition, the system can minimize the possibility of creating a lesion beyond the atrial wall. If the system detects the lesion extending beyond the outer wall, the generator will be turned off. Alternatively, the system can be configured such that the generator is turned off when the depth of the lesion reaches or exceeds a preset depth.

Figure 32:
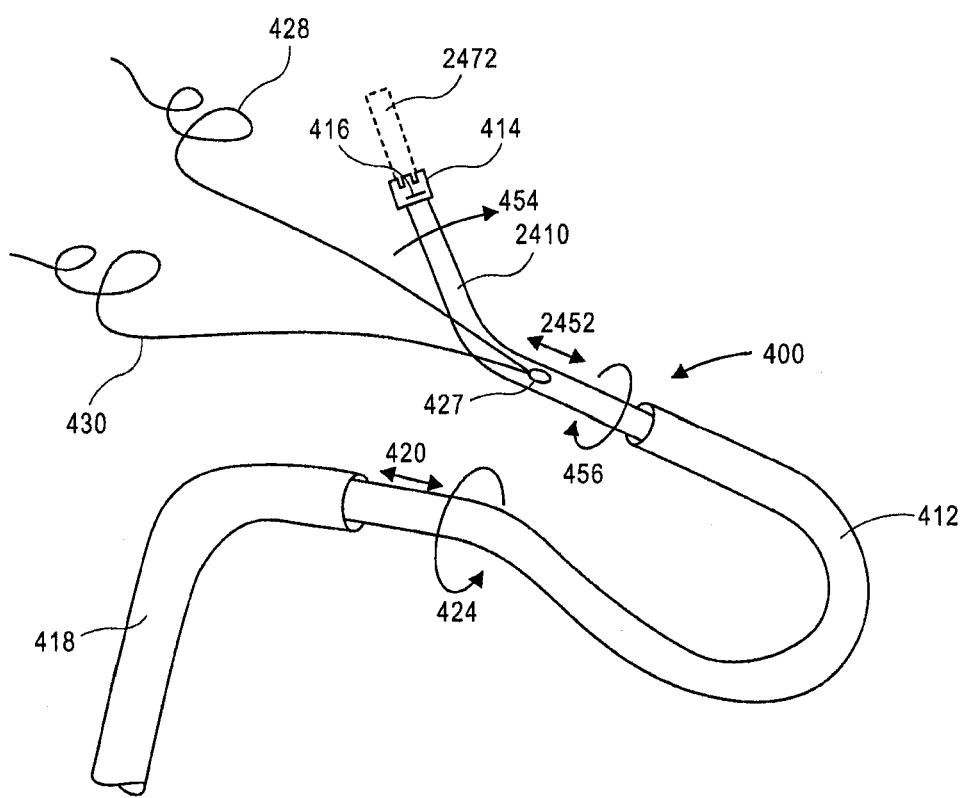
FIG. 32 shows a catheter set designed to address the right pulmonary veins.

The above description of the design and construction of the catheter set 100 is aimed at creating the ablation zone for the left pulmonary veins. A different catheter set is used for the right pulmonary veins, essentially of the same functioning principles but of a different geometry appropriate for the anatomical location of the right pulmonary veins in the left atrium of the heart. This catheter set 400 is shown in FIG. 32. The outer catheter 412 has a preset shape of a 'shepherd's hook' so as to point towards the right pulmonary veins when placed in the atrial chamber. The catheter 412 can move in the axial direction in the guide sheath 418 in a manner 420. The therapy catheter 2410 moves inside the outer catheter 412 in the axial direction in a manner 2452.

In addition, catheter 412 can rotate in a manner 424. A lumen 426 (not shown) in the catheter 2410 is used to house the positioning wires 428 and 430 which exit from the said lumen at the notch 427. The catheter 2410 can also be rotated in the catheter 412 in a manner 456. The distal tip portion of the catheter 2410 can be bent by means of a pull wire (not shown) in the manner 454. The distal tip of the catheter 2410 is composed of a 'castle head' housing 414 which contains the ultrasound transducer 416. The transducer has an ablation window 2472 similar to the ablation window 2172 (ref. FIG. 19) of catheter 2110. The additional construction of the elements of the catheter 2410 are identical to those of the catheter 2110 as described earlier in this specification. In addition, the catheter set 400 engages with the console 2132 in a similar manner as the catheter set 100.

Figure 33:
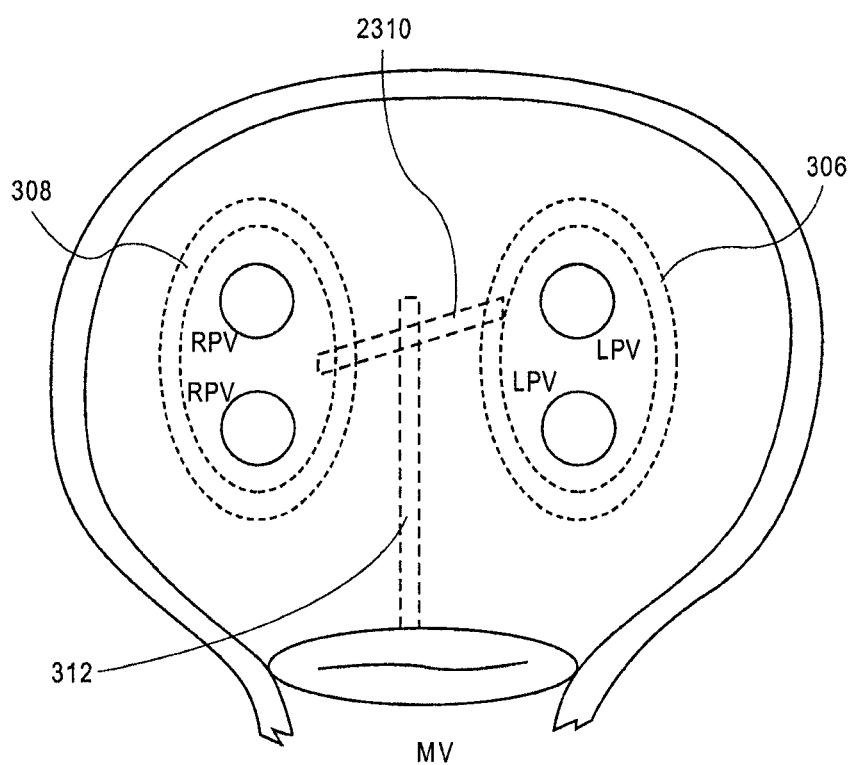
FIG. 33 shows a lesion set according to one embodiment of this invention.

Under the current state of knowledge, certain ablation lines are drawn in the atrium around the pulmonary veins in an attempt to block the conduction of aberrant electrical signals. This set of ablation lines is called a lesion set. In this invention, it is proposed to have a lesion set as shown in FIG. 33. One ablation ring 306 encircles the two left PV's and another ablation ring 308 encircles the right PV's. An ablation line 3310 is drawn joining the ablation rings 306 and 308. Finally, another ablation line 312 is drawn intersecting the ablation line 3310 and down to the annulus of the mitral valve (MV).

Next, a method for the use of the device of this invention in a clinical setting is presented as follows:

1. Referring to FIG. 18, position the guide sheath 2118 across the atrial septum S using the conventional femoral vein approach. One technique for this procedure is described by Gill (J. S. Gill, How to perform pulmonary vein isolation, Europace 2004 6(2):83-91).

2. Pre-load the positioning wires 2128 and 2130 in the lumen 2126 of the outer catheter 2112 such that the distal tips of the wires are entirely inside the lumen 2126.

3. Advance the catheter set 100 through the guide sheath 2118 into the atrial chamber.

4. Advance one of the positioning wire 2128 through the opening notch 127 of the outer catheter 2112. The conical spring like shape 194 of the wire will now deploy. Under conventional fluoroscopic guidance, position the wire in the pulmonary vein LPV1. The wire can be rotated gently to help it find and navigate the ostium and the opening of the pulmonary vein. Advance the wire slightly beyond the marker 129 at the proximal end to ensure its position inside the LPV1 then lock it in position using the lever 2136.

5. Advance the second positioning wire 2130, and guide its conical spring 196 into to second vein LPV2 in a similar manner., positioning it beyond the marker 131 at its proximal end and lock in position using the lever 2138.

Figure 34:
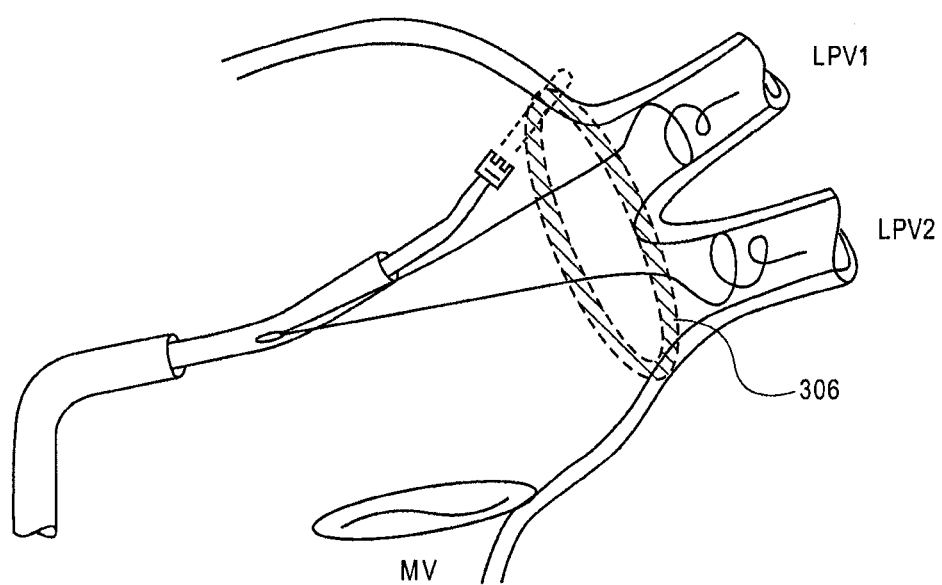
FIG. 34 shows the creation of an ablation zone near the left pulmonary veins.
Figure 35A:
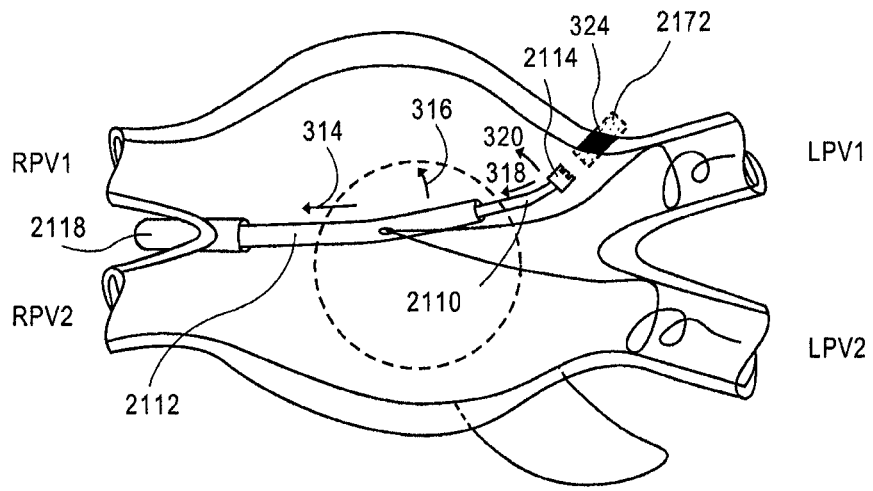
FIGS. 35A-C show the formation of a line lesion from the left pulmonary veins to the right pulmonary veins.
Figure 35B:
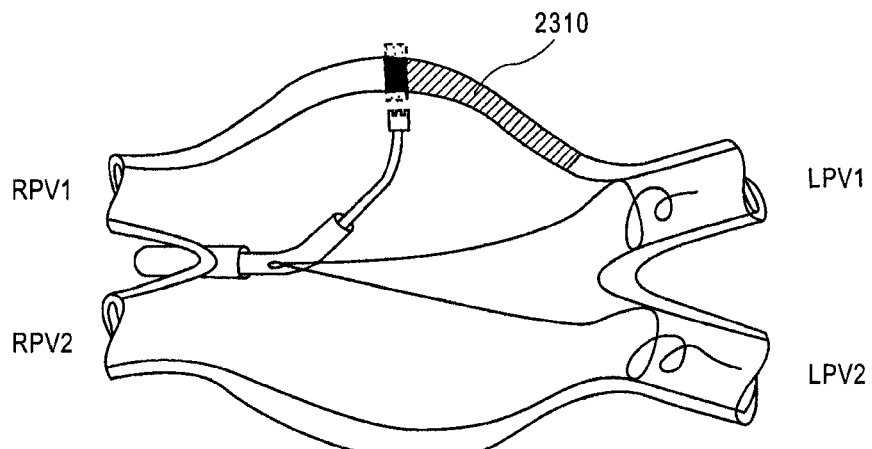
Figure 35C:
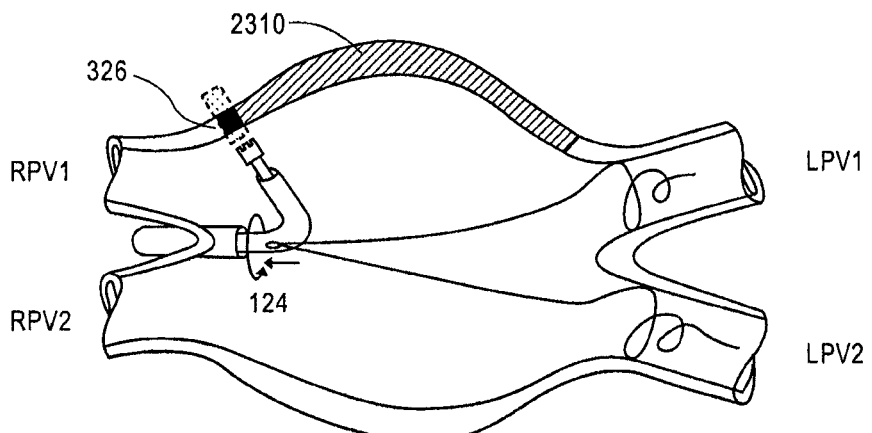

6. Referring to FIG. 34, move the outer catheter 2112 and the inner catheter 2110 to the most proximal position in the atrial chamber. Using the transducer 2116 in a diagnostic mode, rotate the outer catheter 2112 (either manually or using the motor drive of console 2132) in the chamber. The generator/receiver will sense for the position of the atrial wall tissue and indicate appropriately with a green or a red light.

7. If the red light indication exists in a portion of the rotation, use the linear or bending motions of the catheters 2112 and/or 2110 to achieve a complete green circle. At this point, a contiguous beam path 2176 has been established. In the diagnostic mode, the navigation through a circle is quite rapid and can be completed in several seconds. Since the circular movement can not continue in one direction only, reverse the direction of rotation after a rotation of 360 degrees plus an overlap of about 10 to 15 degrees. If the physician chooses for the motor drive to achieve this function, the drive unit is programmed to automatically reverse the direction after a complete circle plus an overlap.

8. Energize the transducer in the ablation mode and start the rotary motion of the catheter tip housing 2114 using the motor drive in the console 2132. This movement is much slower, and will typically take several minutes to complete. Confirm that the green light stays green through the entire movement.

9. If the red light persists over a portion of the circle, proceed with the ablation in the green zone, and later cover the red zone ablation in the following manner:

a. The physician can use the other linear and bending movements of the catheters to establish a path in a set of other planes which would yield a green path covering the region where the original red arc appeared.

b. The computer in the generator/receiver can memorize this complex green path, and upon activation, can establish an ablation zone in the tissue which is contiguous with the original green zone.

10. The ablation around the two left pulmonary veins LPV1 and LPV2 is now complete as shown as curve 306 in FIG. 34.

11. Next, the ablation lines 3310 and 312 of FIG. 33 are created using a method as shown in FIGS. 35A, 35B, 35C, and FIG. 36.

12. Starting at the position of the tip housing 2114 of the catheter 2110 at the end point of the just completed ablation ring 306 (FIG. 34), orient the tip 2114 posteriorly in the atrium using the orientation markers 2166 and 2168 (ref. FIG. 18) on the proximal ends of the catheters 2110 and 2112.

13. Advance the catheter 2112 distally towards the LPV1 a few millimeters to establish the starting point 324 of the ablation line 3310.

14. Using the diagnostic mode, move the catheter 2112 towards the right pulmonary veins in a manner 314 by pulling it into the guide sheath 2118. At the same time, bend the tip of the catheter 2112 in a manner 316. If necessary, move the therapy catheter 2110 inside the outer catheter 2112 in a manner 318, and bend the tip of the therapy catheter 2110 in a manner 320. All these movements are carried out to establish the locus of the ablation window 2172 in the green' region. Generally, this locus will be achieved by a combination of various movements of the catheters 2110 and 2112 and can be carried out by the computer in the generator/receiver. The finishing point 326 of this 'green' line is intended to be past the ostium of one of the right pulmonary veins. Once this horizontal green line 3310 is established, the computer can memorize the actual motions required therefor.

15. Follow through with the formation ablation line 3310 (FIG. 33) by moving the tip 2114 in the ablation mode all the while maintaining the 'green' light. The successive positions of the ablation window 2172 and the resulting ablation line is shown in the top view of the atrium in FIGS. 35B and 35C.

16. When the catheter tip is at its most proximal position, an ablation zone around the right pulmonary veins can be created as follows:

a. In diagnostic mode, rotate the catheter 2112 in a manner 2124 to establish a 'green' curve around the right pulmonary veins. Other available motions of the catheter set 100 can be utilized to establish a 'green' curve.

b. Once the 'green' curve is established, using the ablation mode, create the ablation zone 308.

17. Now referring to FIG. 36, move the tip 2114 of the catheter 2110 to an approximately middle position of the ablation line 3310, and a few millimeters clockwise (i.e. above the line 3310) to establish the starting position 328 for the vertical ablation line 312, as shown in FIG. 33.

18. Using the catheter in the diagnostic mode, rotate the catheter 2112 counterclockwise in the manner 2124, and ensure a 'green' path is established. The end point 330 of this line 312 is at the mitral valve annulus which can be detected by the transducer by virtue of the movements of the leaflet of the valve itself. If required, additional movements of the catheters can be used as appropriate to determine the locus of the 'green' line. Once this 'green' line is established, enable the computer to memorize the required movements.

19. Using the transducer in the ablation mode, form an ablation line 312 from the horizontal line 2110 down to the annulus of the mitral valve (MV).

20. Withdraw the positioning wires into the lumen of the catheter 2112 and withdraw the catheter set 100 from the body of the patient through the guide sheath 2118 while leaving the said guide sheath 2118 in position across the septum.

21. The ablation zone encircling the right pulmonary veins is made using a different catheter set specifically designed for that anatomy of the region of the atrium.

Figure 37:
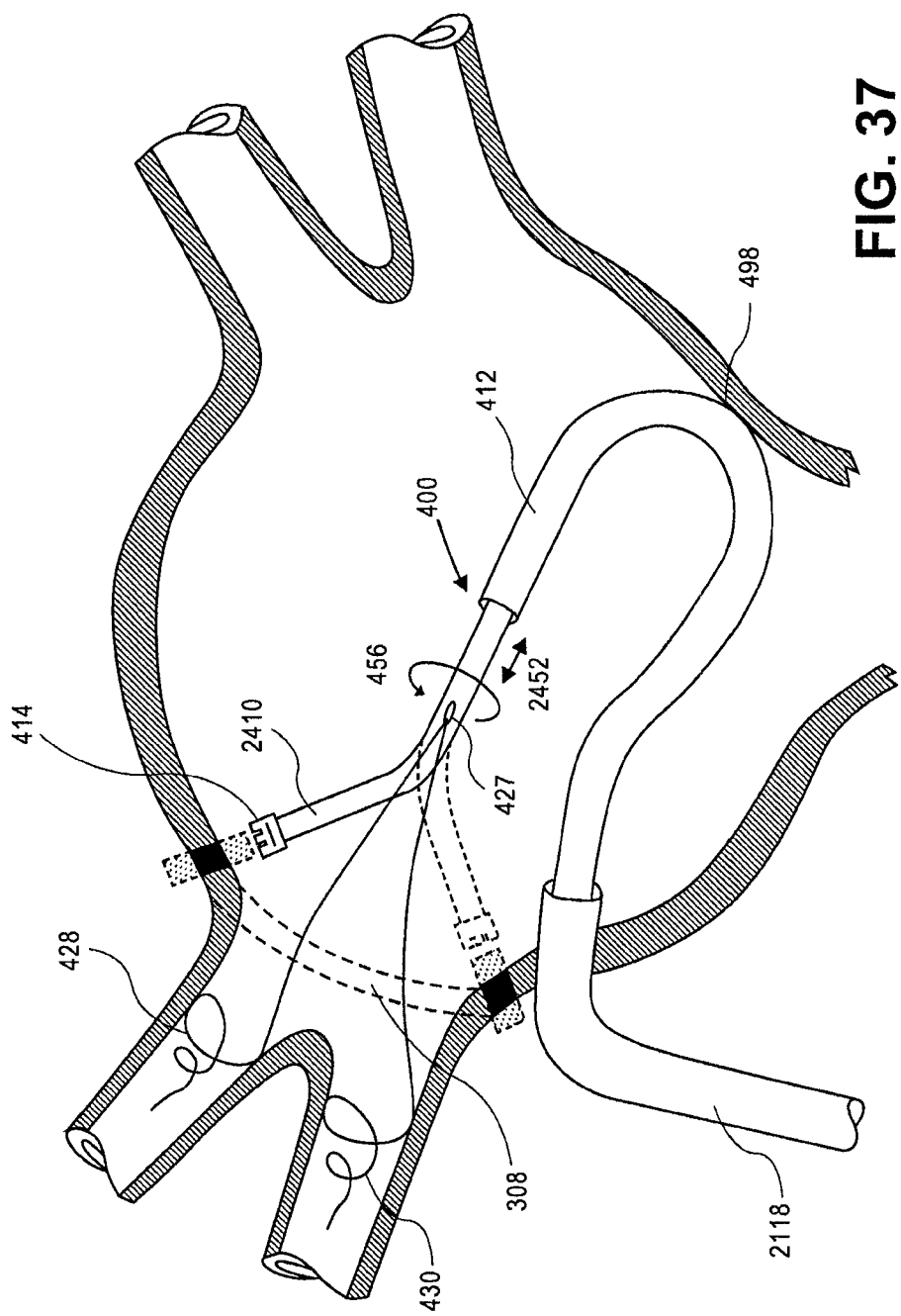
FIG. 37 shows the use of the device of FIG. 31 in creating the ablation zone in the right pulmonary veins.
Figure 38A:
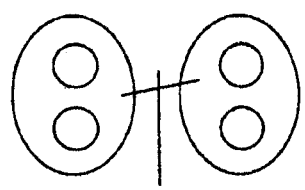
FIGS. 38A-J show a variety of candidate lesion sets in the left atrium.
Figure 38B:
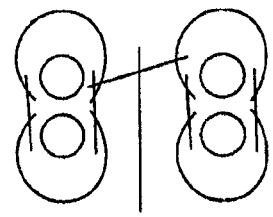
Figure 38C:
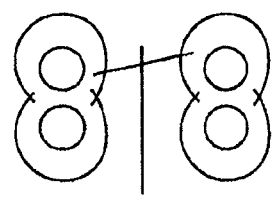
Figure 38D:
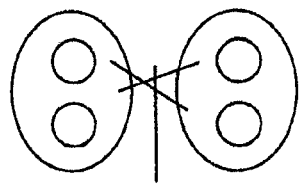
Figure 38E:
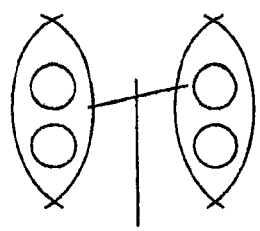
Figure 38F:
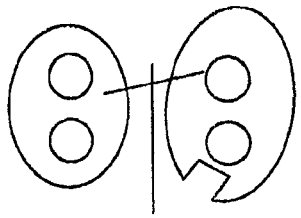
Figure 38G:
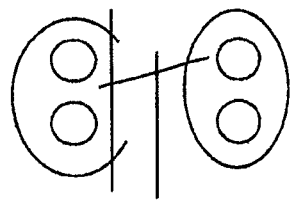
Figure 38H:
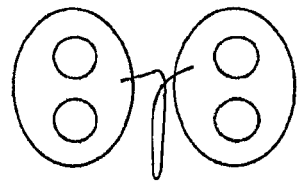
Figure 38I:
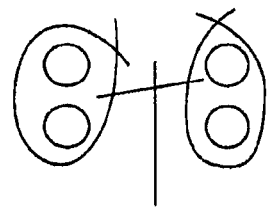
Figure 38J:
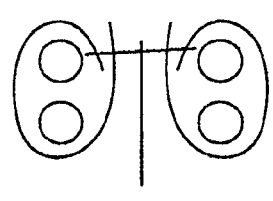

22. Referring to FIG. 37, advance the outer catheter 412 distally until its curved surface 498 is in contact with the inside left wall of the atrium.

23. Place the positioning wires 428 and 430 in the lumen 426 (not shown) of the catheter using the technique described earlier.

24. Position the wires 428 and 430 into the right pulmonary veins using the technique described earlier.

25. Advance the therapy catheter 2410 to its most distal position. Using the diagnostic mode, rotate the tip housing 414 of the catheter 2410 in the manner 456. Look for the presence of the 'green' circle.

26. If the 'green' circle is not established, move the catheter 2410 a few millimeters proximal in the manner 2452 and repeat step 25. Repeat this step 26 until a 'green' circle is established.

27. Now energize the transducer in ablation mode, and create the lesion 308 (FIG. 33).

28. If the 'red' light appears, follow the procedure in step 9 above.

29. The formation of the right PV ablation zone 308 is now complete.

30. Retract the positioning wires 428 and 430 from the atrium by withdrawing them through the lumen of the catheter 412.

31. Remove the catheter set 400 from the atrium through the guide sheath 2118.

32. Remove the guide sheath 2118 from the heart and follow the conventional closure technique for the femoral vein.

The procedure above describes the formation of one lesion set. As the catheter sets 100 and 400 are provided with multiple degrees of motions, the physician can create a variety of other lesion sets to achieve a conduction block. FIG. 38 shows some of the lesion sets which can be created with the device of the present invention. The possible lesion sets are not limited to those presented here, and it is important to recognize that the device of this invention allows the physician to create any other lesion set in the atrium of the heart.

In a conventional catheter-based ablation procedures, the physician check the presence or absence of the conduction block by mapping of the atrial tissue. The technique involves checking the electrical conduction between the pulmonary veins and the other parts of the atrial wall on the endocardial side. The wires 428 and 430 are already positioned inside the pulmonary veins and can be easily used as electrodes for the sensing and mapping purposes. The electrical connections to the positioning wires 428 and 430 are provided at the console 2132.

This specification for the present invention discusses an ultrasound transducer as a single element in the shape of a disc mounted at the end of a cylindrical catheter. This invention is not intended to be limited to the use of a single element circular disc. A rectangular or oval shaped transducer can be mounted on the cylindrical side of the catheter tip. Appropriate fluid flow mechanism can be provided to cool the said transducer and to provide for the separation of the surrounding blood from the surface of the transducer. In addition, the transducer configuration is not intended to be limited to that of a disc. The transducer can be in the form of an array of multiple transducers. The transducer can also be fabricated as a set of concentric circles (known in the art as an annular array), for example, instead of the single element disc described in this invention. One skilled in the art will appreciate the wide possibility of possible shapes, sizes, and configurations which can be used for the transducer in this invention.

This specification of the present invention discusses the use of a console 2132 that allows simple control of the catheter sets 100 and 400. This invention is not intended to be limited to the use of this console. The catheter sets, with appropriate modifications, can also be controlled and manipulated by other means, for example mechanical robotic or magnetic controllers with remote user interfaces that manage all motions, with or without haptic feedback.

In some embodiments, the tip of the treatment catheter and the anchor can both be made of metal and can communicate electrically with the control system so that they can serve as mapping electrodes for determining the electrical characteristics of the heart tissue.

The description above of the device of this invention has been limited to the treatment of atrial fibrillation in the left atrium of the heart. However, the device, with appropriate modifications, can be used in other parts of the body. For example, if it is determined that the right atrium is also involved in the condition of atrial fibrillation, appropriate lesion set can be created in the wall of the right atrium as well. Another example is the use of another version of the device in the ventricular space for the treatment of ventricular arrhythmia. The transducer creates an ultrasound beam which is capable of creating transmural lesions in the myocardial tissue, and this beam can be moved around in the chambers of the heart to create intended lesions in the wall of the heart.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method for creating a lesion in cardiac tissue, the method comprising:

positioning at a first location within a heart of a patient, an ultrasound transducer coupled to a distal portion of a catheter;

sweeping the ultrasound transducer along a first ablation path;

sensing a distance between the ultrasound transducer and the cardiac tissue, wherein sensing occurs while the ultrasound transducer is sweeping along the first ablation path, and wherein sensing generates an indicator signal;

checking the indicator signal to ensure that the first ablation path will result in a continuous transmural lesion; and ablating the cardiac tissue with a beam of energy from the ultrasound transducer along the first ablation path to form the lesion, wherein the ablation depth is dynamically controlled by varying a sweep rate of the ultrasound transducer along the first ablation path during ablation.

2. The method of claim 1, wherein the lesion is formed without contact between the ultrasound transducer and the target tissue.

3. The method of claim 1, wherein the same ultrasound transducer performs the sensing and the ablating.

4. The method of claim 1, wherein sweeping the transducer comprises one or more of bending and rotating the catheter.

5. The method of claim 1, further comprising moving the catheter to a second location with the heart, sweeping the transducer along a second ablation path, and ablating the cardiac tissue along the second ablation path.

6. The method of claim 5, wherein moving the catheter comprises one or more of inserting, retracting, bending, or rotating the catheter.

7. The method of claim 5, wherein moving the catheter comprises moving the catheter with a console and a control system coupled to the catheter.

8. The method of claim 5, wherein moving the catheter comprises one or more of moving the catheter manually and moving the catheter with a microprocessor-controlled system.

9. The method of claim 1, wherein sensing comprises operating the ultrasound transducer in a diagnostic mode and wherein ablating comprises operating the ultrasound transducer in an ablation mode.

10. The method of claim 9, further comprising converting regularly from ablation mode to diagnostic mode and from diagnostic mode to ablation mode in order to generate an updated indicator signal while ablating the cardiac tissue along the first ablation path.

11. The method of claim 10, further comprising adjusting the sweep rate along the first ablation path based on the updated indicator signal.

12. The method of claim 1, wherein sweeping the ultrasound transducer along the first ablation path comprises sweeping the ultrasound transducer at the sweep rate, wherein the sweep rate is configured to allow sufficient time for the lesion to develop during ablation.

13. The method of claim 1, wherein sensing comprises sensing at least a portion of an ultrasound beam generated by the ultrasound transducer and reflected back toward the ultrasound transducer by the cardiac tissue.

14. The method of claim 1, wherein the amplitude of the reflected ultrasound beam depends on the acoustic properties of the cardiac tissue.

15. The method of claim 1 wherein sensing further comprises one or more of determining a residual tissue depth which has not been ablated or the depth of the lesion.

16. The method of claim 15, further comprising halting ablation if the depth of the lesion the thickness of the cardiac tissue.

17. The method of claim 1, further comprising adjusting a convergence of the beam of energy so as to compensate for an attenuation of the cardiac tissue.

18. The method of claim 1, further comprising adjusting the distance between the ultrasound transducer and the cardiac tissue based on the indicator signal such that ablating the cardiac tissue along the first ablation path forms a continuous transmural lesion.

19. The method of claim 1, further comprising bending the distal portion of the catheter, wherein the catheter comprises at least one pull wire and wherein bending the distal portion of the catheter comprises actuating the at least one pull wire.

20. The method of claim 1, wherein the indicator signal comprises a color-coded display.

* * * * *